US011680250B2

(12) United States Patent  
Felby et al.

(10) Patent No.: US 11,680,250 B2  
(45) Date of Patent: Jun. 20, 2023

(54) LIGHT-DRIVEN SYSTEM AND METHODS FOR CHEMICAL MODIFICATION OF AN ORGANIC SUBSTRATE

(71) Applicant: University of Copenhagen, Copenhagen K (DK)

(72) Inventors: Claus Felby, Veksø (DK); David Cannella, København N (DK); Klaus Benedikt Möllers, København Ø (DK)

(73) Assignee: University of Copenhagen, Copenhagen K (DK)

( * ) Notice: Subject to any disclaimer, the term of this patent is extended or adjusted under 35 U.S.C. 154(b) by 372 days.

(21) Appl. No.: 15/742,737

(22) PCT Filed: Jul. 14, 2016

(86) PCT No.: PCT/EP2016/066804  
§ 371 (c)(1),  
(2) Date: Jan. 8, 2018

(87) PCT Pub. No.: WO2017/009431  
PCT Pub. Date: Jan. 19, 2017

(65) Prior Publication Data  
US 2018/0208908 A1   Jul. 26, 2018

(30) Foreign Application Priority Data

Dec. 2, 2015 (DK) .......................... PA 2015 70789

(51) Int. Cl.  
*C12N 9/02* (2006.01)  
*C12P 19/14* (2006.01)  
(Continued)

(52) U.S. Cl.  
CPC ......... *C12N 9/0071* (2013.01); *C12N 9/0004* (2013.01); *C12N 13/00* (2013.01);  
(Continued)

(58) Field of Classification Search  
CPC .. C12N 9/0071; C12N 9/0073; C12N 9/0004; C12N 9/0008; C12N 13/00;  
(Continued)

(56) References Cited

U.S. PATENT DOCUMENTS 5,720,858 A    2/1998  Noceti et al.  
2010/0028488 A1*  2/2010  Lo ..................... A23K 20/158  
426/18

(Continued)

FOREIGN PATENT DOCUMENTS

WO    2003067213    8/2003  
WO    2008036916    3/2008  
(Continued)

OTHER PUBLICATIONS

Milucka et al., The ISME Journal, 2015, 9: 1991-2002 (Year: 2015).*

(Continued)

*Primary Examiner* — Allison M Fox  
*Assistant Examiner* — Qing Xu  
(74) *Attorney, Agent, or Firm* — Dinsmore & Shohl

(57) ABSTRACT

The present disclosure relates to a light-driven system which is able to chemically modify an organic substrate with high efficiency and in a cost-effective manner. Also provided are methods for chemically modifying an organic substrate using the present systems and methods for manufacturing such systems.

16 Claims, 29 Drawing Sheets

(51) Int. Cl.
    *C12N 13/00*     (2006.01)
    *C12P 7/04*     (2006.01)

(52) U.S. Cl.
    CPC ............... *C12P 7/04* (2013.01); *C12P 19/14* (2013.01); *C12Y 114/00* (2013.01)

(58) Field of Classification Search
    CPC .......... C12Y 114/00; C12Y 114/18003; C12Y 114/13025; C12Y 114/13
    See application file for complete search history.

(56) References Cited

U.S. PATENT DOCUMENTS

| | | | | |
|---|---|---|---|---|
| 2011/0008861 | A1* | 1/2011 | Berry ....................... | C12P 5/02 435/161 |
| 2011/0020914 | A1* | 1/2011 | Abou-Nemeh .......... | C12N 1/38 435/257.4 |
| 2011/0151507 | A1* | 6/2011 | van Walsem ............. | C12P 7/16 435/41 |
| 2014/0059719 | A1* | 2/2014 | Wogulis ................. | C07K 14/38 800/298 |

FOREIGN PATENT DOCUMENTS

| | | |
|---|---|---|
| WO | 2012019151 | 2/2012 |
| WO | 2012061517 | 5/2012 |
| WO | 2013096244 | 6/2013 |
| WO | 2013096369 | 6/2013 |
| WO | 2014072389 | 5/2014 |
| WO | 2014104165 | 9/2014 |
| WO | 2015004098 | 1/2015 |
| WO | 2015050809 | 4/2015 |
| WO | 2015057520 | 4/2015 |
| WO | 2015077573 | 5/2015 |

OTHER PUBLICATIONS

Wikipedia printout of Chlorophyllide, downloaded on Oct. 6, 2020 from the website: https://en.wikipedia.org/wiki/Chlorophyllide (Year: 2020).*
Chlorophyta printout of Smith, downloaded on Oct. 9, 2020 from Dr. Smith's Algal website: www1.biologie.uni-hamburg.de/b-online/library/webb/BOT311/Chlorophyta/Chlorophyta-100.htm (Year: 2020).*
Ito et al., RSC Advances, 2014, 4: 8645-8648 (Year: 2014).*
Sabbadin et al., Nature Communications, 2018, 9:756, pp. 1-12 (Year: 2018).*
Printout of Chloroplasts and Photosynthesis, Molecular Biology of the Cell, 4th edition, downloaded on Dec. 3, 2021 from the website https://www.ncbi.nlm.nih.gov/books/NBK26819/ (Year: 2021).*
Bissaro, B. et al., Controlled depolymerization of cellulose by light-driven lytic polysaccharide oxygenases, Nature Communications, 11:890, Year: 2020.
Blossom, B. et al., Photobiocatalysis by a Lytic Polysaccharide Monooxygenase Using Intermittent Illumination, ACS Sustainable Chemistry & Engineering, 8: 9301-9310, Year: 2020.
Antanova et al. "Ascorbic acid and xylem development in trunks of the *Siberian larch* trees". Russian J. Plant Physiology. 2005. 52 83-92.
Balzani et al."Designing Dendrimers Based on Transition-Metal Complexes. Light-Harvesting Properties and Predetermined Redox". 1998. Acc. Chem. Res., 31 (1), pp. 26-34.
Bennati-Granier et al. "Substrate specificity and regioselectivity of fungal AA9 lytic polysaccharide monooxygenases secretd by Podospora anserine". Biotechnol.Biofuels.2015. 8,90.

Berepiki et al. "Tapping the unused potential of photosynthesis with a heterologous electron sink" ACS Synth. Biol., Jul. 20, 2016.
Bissaro et al. "Fueling biomass-degrading oxidative enzymes by light-driven water oxidation" Green Chem., 2016, 18, 5357-5366.
Cannella et al. "Light-driven oxidation of polysaccharides by photosynthetic pigments and a metalloenzyme" Nature Communications, 7:11134.
Cannella et al. "Production and effect of aldonic acids during enzymatic hydrolysis of lignocellulose at high dry matter content". Biotechnology for biofuels, 2012.
Caputo et al. "Carbon nitride-TiO2 hybrid modified with-hydrogenase for visible light driven hydrogen production" Chem Sci. 2015, 6, 5690-5694.
Chaudhary et al."Visible light driven CO2 reduction by enzyme coupled CdS nanocrystals" Chem Commun (Camb), 2012, 48(1): 58-60.
Genty et al. "The relationship between the quantum yield of photosynthetic electron transport and quenching of chlorophyll fluorescence". Biochim Biophys Acta. 1989. 990, 87-92.
Harris et al. "Stimulation of Lignocellulosic Biomass Hydrolysis by Proteins of Glycoside Hydrolase Family 61: Structure and Function of a Large, Enigmatic Family".Biochemistry—Us 49. 2010. 3305-3316.
Hemsworth et al. "Discovery and characterization of a new family of lytic polysaccharide monooxygenases" Nat Chem Biol. Feb. 2014, 10(2):1222-6.
Holm-Hansen. "Chlorophyll a Determination: Improvements in Methodology". Oikos. 1978. 30 438-447.
Horn et al. "A reliable reducing end assay for chito-oligosaccharides" Carbohyd Plym 2004, 56, 35-39.
Hu et al. "Substrate factors that influence the synergistic interaction of AA9 and cellulases during the enzymatic hydrolysis of biomass" Energy Environ. Sci., 2014, 7, 2308-2315.
Lichtenthaler et al. "Chlorophylls and carotenoids: Measurement and Characterization by UV-VISSpectroscopy".Cur. Protocols in food analyt.chem. 2001.
Mifsud et al. "Photobiocatalytic chemistry of oxidoreductases using water as the electron donor" Nature Communications, 5:3145.
Nielsen et al. "Redirecting photosynthetic reducing power towards bioactive natural product synthesis" ACS Synth. Biol., 2013, 2, 308-315.
Onuchic et al. "Pathway Analysis of Protein Electron-Transfer Reactions". Annu Rev Biophys Biomol Struct. 1992. 21, 349-377.
Perez et al. "Visible light-driven and chloroperoxidase-catalyzed oxygenation reations" Chem. Commun., 2009, 6848-6850.
Quinlan et al. "Insights into the oxidative degradation of cellulose by a copper metalloenzyme that exploits biomass components" Proc . Nat Acad. Sci. 2011,108 1579-1584.
Rodrigues-Zuniga et al. "Lignocellulose pretreatment technologies affect the level of enzymatic cellulose oxidation by LPMO". Proc Nat Acad Sci. 2015. 108 1579-1584.
Westereng et al. "Efficient separation of oxidized cello-oligosaccharides generated by cellulose degrading lytic polysaccharide monooxygenases". Journal of Chromatography. 2012.
Wood et al. "Preparation of crystalline, amorphous, and dyed cellulase substrates". J.Am Chem Soc., 2013.
Wiselogel et al. "Biomass feedstock resources and composition". Taylor & Francis, Washington, D.C.1996 pp. 105-1 18.
Ziessel et al. "An Artificial Light-Harvesting Array Constructed from Multiple Bodipy Dyes". J.Am Chem Soc. 2013.
Taglieber et al. "Light-driven biocatalytic oxidation and reduction reactions: Scope and limitations" ChemBioChem 2008, 9, 565-572.

* cited by examiner

LIGHT-DRIVEN SYSTEM AND METHODS FOR CHEMICAL MODIFICATION OF AN ORGANIC SUBSTRATE

FIELD OF INVENTION

The present disclosure relates to a light-driven system, which is able to chemically modify an organic substrate with high efficiency and in a cost-effective manner. Also provided are methods for chemically modifying an organic substrate using the present systems and methods for manufacturing such systems.

BACKGROUND OF INVENTION

Ever since the discovery of the basic mechanisms of photosynthesis, there have been numerous attempts to develop light-driven biochemical processes at an industrial scale by mimicking photosynthesis. In particular, processes for driving chemical modification of organic substrates are relevant. Such processes driven at an industrial scale require today high temperatures, catalysts and hydrogen and are thus costly.

The ability to carry out such biochemical reactions at ambient conditions using sunlight as energy source is expected to find numerous applications, for example in the field of energy-efficient and low-cost biofuel production based on substrates derived from e.g. agricultural waste. Efficient enzymatic conversion of crystalline polysaccharides, for example, remains to this date unfavorably inefficient.

Previous examples of light-driven enzymatic processes are hybrid systems of carbon monoxide dehydrogenase molecules with CdS nanocrystals for light-driven reduction of $CO_2$ (Chaudary et al., 2012) and a hydrogenase and $TiO_2$ nanoparticle for light-driven $H_2$ generation (Caputo et al., 2015). However, manufacturing such systems is complex and labor-intensive.

Thus, there is a need for light-driven systems that can be manufactured from abundant materials and that are capable to chemically modify an organic substrate with high efficiency. Such systems can be artificial.

SUMMARY OF INVENTION

The invention is as defined in the claims.

The present disclosure provides a light-driven system, which is able to chemically modify an organic substrate. The present systems can operate with a high efficiency and can be used to modify various substrates by using essentially no other external energy source than a light source such as sunlight. This light-driven system is based on abundant biological parts and can increase the catalytic activity of LPMOs up to 100-fold. This "reverse photosynthesis" system (Cannella et al., 2016) thus presents numerous applications in various technical fields where chemical modification of a substrate using light as sole energy source can be advantageous.

In a first aspect is provided a system for chemical modification of an organic substrate, said system comprising:
i. a light harvesting molecule;
ii. at least one catalyst; and
iii. a reductant and/or an electrochemical electrode.

In another aspect is provided a method for chemical modification of an organic substrate, said method comprising the steps of:
i. providing an organic substrate;
ii. contacting said organic substrate with a system comprising a light harvesting molecule, at least one catalyst and a reductant and/or an electrochemical electrode; and
iii. exposing said organic substrate contacted with said system to a light source,
whereby the organic substrate is chemically modified.

Also provided is a chemically modified organic substrate obtainable by the present methods.

Also provided is a method of manufacturing a system comprising a light harvesting molecule, at least one catalyst and a reductant and/or an electrochemical electrode, said method comprising the steps of providing a light harvesting molecule, at least one organic catalyst and a reductant and/or an electrochemical electrode.

The released oligosaccharides from PASO were measured by HPAEC chromatography showing non-oxidisoxidised and oxidisoxidised reaction products. Each chromatogram is average of three replicate experiments. a) Thy+Asc+LPMO+PASC+Sun: Thylakoids, ascorbic acid and LPMO with PASC in sunlight for 3 hours (150-200 µmol photons $s^{-1}$ $m^{-1}$). Control 1: Thy+Asc+LPMO+PASC+Dark: same conditions but in darkness. Control 2: Asc+LPMO+PASC+Sun: same conditions but without thylakoids. b) Same experiments as in a) but with chlorophyllin (Chl) as pigment. Peak annotations of native oligosaccharides (grey) were done using the pure compounds as standard: $Glc_2$, cellobiose; $Glc_3$, cellotriose; $Glc_4$, cellotetraose; $Glc_5$, cellopentaose; $Glc_6$, cellohexaose; $Glc_7$, celloheptaose; oxidisoxidised oligosaccharides (black) were assigned by comparing with literature chromatograms performed with identical separation conditions as done by Westereng[32]: GlcGlc1A, cellobionic acid; $Glc_2$Glc1A, cellotrionic acid; $Glc_3$Glc1A, cellotetraonic acid; $Glc_4$Glc1A, cellopentaoinic acid; $Glc_5$Glc1A, cellohexaoinic acid; $Glc_6$Glc1A, celloeptaonic acid; $Glc_7$Glc1A, cellooctaonic acid. On the y axis is reported the intensity of the signal in nC (nano Coulomb) without further adjustments. c) PASC oxidation with LPMO (TtAA9E), chlorophyllin, and ascorbic acid in response to blue, green, red light (150 µmol photons $s^{-1}$ $m^{-1}$) and sunlight (150-200 µmol photons $s^{-1}$ $m^{-1}$). Oxidation was measured with HPAEC quantifying the gluconic acid (oxidation of the C1 position at the pyranose ring). Asc: PASC and ascorbic acid in sunlight (black bar). No LPMO: PASC, chlorophyllin, and ascorbic acid in sunlight. d) Chlorophyllin, ascorbic acid, LPMO and PASC incubation was run for two cycles of darkness for 2 hours and sunlight for 5 min, or always in darkness (4 h10 min), black line with diamonds and green light with square, respectively. Negative control experiment missing LPMO was run in parallel with the darkness/sunlight cycles. The percentage of oxidisoxidised cellulose was measured by quantification of gluconic acid formed (C1 oxidation).

Figure 6:
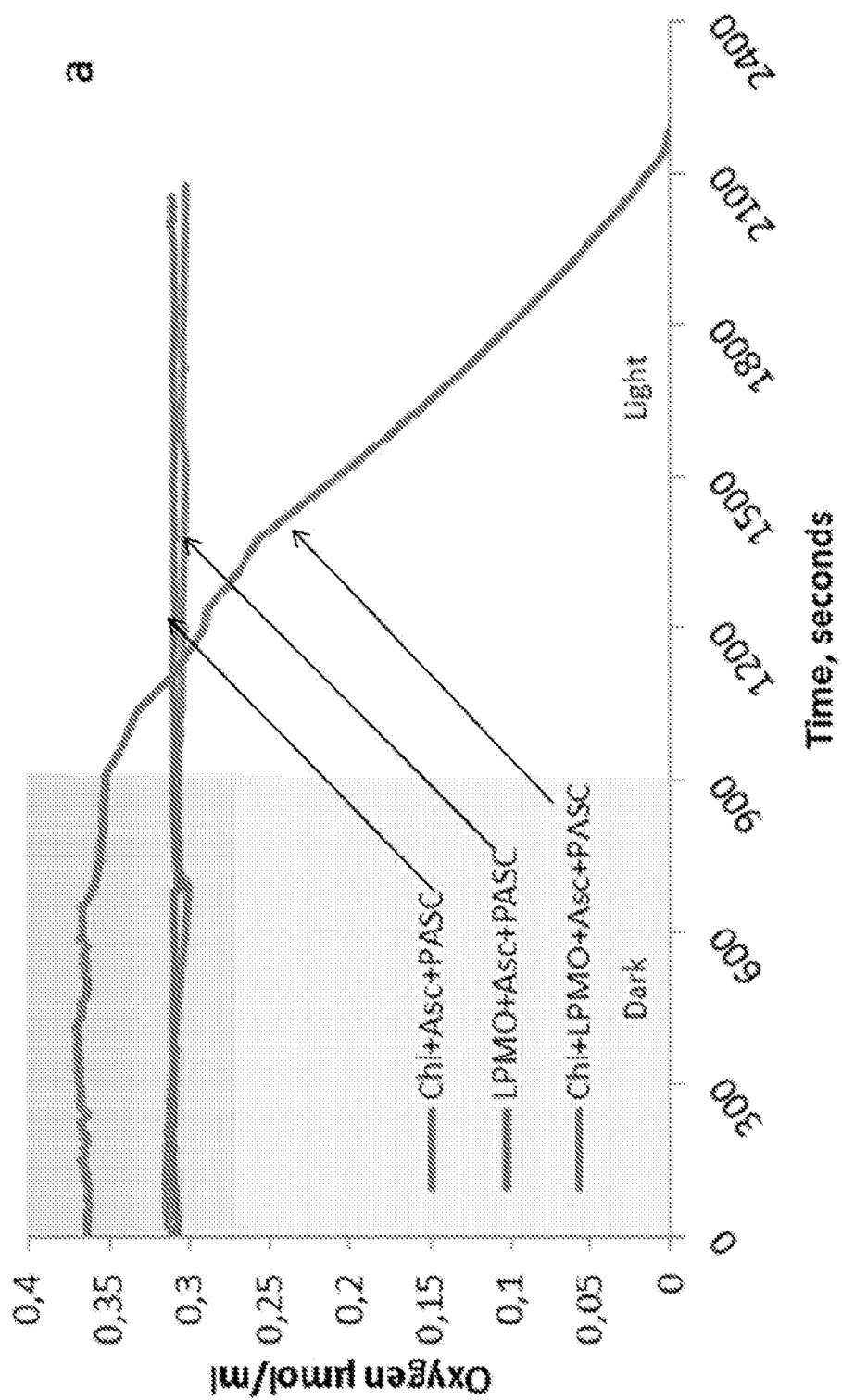
Figure 6:
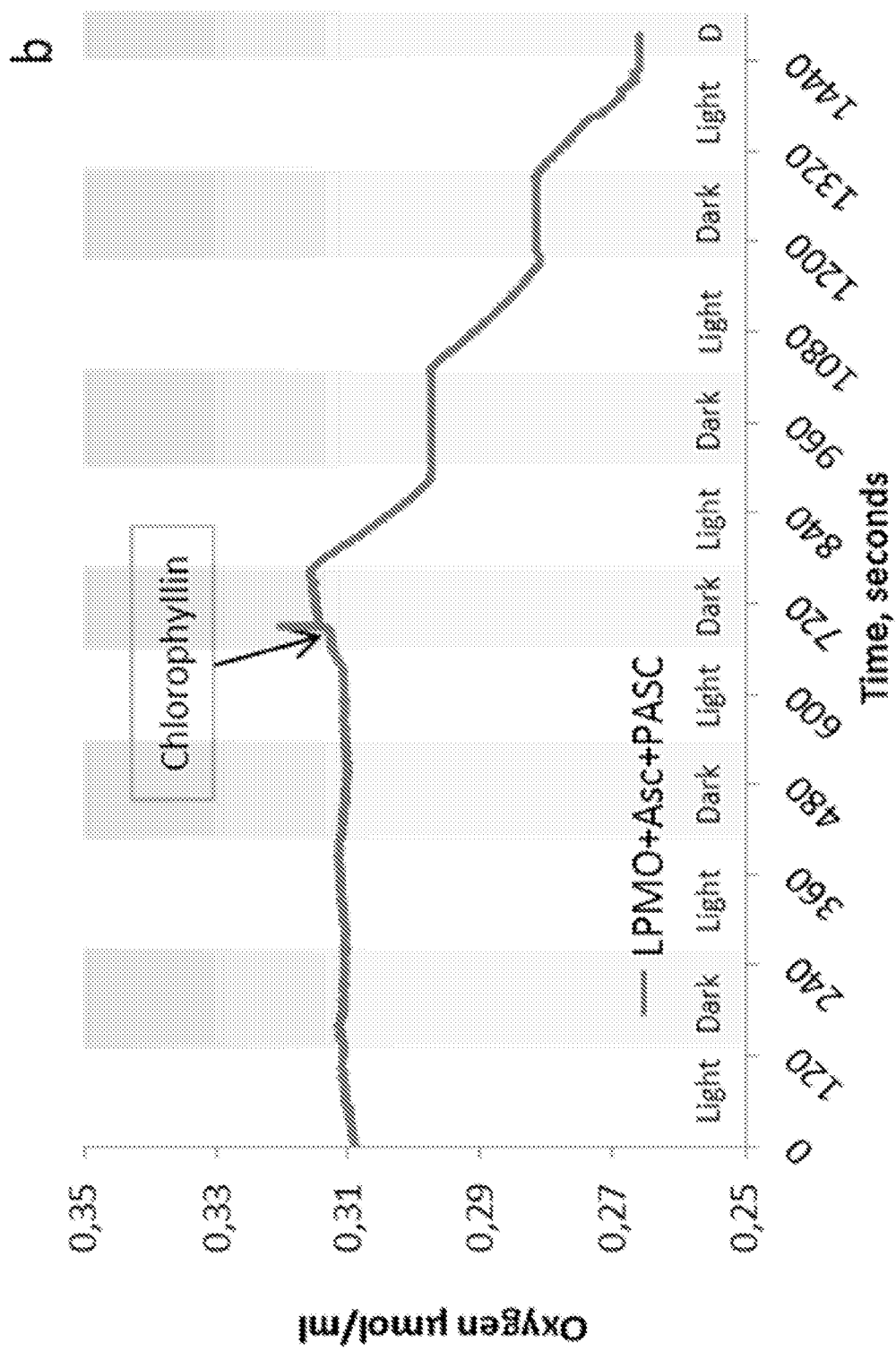

FIG. 6: Oxygen consumption during PASC oxidation in light or darkness.

a) Oxygen consumption with different combinations of the photosystem: the two almost horizontal lines show: i) chlorophyllin, ascorbic acid and PASC (without *T. terrestris* LPMO) and ii) *T. terrestris* LPMO, ascorbic acid and PASC; the third line shows the whole photosystem with chlorophyllin, ascorbic acid, *T. terrestris* LPMO and PASC. Light is turned on at 900 seconds. b) Alternating cycles of light and darkness: at the beginning of the incubation only *T. terrestris* LPMO, ascorbic acid and PASC are present, then chlorophyllin is added after 700 sec.

Figure 7:
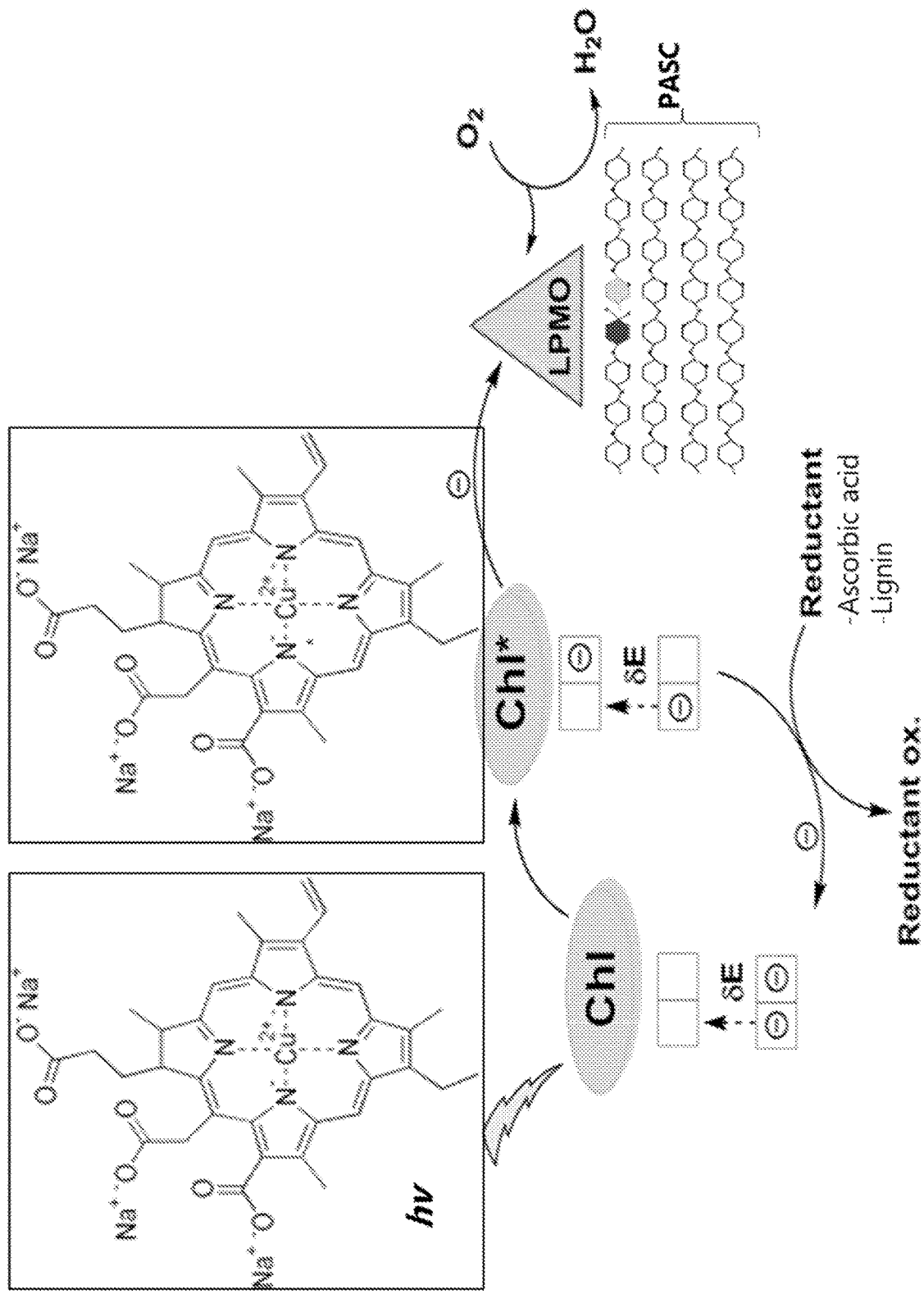

FIG. 7: Proposed mechanism for light-induced electron transfer to LPMO.

Light excites the pigment, which in its excited state transfers an electron to the LPMO enzyme. The excited electron reduces the copper in the LPMO active site, which then activates oxygen and oxidisoxidises the polysaccharide. The oxidisoxidised pigment returns to its ground state by acquisition of an electron from a nearby reductant such as ascorbic acid or lignin. During the monooxygenase reaction of LPMO dioxygen is split, and one oxygen atom is incorporated into the substrate, and the other is reduced to water. The oxidation of a PASC cellulose chain is highlighted by a dark grey monomer of glucose getting oxidisoxidised in the C1 position which will end being an aldonic acid oligosaccharide, whereas the light grey monomer will be released in form of non-oxidisoxidised oligosaccharide.

Figure 8:
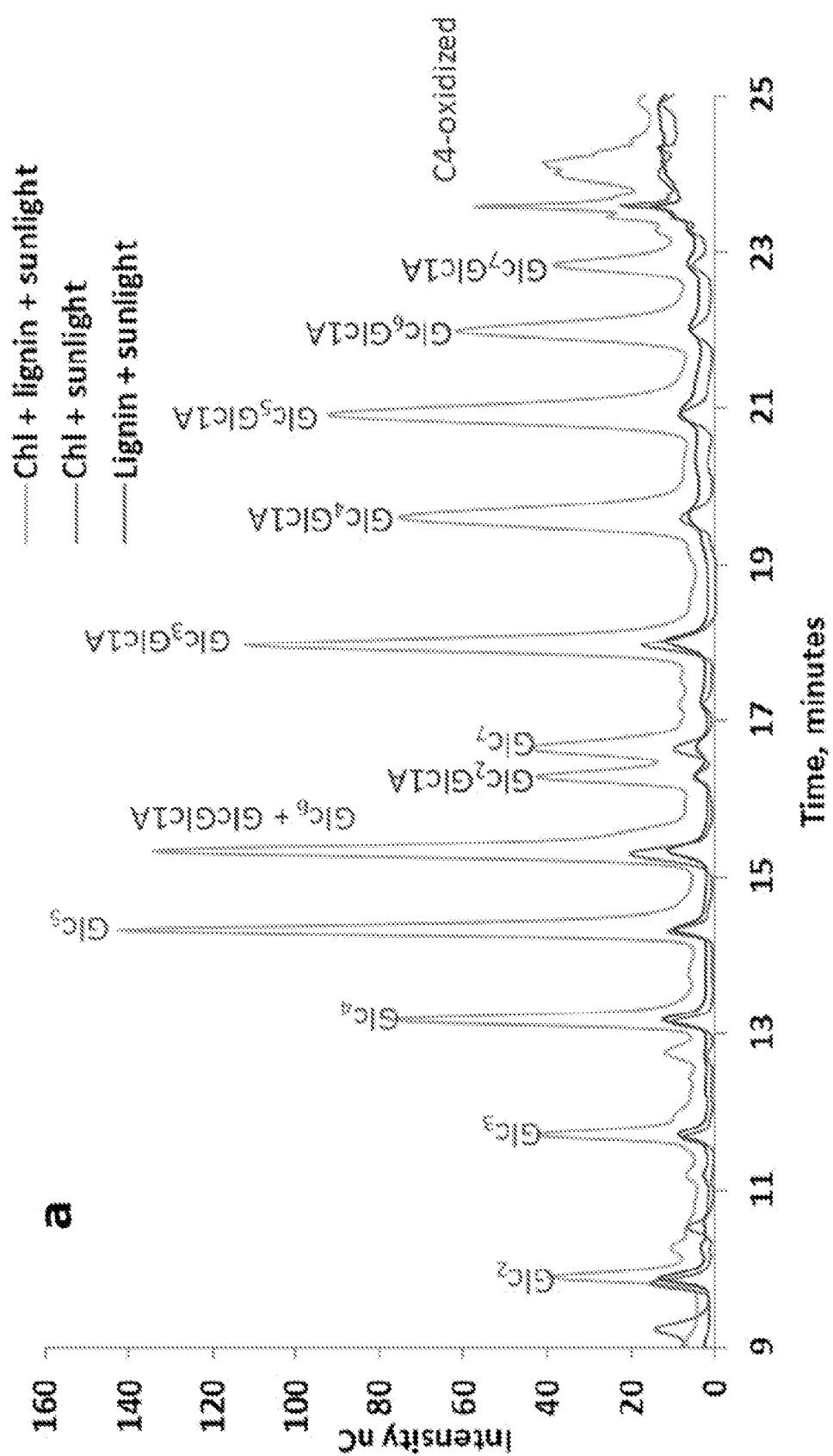
Figure 8:
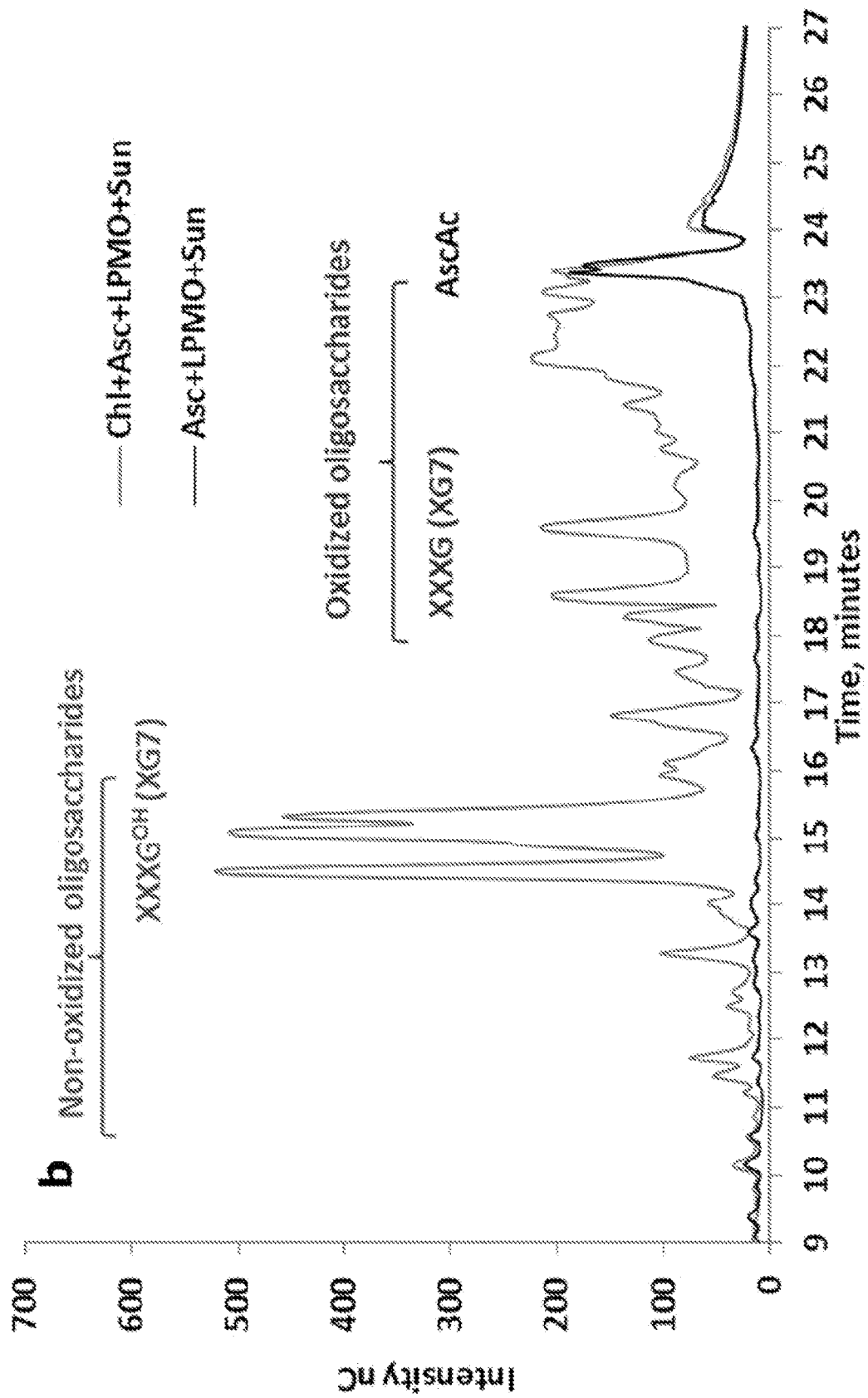

FIG. 8: HPAEC analysis of light-induced oxidation with *T. terrestris* LPMO (TtLPMO9E): lignin as reductant, and xylogucan as substrate.

a) Lignin as reductant: LPMO oxidative activity on cellulose (PASO) when incubated with chlorophyllin and organosolv lignin as reductant in 3 hours of sunlight. Controls with only chlorophyllin or organosolv lignin in sunlight are included. Each chromatogram is the average of three replicate experiments. b) Xyloglucan as substrate: LPMO oxidative activity on xyloglucan (1% w/w) when incubated with chlorophyllin and ascorbic acid and exposed to 3 hours of sunlight. Pronounced is the presence of oxidisoxidised species detectable from minute 17 to 24. A control experiment with LPMO and ascorbic acid shows no degradation of the xyloglucan. The xyloglucan is a heteropolymer of xylose, glucose, galactose and arabinose. The division of peaks in oxidisoxidised and non-oxidisoxidised is derived from the model heptamer xylooligosaccharide XXXG$^{OH}$ in its reduced form made of 4 units of glucose of which 3 are substituted with 1 xylose, XXXG is the same, but oxidisoxidised in the reducing end of the last subunit in the glucan backbone. Peak annotations: $Glc_2$, cellobiose; $Glc_3$, cellotriose; $Glc_4$, cellotetraose; $Glc_5$, cellopentaose; $Glc_6$, cellohexaose; $Glc_7$, celloeptaose; GlcGlc1A, cellobionic acid; $Glc_2Glc1A$, cellotrionic acid; $Glc_3Glc1A$, cellotetraonic acid; $Glc_4Glc1A$, cellopentaoinic acid; $Glc_5Glc1A$, cellohexaoinic acid; $Glc_6Glc1A$, celloheptaonic acid; $Glc_7Glc1A$ cellooctaonic acid.

Figure 9:
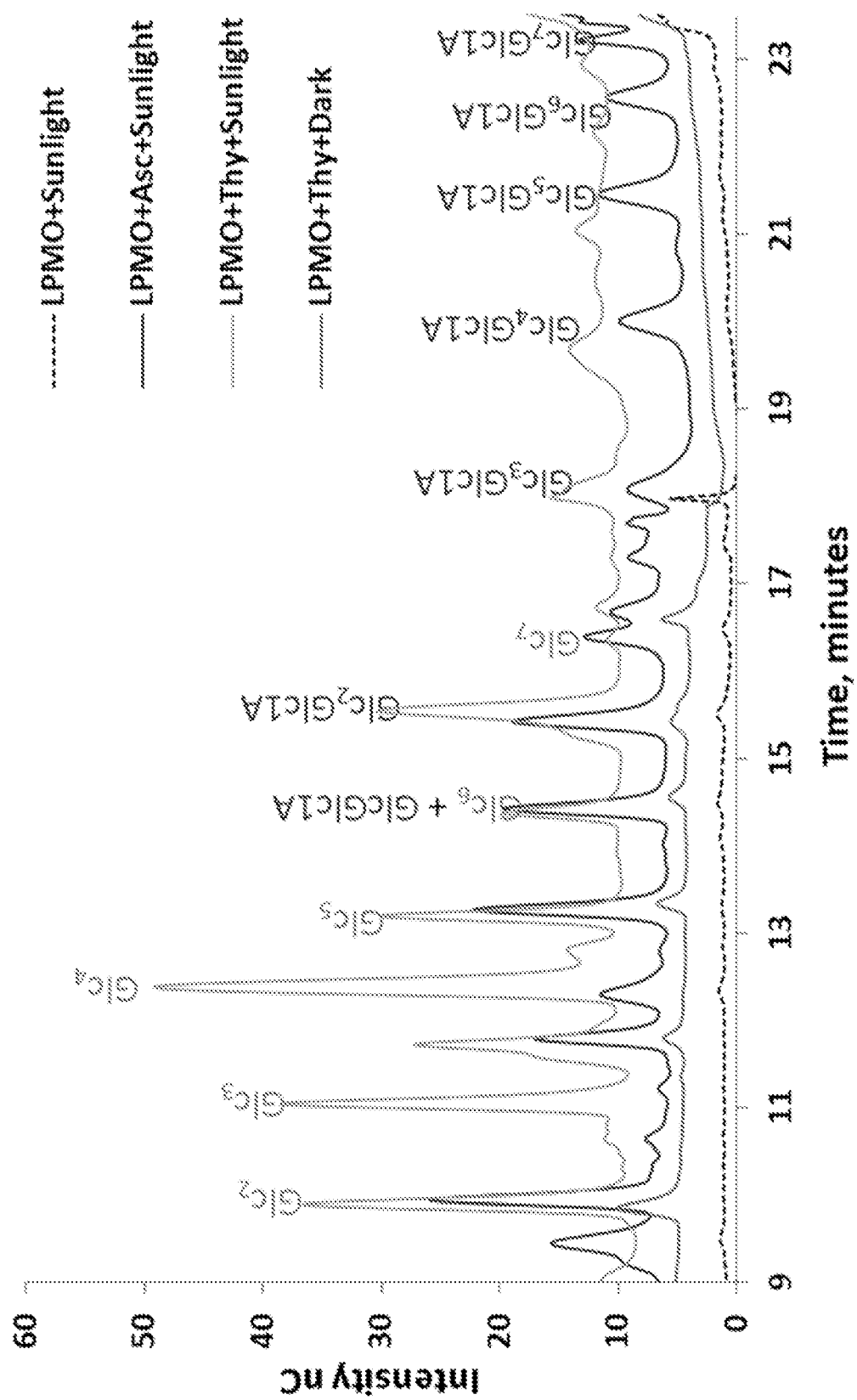

FIG. 9: Light induced cellulose oxidation by LPMO and a thylakoid suspension.

HPAEC chromatography of TtLPMO9E after incubation with a thylakoid suspension isolated from a cyanobacterium using sun light and green light (yellow and green chromatogram, respectively). The experiments were carried out with LPMO+thylakoid suspension only to measure the ability of the thylakoids to absorb light and consequently donate electrons to the LPMO. As control experiments cellulose (PASO) was incubated with ascorbic acid alone (black chromatogram), or TtLPMO9E alone (dotted chromatogram) and exposed to sunlight. Peak annotations: $Glc_2$, cellobiose; $Glc_3$, cellotriose; $Glc_4$, cellotetraose; $Glc_5$, cellopentaose; $Glc_6$, cellohexaose; $Glc_7$, celloheptaose; GlcGlc1A, cellobionic acid; $Glc_2Glc1A$, cellotrionic acid; $Glc_3Glc1A$, cellotetraonic acid; $Glc_4Glc1A$, cellopentaoinic acid; $Glc_5Glc1A$, cellohexaoinic acid; $Glc_6Glc1A$, celloeptaonic acid; $Glc_7Glc1A$, cellooctaonic acid The chromatograms shown report the measured intensity of the peaks without further adjustments, and are the average of three independent experiments.

Figure 10:
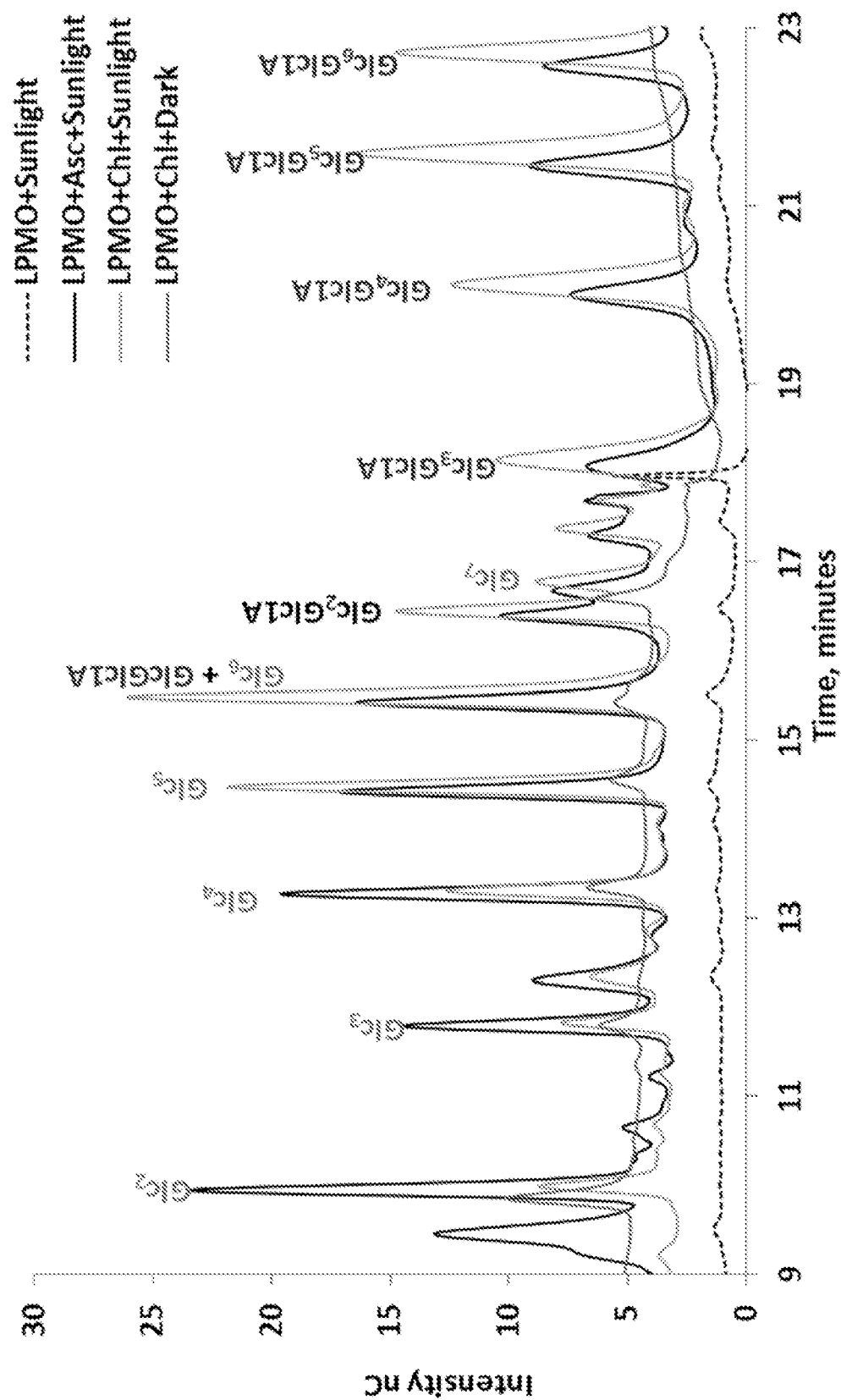

FIG. 10: Light induced cellulose oxidation by LPMO and the chlorophyll derivative chlorophyllin.

HPAEC chromatography of TtLPMO9E after incubation with chlorophyllin using sunlight or green light (grey and light grey chromatograms, respectively). The experiments were carried out with LPMO+chlorophyllin only and ascorbic acid to measure the ability of the chlorophyllin to absorb light and consequently donate electrons to the LPMO. Control experiments: PASC was incubated with ascorbic acid alone and exposed to sunlight (black chromatogram); TtLPMO9E was incubated with PASC alone and exposed to sunlight (dotted chromatogram). Peak annotations: $Glc_2$, cellobiose; $Glc_3$, cellotriose; $Glc_4$, cellotetraose; $Glc_5$, cellopentaose; $Glc_6$, cellohexaose; $Glc_7$, celloeptaose; GlcGlc1A, cellobionic acid; $Glc_2Glc1A$, cellotrionic acid; $Glc_3Glc1A$, cellotetraonic acid; $Glc_4Glc1A$, cellopentaoinic acid; $Glc_5Glc1A$, cellohexaoinic acid; $Glc_6Glc1A$, celloheptaonic acid; $Glc_7Glc1A$ cellooctaonic acid. The data presented in the chromatograms (here and elsewhere) display the measured intensity of the peaks without further adjustments, and are the average values of three replicate experiments.

Figure 11:
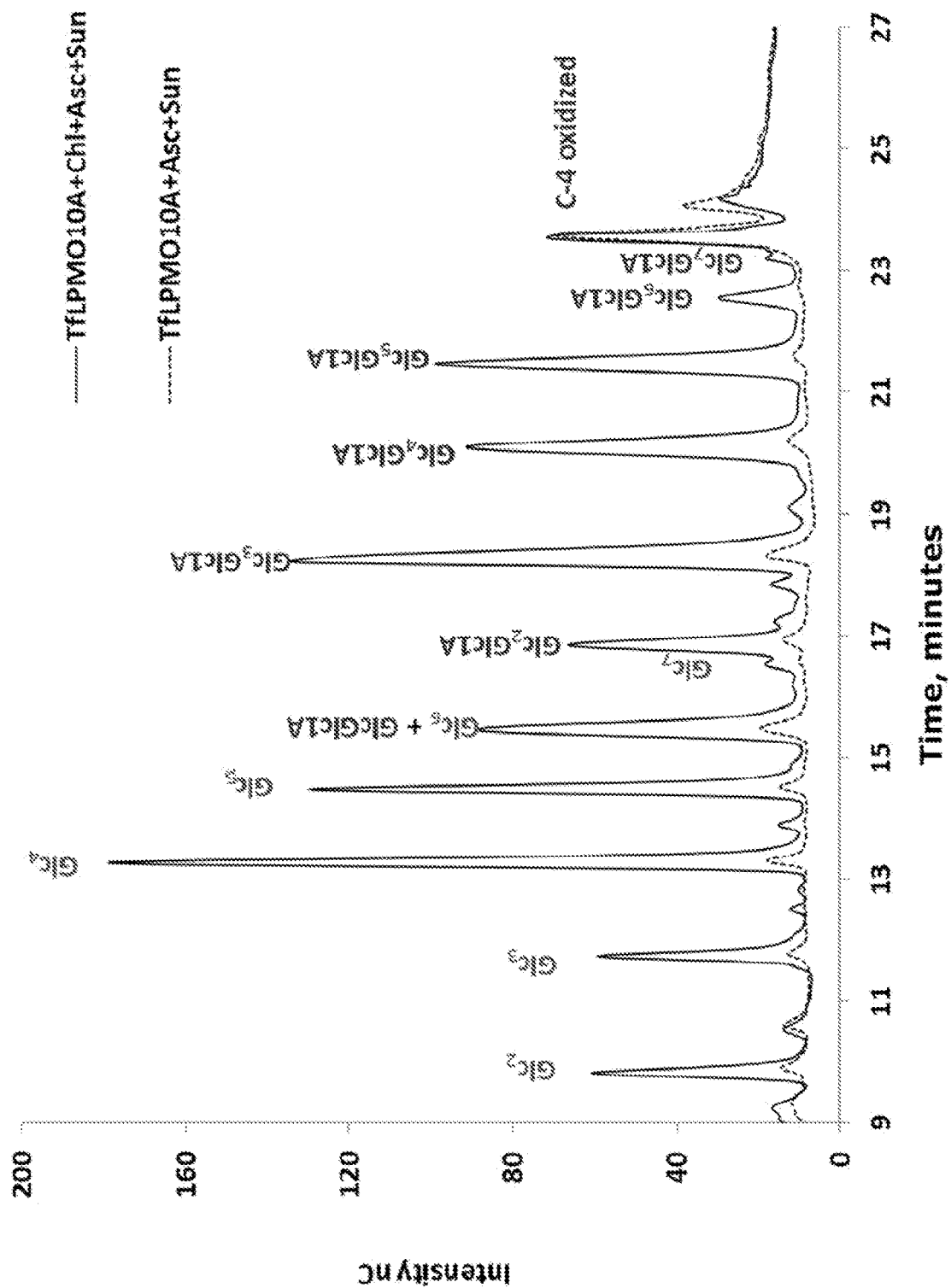

FIG. 11: Oxidation of cellulose using TfLPMO10A in combination with chlorophyllin, ascorbic acid and sunlight.

HPAEC chromatography of LPMO from *Thermobifida fusca* after incubation with the cellulose substrate PASC, chlorophyllin, ascorbic acid and sunlight (black chromatogram). As a control, the LPMO was incubated with PASC and ascorbic acid and exposed to sunlight (dotted line). A similar result was obtained in an experiment performed with a cyanobacterial thylakoid suspension instead of chlorophyllin (data not shown). Peak annotations: $Glc_2$, cellobiose; $Glc_3$, cellotriose; $Glc_4$, cellotetraose; $Glc_5$, cellopentaose; $Glc_6$, cellohexaose; $Glc_7$, celloeptaose; GlcGlc1A, cellobionic acid; $Glc_2Glc1A$, cellotrionic acid; $Glc_3Glc1A$, cellotetraonic acid; $Glc_4Glc1A$, cellopentaoinic acid; $Glc_5Glc1A$, cellohexaoinic acid; $Glc_6Glc1A$, celloheptaonic acid; $Glc_7Glc1A$ cellooctaonic acid; C-4 oxidisoxidised sugars: unseparated mixtures of 4-ketoaldose oligosaccharides.

Figure 12:
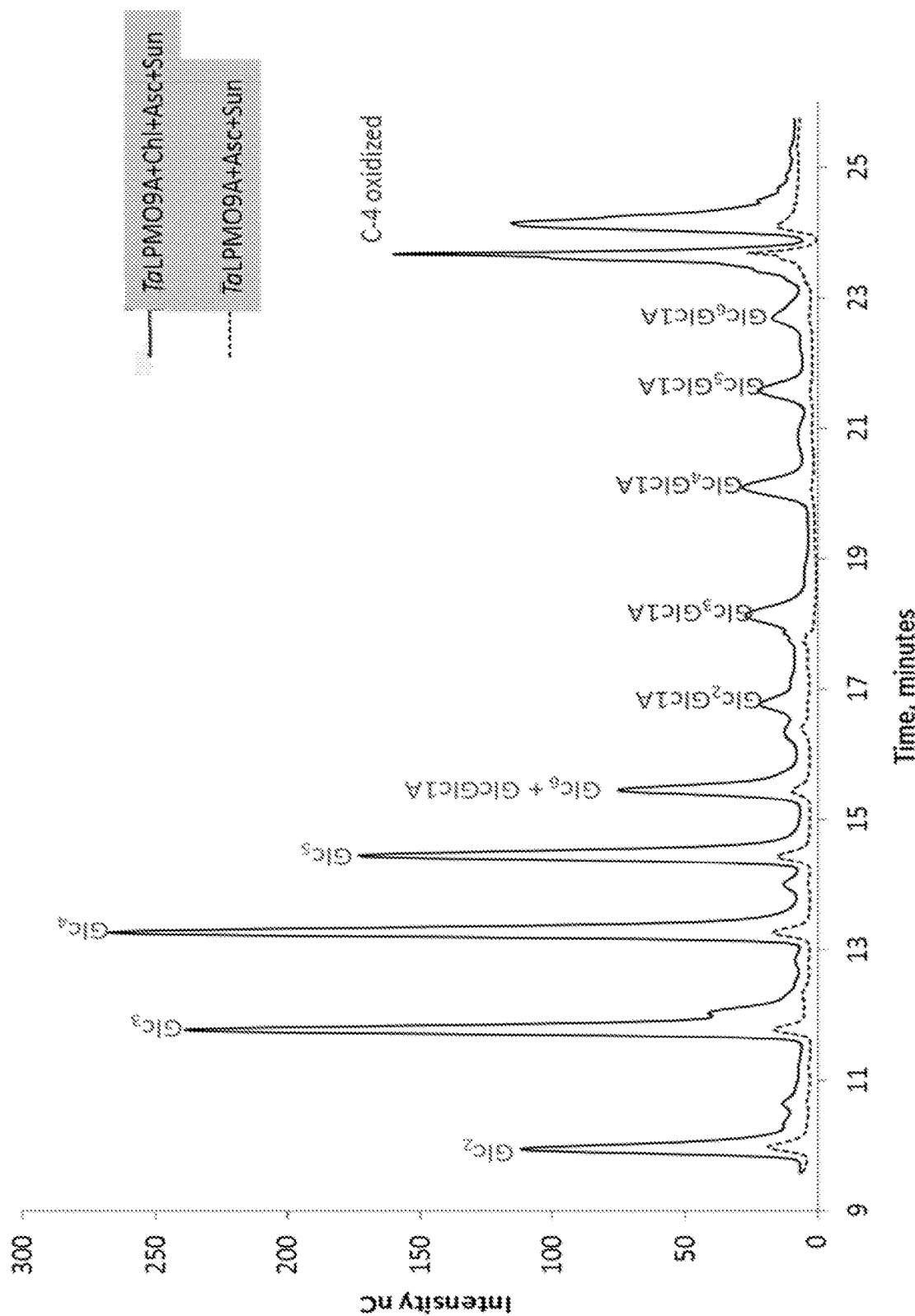

FIG. 12: Oxidation of cellulose using TaLPMO9A in combination with chlorophyllin, ascorbic acid and sunlight.

HPAEC chromatography of LPMO TaLPMO9A after incubation with PASO, the LIET system (chlorophyllin plus ascorbic acid) and sunlight (black chromatogram). A control experiment was performed without chlorophyllin (dotted chromatogram). Similar results were obtained using a thylakoid suspension instead of chlorophyllin (data not shown). Product identifications as in FIG. 11.

Figure 13:
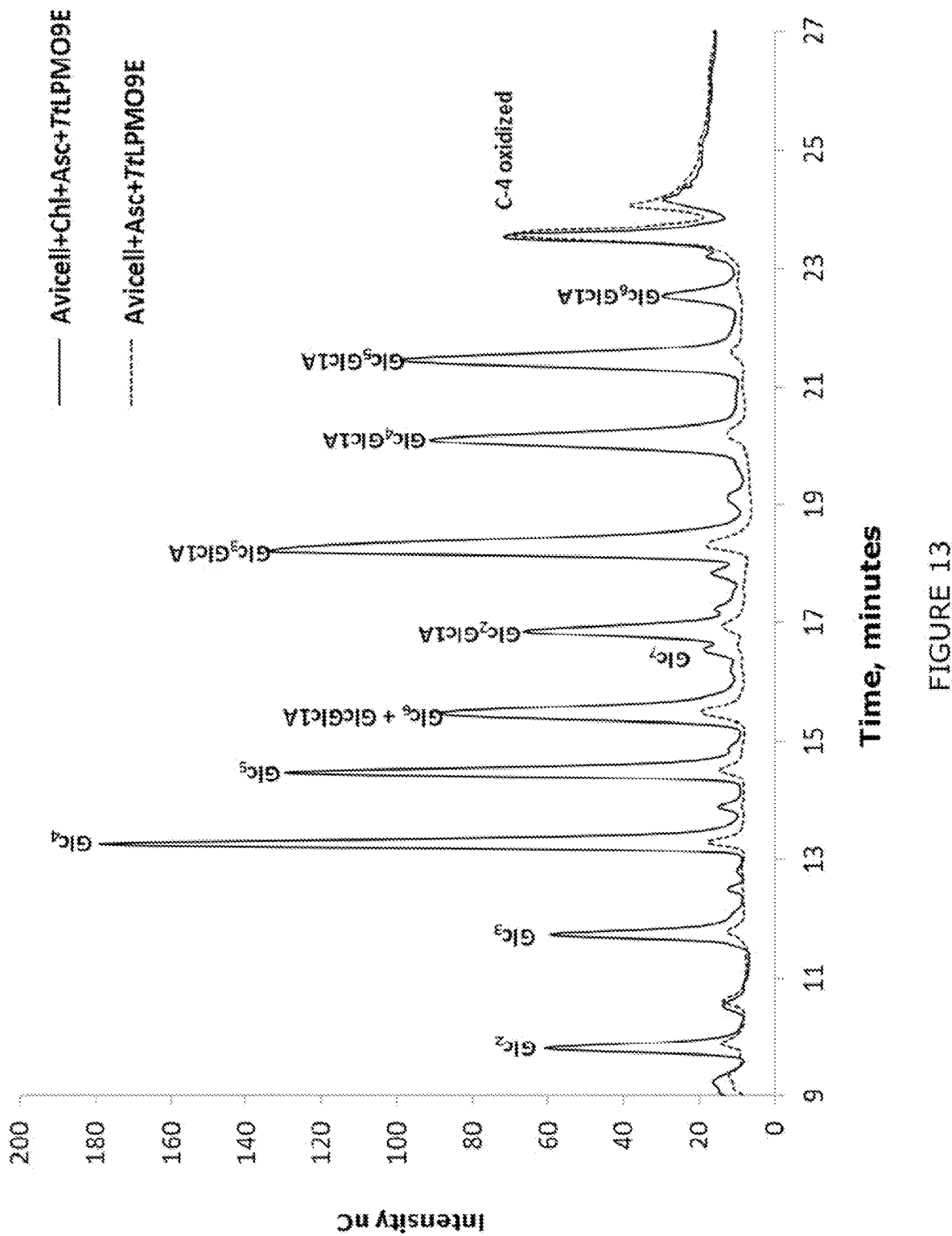

FIG. 13: Oxidation of crystalline cellulose using light Induced electron transfer.

TtLPMO9E, chlorophyllin and ascorbic acid with Avicell as substrate. HPAEC chromatography of LPMO TaLPMO9E after incubation with crystalline cellulose substrate (Avicell) and the light driven oxidative system (chlorophyllin plus ascorbic acid), exposed to sunlight (Black chromatogram). A control experiment was performed without chlorophyllin (dotted chromatogram). Product identifications as in FIG. 11.

Figure 14:
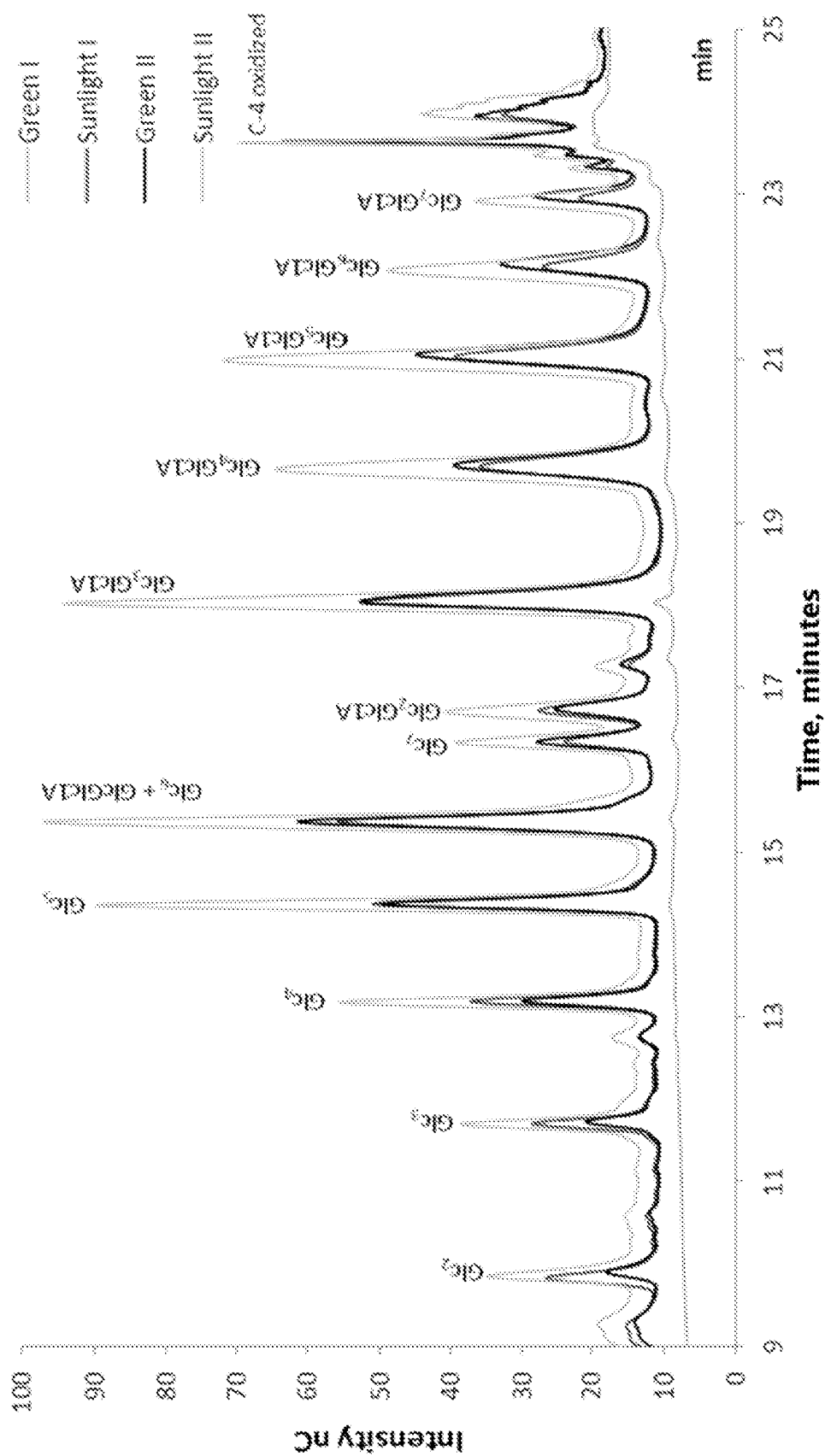

FIG. 14: Cellulose oxidation products from intermittent green light and sunshine.

Figure 5:
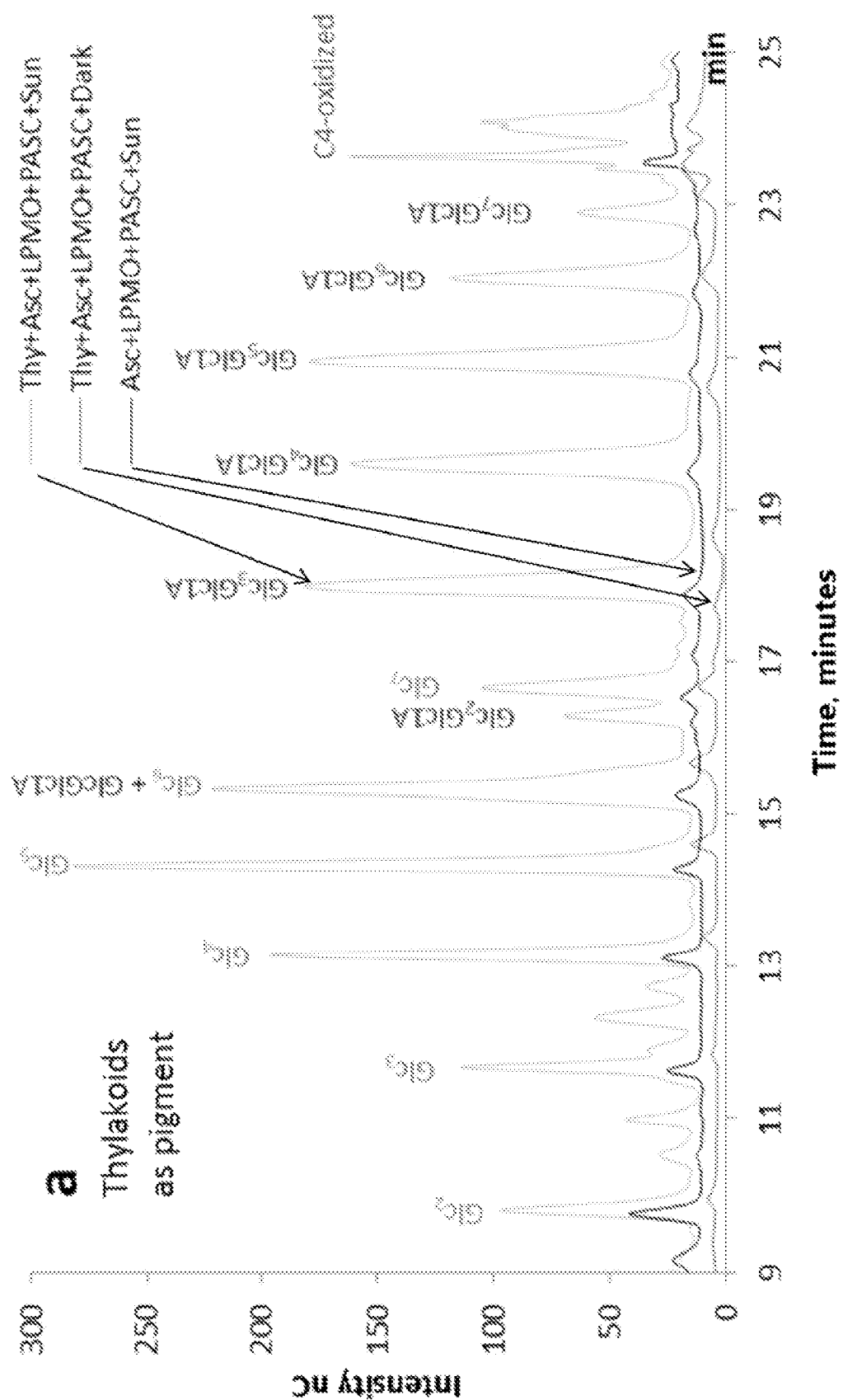
FIG. 5: Cellulose (PASC) oxidation by T. terrestris LPMO (TtLPMO9E) combined with light-induced electron transfer.
Figure 5:
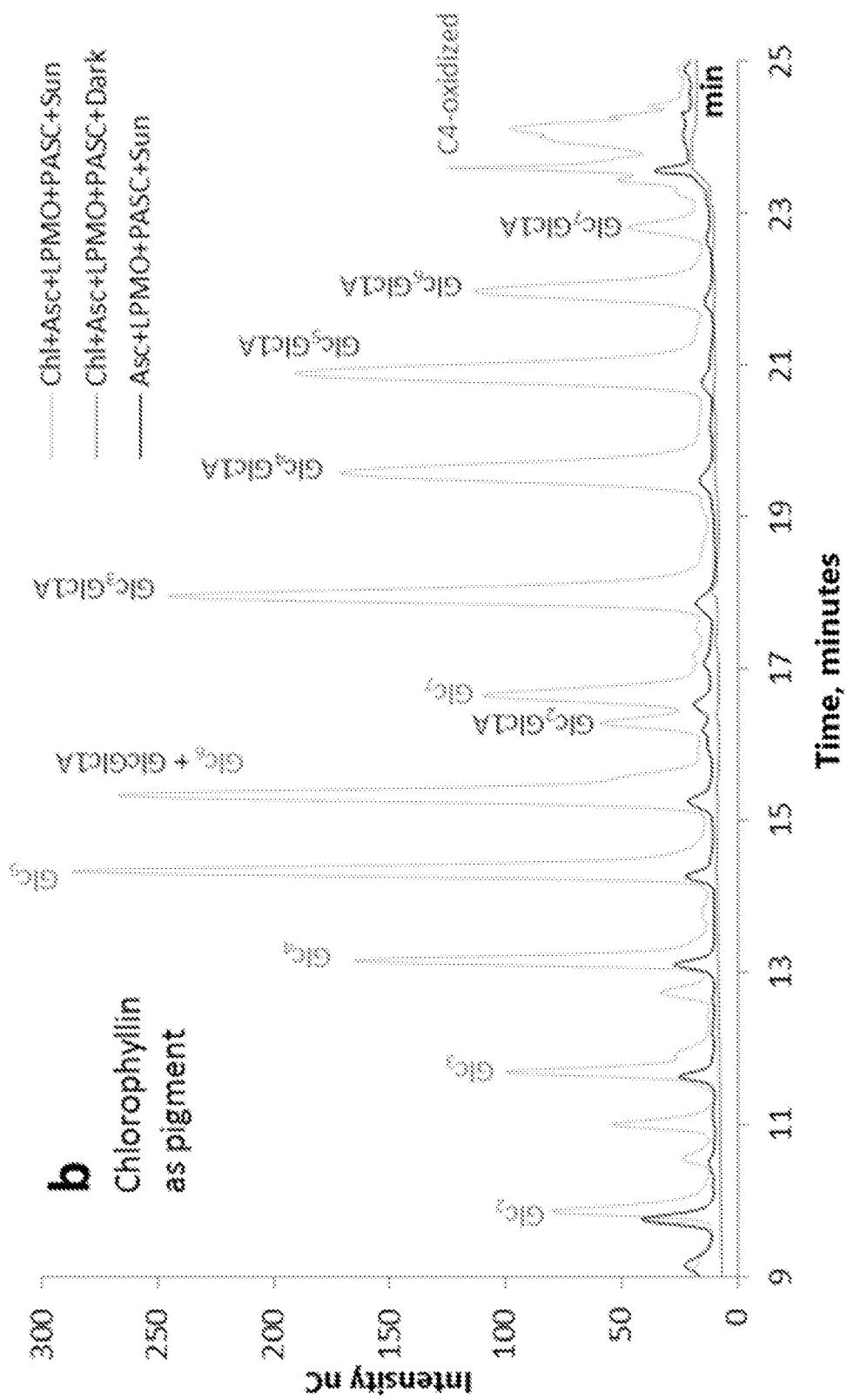
Figure 5:
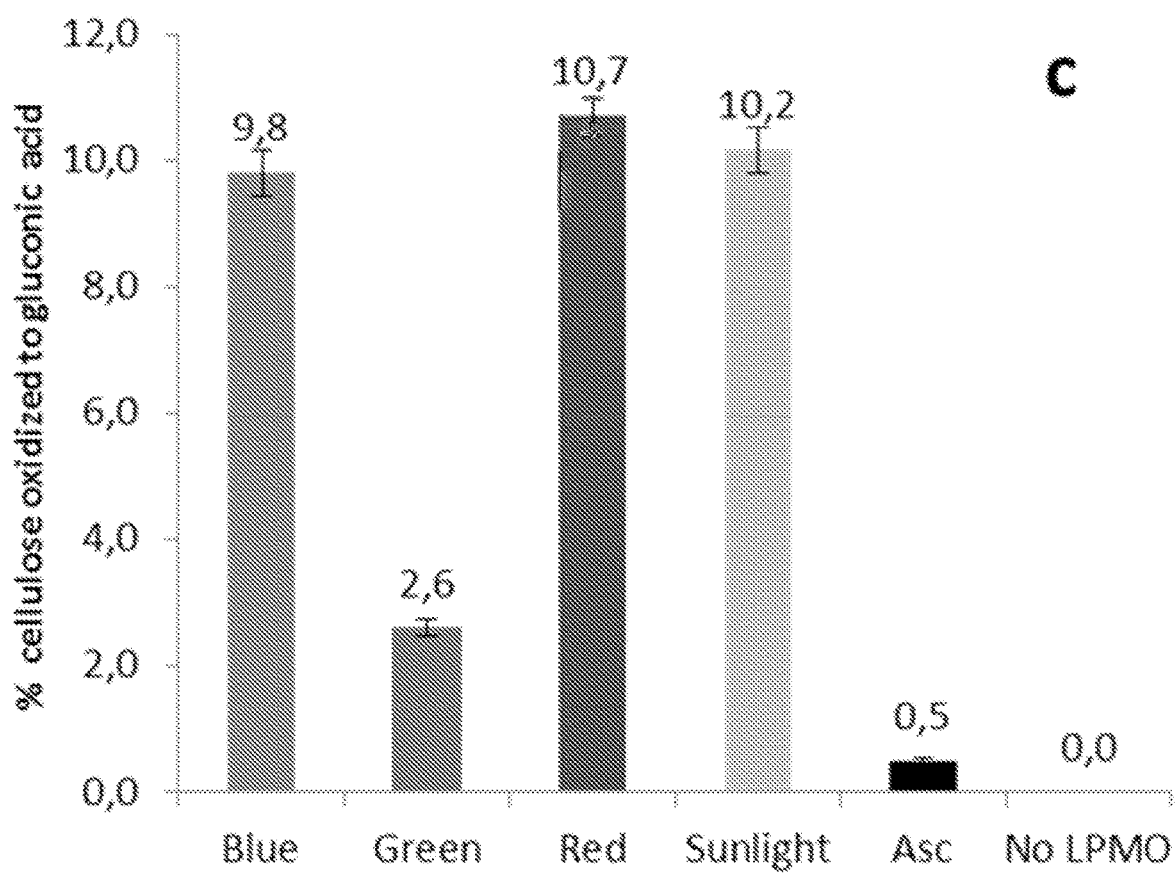
Figure 5:
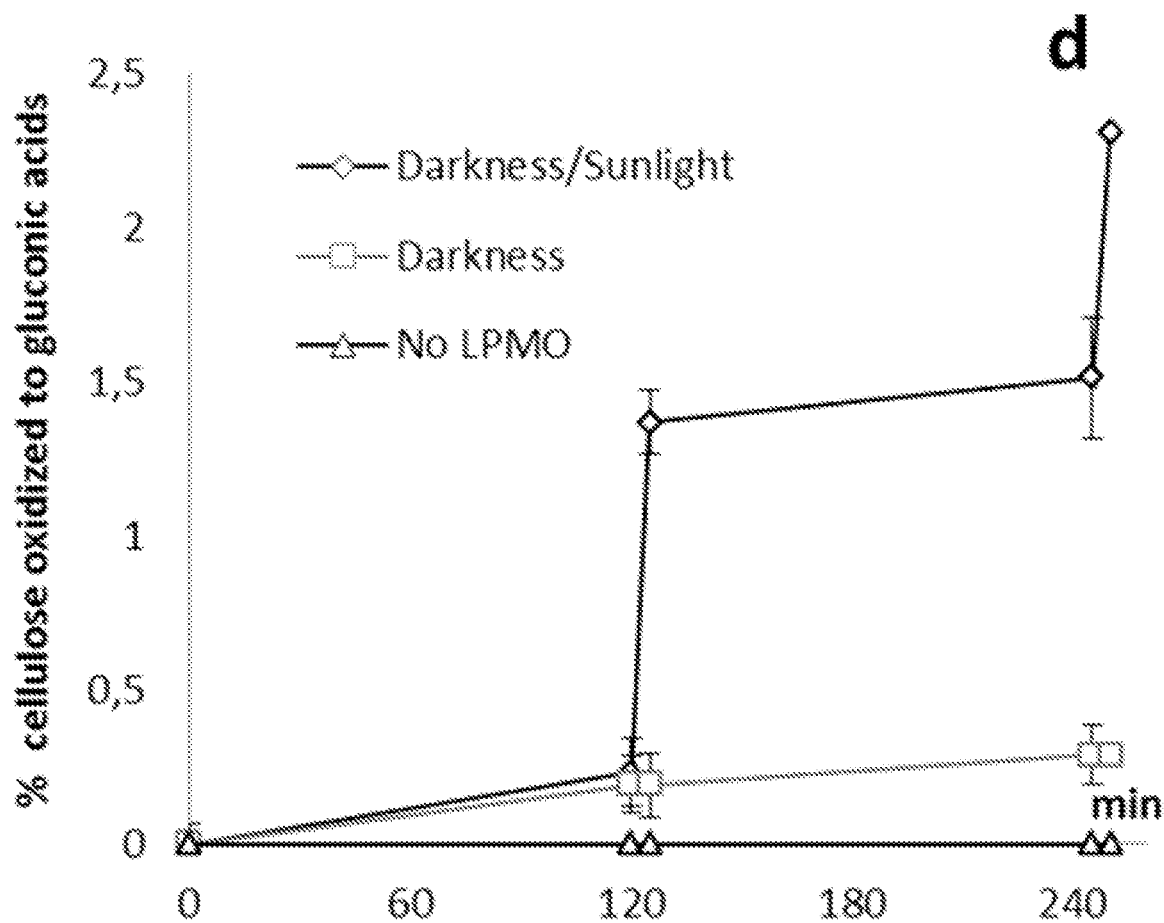

As supplement to FIG. 5D, HPAEC chromatography is shown. The TtLPMO9E was used for light induced oxidation in green light for 2 hours (green I, grey chromatogram), then the sample was exposed to sunlight for 5 minutes (Sunlight I, dark grey chromatogram). The sample was incubated again in green light (green II, black chromatogram) for 2 hours, and finally sunlight for 5 minutes (Sunlight II, light grey chromatogram). Product identifications as in FIG. 11.

Figure 15:
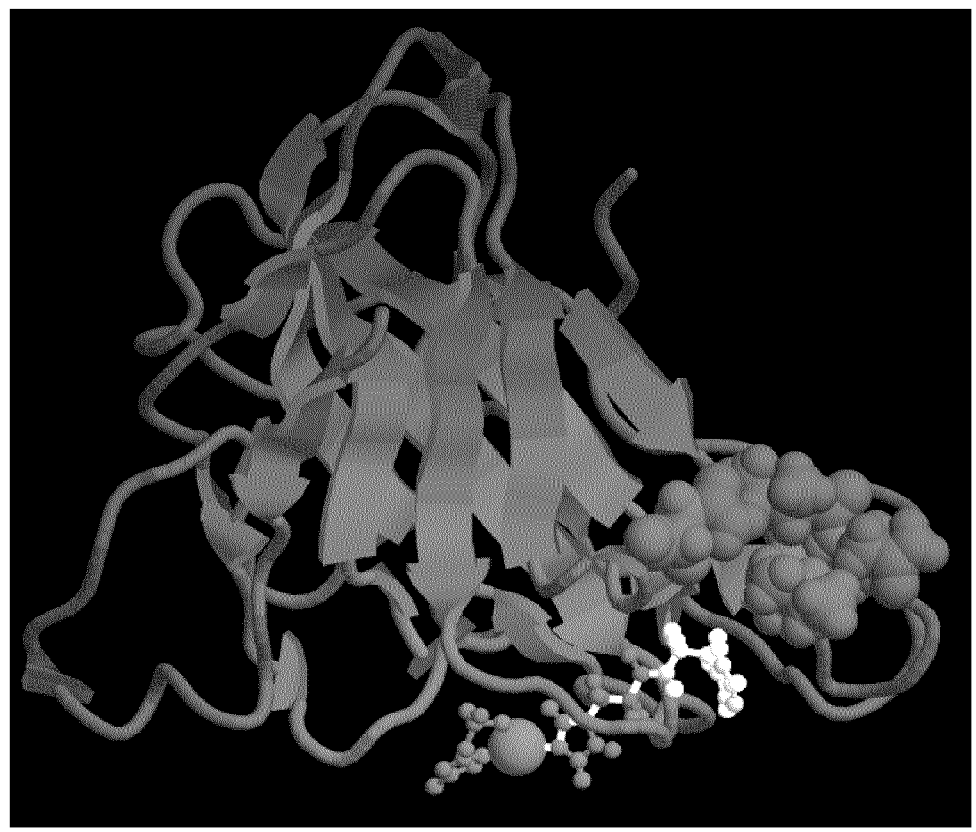

FIG. 15: Structure (PDB ID: 2YET) of *Thermoascus aurantiacus* LPMO (TtLPMO9E) showing a possible pathway to Cu(II).

The figure shows a possible pathway as a stick structure from His87 to Cu(II) through 12 covalent bonds equivalent to a tunneling length of 16.8 Å with a calculated pathway coupling decay value of $2.2 \cdot 10^{-3}$ from His87 NE2 to Cu(II). His87 is sitting on the side of LPMO and is thus free of the cellulose that is binding to LPMO during catalysis. A search conducted on other structures in the AA9 family revealed that similar good pathways could be found, They are all located very much in the same position, but with different ligands at the surface (2VTC:Tyr91; 2YET:His87; 4EIR:Lys85), 4EIS:Asp80, 4D7V:Lys84).

FIG. 16: Enzymatic hydrolysis of Avicel by CBHI combined with light-induced electron transfer.

(A): enzymatic hydrolysis of Avicel after 24 hours with CBHII combined with light induced electron transfer based on chlorophyllin. Bar A: CBHII+βGlucosidase enzymes (Enz control); bar B: CBHII+βGlucosidase enzymes, TtLPMO and ascorbic acid 1 mM (LPMO control). Bar C: CBHII+βGlucosidase enzymes, TtLPMO and ascorbic acid 1 mM and chlorophyllin. Experimental conditions: pH 5 0.1M citric acid buffer. LPMO dosage 10 mg/g substrate. CBH II dosage 10 mg/g substrate. Chlorophyllin 1.6 mM. Ascorbic acid 1 mM. Light intensity 170 µmoles per second. (B): Enzymatic hydrolysis of Avicel for 3 hours with CBHII combined with light-induced electron transfer and thylakoids. Bar A shows CBHII+βGlucosidase enzymes (Enz control); Bar B shows CBHII+βGlucosidase enzymes, thylakoids, TtLPMO and ascorbic acid; Bar C shows CBHII+βGlucosidase enzymes, thylakoids, TtLPMO, ascorbic acid and catalase. The control containing the Enz+LPMO+ascorbic acid is omitted here as it is already shown in panel A. Experimental conditions pH 5 0.1M citric acid buffer. LPMO dosage 10 mg/g substrate. CBH II dosage 10 mg/g substrate. Thylakoids 0.35 mg/ml. Ascorbic acid 1 mM. Light intensity 170 µmoles per second.

Figure 17:
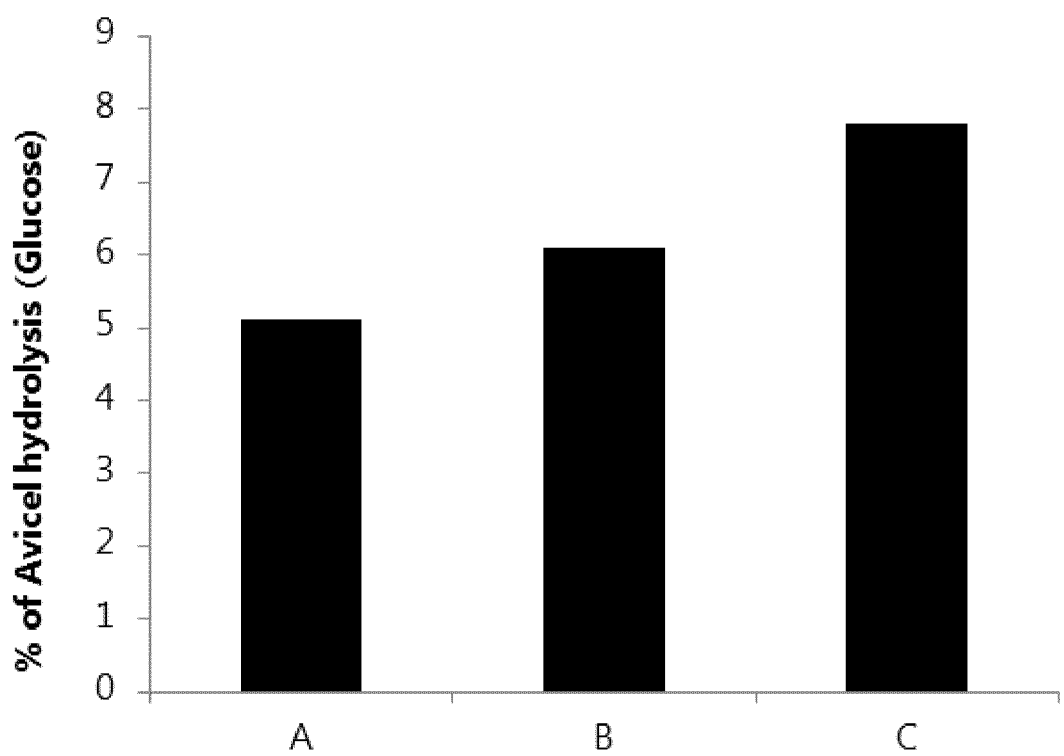

FIG. 17: Enzymatic hydrolysis of Avicel by CBHI combined with light-induced electron transfer using thylakoids.

Bar A shows CBHI+βGlucosidase enzymes (Enz control); Bar B shows CBHI+βGlucosidase enzymes, TtLPMO and ascorbic acid (LPMO control); Bar C shows CBHI+βGlucosidase enzymes, thylakoids, TtLPMO and ascorbic acid. Experimental conditions pH 5 0.1M citric acid buffer. LPMO dosage 10 mg/g substrate. CBH I dosage 10 mg/g substrate. Thylakoids 0.35 mg/ml. Ascorbic acid 1 mM. Light intensity 170 µmoles per second.

Figure 18:
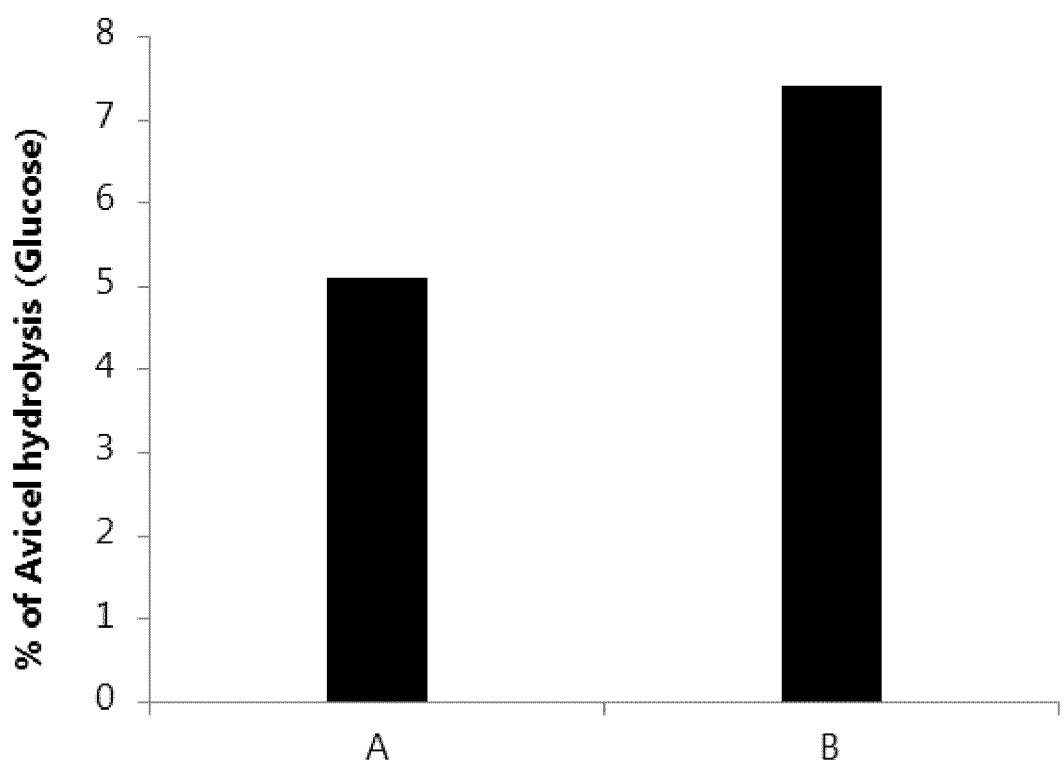

FIG. 18: Effect of varying light intensity.

The system contained monocomponent cellulase (CBH II) and betaglucosidase. Bar A: the reaction contains substrate, CBHII, betaglucosidase, TtLPMO9E, ascorbic acid, thylakoids exposed to blue and red light simultaneously at total intensity of 200 µmol per second. Bar B: the reaction contains substrate, CBHII, betaglucosidase, TtLPMO9E, ascorbic acid, thylakoids exposed to red light only at 170 µmol per second.

Figure 19:
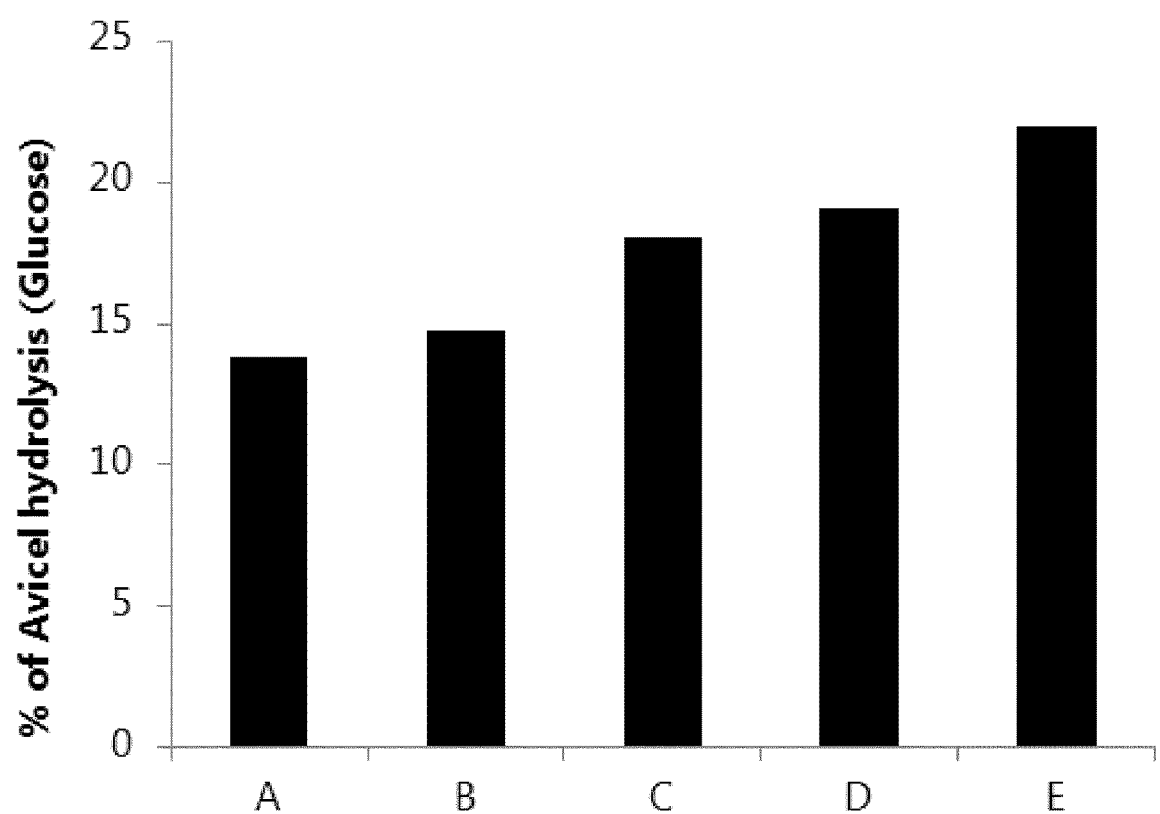

FIG. 19: Cellulose hydrolysis with a multicomponent cellulase enzyme cocktail.

Bar A shows Celluclast+βGlucosidase enzymes (Enz control); Bar B shows Celluclast+βGlucosidase supplemented with TtLPMO enzymes and ascorbic acid 1 mM (LPMO control); Bar C shows Celluclast+βGlucosidase, thylakoids, ascorbic acid 1 mM, and TtLPMO; Bar D shows Celluclast+βGlucosidase, thylakoids, ascorbic acid 2 mM, and TtLPMO D Bar E contains Celluclast+βGlucosidase, thylakoids, ascorbic acid 1 mM, and TaLPMO.

Figure 20:
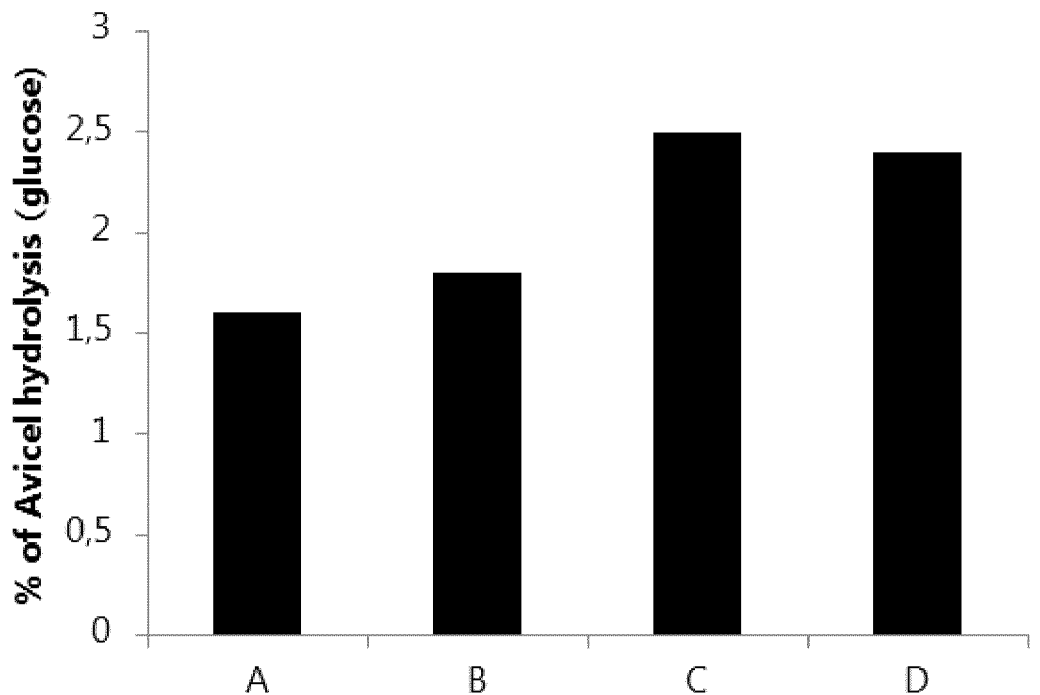
Figure 20:
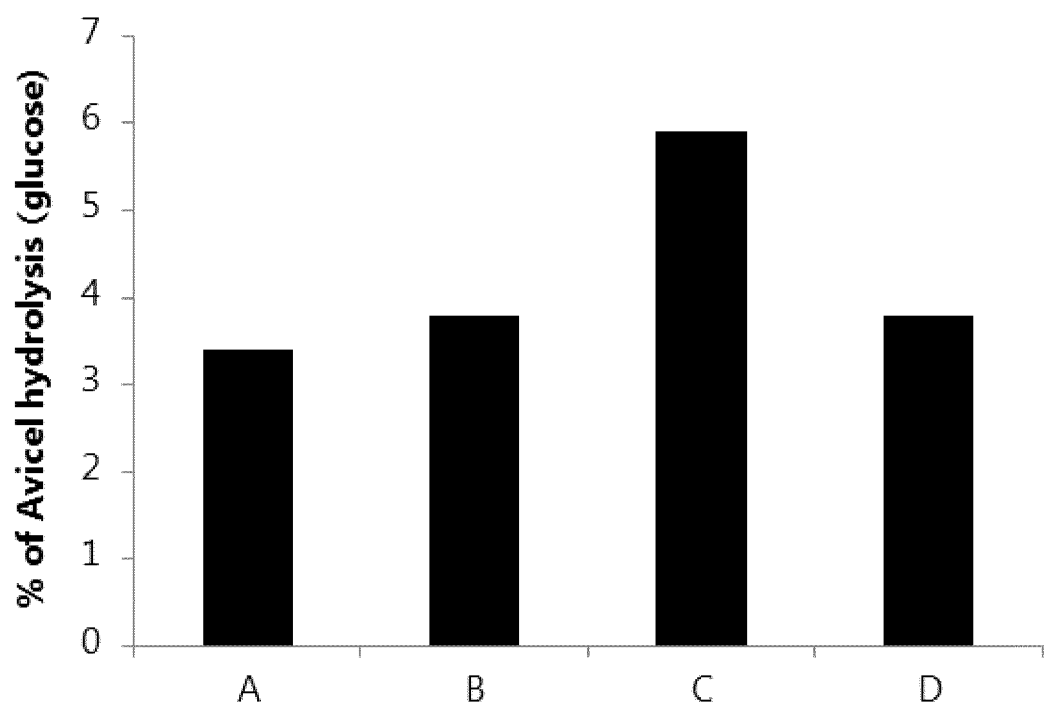

FIG. 20: Effect of intermittent light (10/50 sec on/off cycle).

Upper panel: 2 hours of incubation. Lower panel: 8 hours of incubation. Bar A: enzymatic cocktail and avicel substrate; bar B: enzymatic cocktail, TtLPMO, TaLPMO, ascorbic acid and avicel substrate; bar C: enzymatic cocktail, TtLPMO, TaLPMO, ascorbic acid, thylakoids and avicel substrate at intermittent light; bar D: enzymatic cocktail, TtLPMO, TaLPMO, ascorbic acid, thylakoids and avicel substrate at full light. Red light is used at 170 µmol per second.

Figure 21:
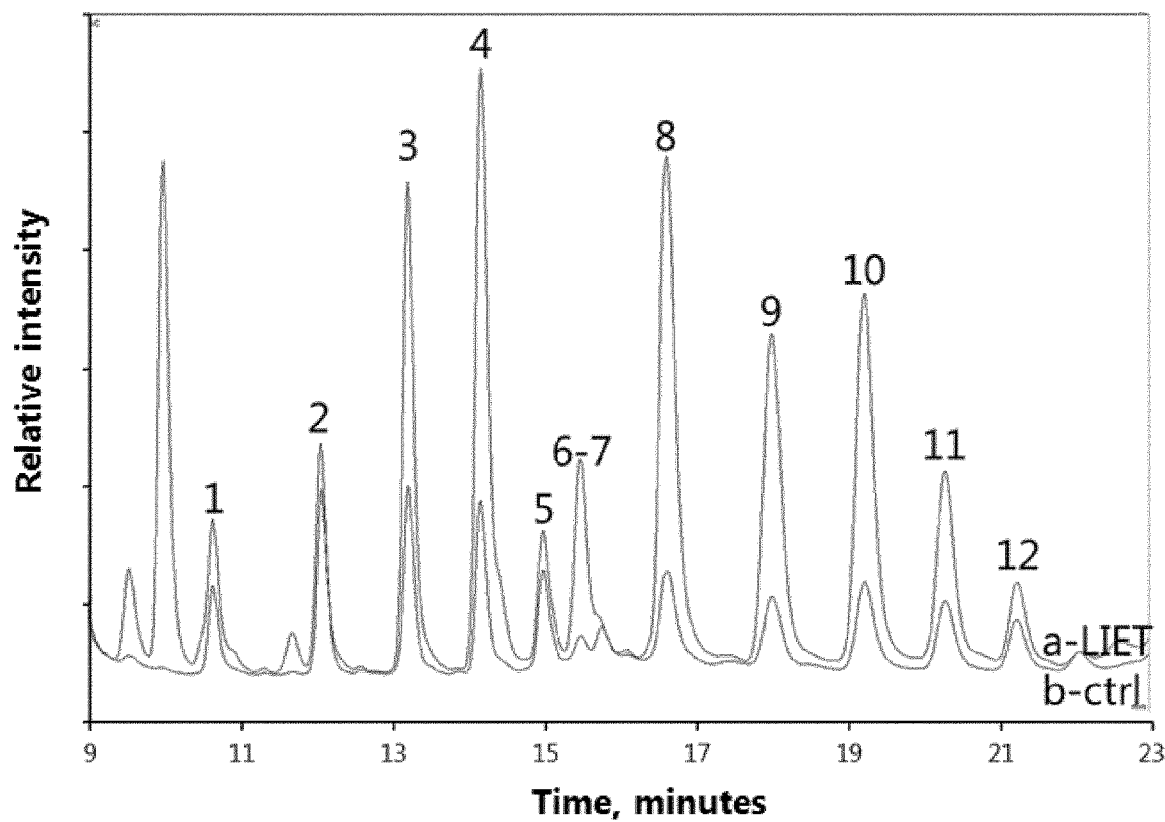

FIG. 21: Light-induced electron transfer on natural substrate: cotton.

Line a: light-induced electron transfer: sample containing chlorophyllin, ascorbic acid, TtLPMO, and cotton as substrate; line b: control sample containing ascorbic acid, TtLPMO, and cotton as substrate. Peak detection: 1 cellobiose; 2 cellotriose; cellotetraose; 4 cellopentaose; 5 cellohexaose and cellobionic acid; 6 cellotrionic acid; 7 celloeptaose; 8 cellotetraonic acid; 9 cellopentaonic acid; 10 cellohexaonic acid; 11 celloeptaonic; 12 cellooctaonic acid. Y axis: relative units (arbitrary). Red light is used at 170 µmol per second.

Figure 22A:
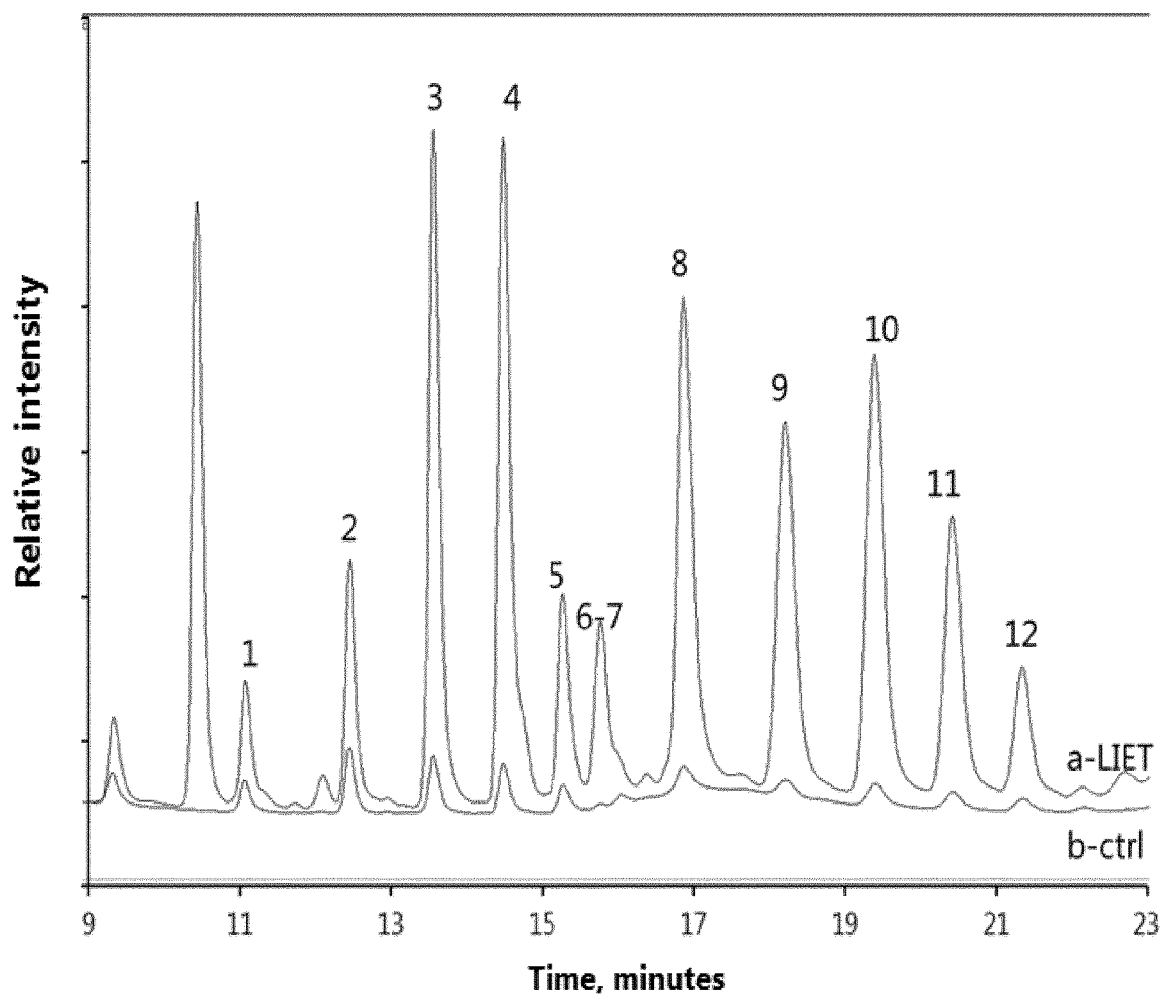

FIG. 22: Effect of different reducing agents for light-induced electron transfer.

(A) galllic acid as reducing agent (1 mM). Line a: light-induced electron transfer: sample containing chlorophyllin, gallic acid, TtLPMO, and PASO as substrate; line b: control sample containing gallic acid, TtLPMO, and cotton as substrate. Peak detection: 1 cellobiose; 2 cellotriose; cellotetraose; 4 cellopentaose; 5 cellohexaose and cellobionic acid; 6 cellotrionic acid; 7 celloeptaose; 8 cellotetraonic acid; 9 cellopentaonic acid; 10 cellohexaonic acid; 11 celloeptaonic; 12 cellooctaonic acid. (B) ferulic acid as reducing agent (1 mM). Line a: light-induced electron transfer: sample containing chlorophyllin, ferulic acid, TtLPMO, and PASO as substrate; line b: control sample containing ferulic acid, TtLPMO, and PASO as substrate. Peak detection: 1 cellobiose; 2 cellotriose; cellotetraose; 4 cellopentaose; 5 cellohexaose and cellobionic acid; 6 cellotrionic acid; 7 celloeptaose; 8 cellotetraonic acid; 9 cellopentaonic acid; 10 cellohexaonic acid; 11 celloeptaonic; 12 cellooctaonic acid. Y axis: relative units (arbitrary). Red light is used at 170 µmol per second.

Figure 23:
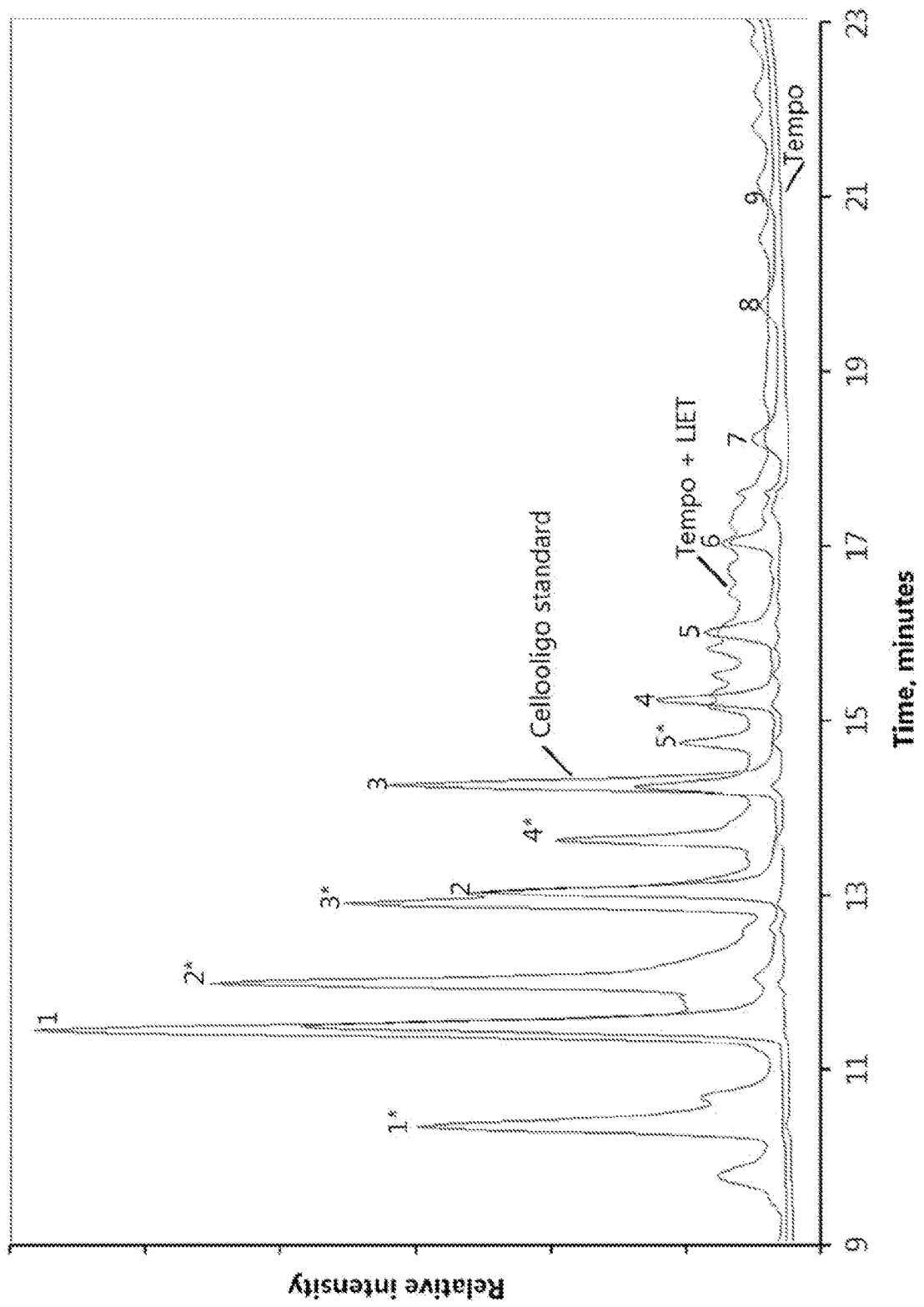

FIG. 23: Combining light induced electron transfer with other methods for cellulose oxidation—combination with TEMPO oxidation. Peak detection: 1 cellobiose; 2 cellotriose; cellotetraose; 4 cellopentaose; 5 cellohexaose and cellobionic acid; 6 cellotrionic acid; 7 celloeptaose; 8 cellotetraonic acid; 9 cellopentaonic acid Peaks with * are native oligosaccharides with one random C6 oxidisoxidised monomer along the oligochain. Peaks from minute 14 to 17 are aldonic oligosaccharides with one random C6 or C2 oxidisoxidised monomer along the oligochain. Peaks from minute 20 to 23 are aldonic oligosaccharides with one random C6 or C2 oxidisoxidised monomer along the oligochain. Y axis: relative units (arbitrary). Red light is used at 170 μmol per second.

DEFINITIONS

Coordination compound: coordination compounds are molecules that possess a metal centre that is bound to ligands (atoms, ions, or molecules that donate electrons to the metal). These complexes can be neutral or charged. When the complex is charged, it can be stabilized by neighboring counter-ions.

Eutectic solvent: A eutectic solvent, also termed deep eutectic solvent or DES, is a type of ionic liquid with special properties composed of a mixture which forms a eutectic system with a melting point much lower than either of the individual components. A eutectic solvent is a type of ionic liquid and may involve intra-solvent hydrogen bonding. Eutectic solvents are typically considered well suited for applications involving enzymes.

Ionic liquid: the term refers to a salt in a liquid state. Ionic liquids can also be termed liquid electrolytes, ionic melts, ionic fluids, fused salts, liquid salts, or ionic glasses. An ionic liquid thus is a liquid comprising or consisting of ions and short-lived ion pairs.

Light-harvesting complex or molecule: The term refers to a complex or a molecule which is capable of absorbing photons which excite an electron inside the molecule to a higher energy level. When the excited molecule or complex has a nearby neighbour molecule, the excitation energy may also be transferred to the neighbour molecule through electromagnetic interactions or quantum mechanical effects such as tunneling.

Metalloprotein is a generic term for a protein that contains a metal ion cofactor.

Reductant: The term 'reductant' is herein used interchangeably with the terms 'reducing agent' and 'reducer' and refers to a compound that loses (or "donates") an electron to another chemical species (an electron recipient or oxidisoxidising agent) in a redox chemical reaction.

Soluble: the term shall herein be used interchangeably with the term 'water-soluble', unless otherwise specified. A compound is water-soluble if it can dissolve in water.

DETAILED DESCRIPTION OF THE INVENTION

Surprisingly, the present disclosure provides a light-driven system, which is able to chemically modify an organic substrate. The present system can operate with a high efficiency and can be used to modify various substrates by using essentially no other external energy source than a light source such as sunlight. The present systems are also very stable. It is envisioned that the use of the present methods and systems may revolutionise industrial biochemical processes, since their efficiency is significantly increased compared to known systems and methods. Production costs are thus expected to decrease accordingly. The present systems and methods are also expected to provide efficient means for converting natural resources to energy in the form of energy carriers or chemicals in an efficient and cost-effective manner, for example for converting agricultural waste to biofuel, or for applications in the food industry.

In a first aspect, the invention relates to a system for chemical modification of an organic substrate, said system comprising:
   i. a light harvesting molecule;
   ii. at least one catalyst; and
   iii. a reductant and/or an electrochemical electrode.

Also provided herein is a method for chemical modification of an organic substrate, said method comprising the steps of:
   i. providing an organic substrate;
   ii. contacting said organic substrate with a system comprising a light harvesting molecule, a catalyst and a reductant; and
   iii. exposing said organic substrate contacted with said system to a light source,
whereby the organic substrate is chemically modified.

Also provided is a chemically modified organic substrate obtainable by the method disclosed herein.

Also provided is a method of manufacturing a system comprising a light harvesting molecule, at least one catalyst and a reductant and/or an electrochemical electrode, said method comprising the steps of providing a light harvesting molecule, at least one catalyst and a reductant and/or an electrochemical electrode.

Also provided is a method for producing a product, said method comprising the steps of:
   i. providing an organic substrate;
   ii. contacting said organic substrate with a system comprising a light harvesting molecule, at least one catalyst and a reductant and/or an electrochemical electrode; and
   iii. exposing said organic substrate contacted with said system to a light source,
whereby the organic substrate is chemically modified to obtain said product.

System for Chemical Modification of an Organic Substrate

The inventors have developed a system, which can chemically modify an organic substrate. The system may be light-driven, i.e. requiring only light as an external energy source. In some embodiments, the system is not naturally occurring. The system may thus be artificial or synthetic, i.e. assembled. Preferably, the chemical modification which the present system can carry out is an oxidation.

The systems disclosed herein comprise a light harvesting molecule, at least one catalyst, a reductant and/or an electrochemical electrode. In some embodiments, the system is aqueous. In some embodiments, the system is non-aqueous. The present systems can be used in methods for chemical modification of a substrate, as detailed in the section with the same title. It will be understood that the nature of the substrate and/or the nature of the chemical modification to be performed may influence how the system is designed. Thus, each of the parameters of the system described herein may be optimised by routine procedures in order to find the optimal system with the highest efficacy for each desired chemical modification of a given substrate.

The system preferably has a positive redox potential relative to a standard hydrogen electrode. Thus in some embodiments, the system has a redox potential relative to a standard hydrogen electrode of at least 0.1 V, such as at least 0.2 V, such as at least 0.3 V, such as at least 0.4 V, such as at least 0.5 V, such as at least 0.6 V, such as at least 0.7 V, such as at least 0.8 V, such as at least 0.9 V or more.

The system may comprise $10^{-8}$ to 50% w/v of a light-harvesting molecule as detailed below. In some embodiments, the system comprises $10^{-8}$ to 50% w/v of a light-harvesting molecule as detailed below, such as $10^{-7}$ to 40% w/v, such as $10^{-6}$ to 30% w/v, such as $10^{-5}$ to 25% w/v, such as $10^{-4}$ to 20% w/v, such as $10^{-3}$ to 15% w/v, such as $10^{-2}$ to 10% w/v, such as 0.1% to 5% w/v, such as about 1% of a light-harvesting molecule, where v is the volume of the organic substrate to be chemically modified. In other embodiments, the system comprises $10^{-8}$ to 10% w/v of a light-harvesting molecule as detailed below, such as $10^{-7}$ to 7.5% w/v, such as $10^{-6}$ to 5% w/v, such as $10^{-5}$ to 4% w/v, such as $10^{-4}$ to 3% w/v, such as $10^{-3}$ to 2% w/v, such as $10^{-2}$ to 1% w/v, such as 0.1% to 1% w/v of a light-harvesting molecule, where v is the volume of the organic substrate to be chemically modified. While the system may require only small amounts of light-harvesting molecule, such as 1% w/v or less, in some embodiments the light-harvesting molecule may be comprised in the reductant, as detailed below, and may thus be present at higher concentration, such as 30% or 35% w/v or more in the case of lignin for example.

The system may comprise $10^{-8}$ to 1% w/v of a catalyst as detailed below, such as $10^{-7}$ to 1% w/v, such as $10^{-6}$ to 1% w/v, such as $10^{-5}$ to 1% w/v, such as $10^{-4}$ to 1% w/v, such as $10^{-3}$ to 1% w/v catalyst, where v is the volume of the organic substrate to be chemically modified.

The system may comprise $10^{-7}$ to 2% w/w of a soluble reductant as detailed below, such as $10^{-6}$ to 2% w/w, such as $10^{-4}$ to 2% w/w, such as $10^{-3}$ to 2% w/w soluble reductant, expressed relative to the weight of the organic substrate.

The system may comprise $10^{-3}$ to 40% w/w of an insoluble reductant as detailed below, such as $10^{-3}$ to 39% w/w, such as $10^{-2}$ to 38% w/w, such as $10^{-2}$ to 37% w/w, such as $10^{-1}$ to 37% w/w, such as $10^{-1}$ to 35% w/w, expressed relative to the weight of the organic substrate.

The system may comprise 1 to 50% w/v of an organic substrate as detailed below, such as 1 to 45% w/v, such as 1 to 40% w/v, such as 1 to 35% w/v, such as 1 to 30% w/v organic substrate, where v is the total volume.

Organic Substrate

The systems disclosed herein are suitable for chemically modifying an organic substrate. Accordingly, in some embodiments, the system further comprises an organic substrate to be chemically modified. The present systems and methods can be used for chemical modification of organic substrates derived from waste.

The systems disclosed herein are particularly advantageous for the chemical modification of agricultural waste products. Thus in some embodiments, the system comprises at least one organic substrate, where the at least one organic substrate is an agricultural waste product, such as derived from rice, wheat, cotton, sugar cane, beet, corn, fruits, plant pulp, fruit pulp, such as bagasse or beet pulp; a product or waste product from the forestry industry such as hardwood, softwood, woodchips, wood pulp or sawdust; a waste stream or a waste product such as a household waste stream or waste product or an industrial waste stream or waste product such as empty fruit bunches, waste paper, packaging materials or a chitin-rich waste stream derived from shellfish processing. Food production processes, such as juice production, to name one example, yield great amounts of waste products in the form of e.g. starch, fruit pulp and fruit shells. A recent development in society is the emergence of waste legislation for preventing the generation of waste and developing biosustainable processes. Waste management includes the internal recycling of production waste and the re-use of waste products for identical or other purposes. Food production waste products are but one example of organic substrates which can advantageously be modified by the present methods into compounds that can be used in other processes.

Cellulose is the most abundant organic molecule on earth and offers a renewable and seemingly inexhaustible feedstock for the production of fuels and chemicals. Chitin is a common constituent of fungal cell walls, shells of crustaceans and exoskeletons of insects. It is the second most abundant polymer in nature and each year more than one billion tons of chitin is produced in the biosphere, mainly by insects, fungi, crustaceans and other marine organisms. Chitin is abundantly available as a by-product from aquaculture, one of the fastest growing bioproduction industries on earth.

The conversion of cellulose- and hemicellulose-containing feedstock into ethanol has the advantages of the ready availability of large amounts of feedstock, the desirability of avoiding burning or land filling the materials and the cleanness of the ethanol fuel. Wood, agricultural residues, herbaceous crops and municipal solid wastes have been considered as feedstock for ethanol production. These materials primarily consist of cellulose, hemicellulose and the non-polysaccharide lignin. Once the cellulose and hemicellulose are converted to hexoses and pentoses, the sugars can easily be fermented by microorganisms such as yeast or modified yeast—for C5-fermentation into ethanol. Methods for converting hexoses and pentoses to ethanol are known in the art.

By way of example, the cellulose- or hemicellulose-containing material may be stems, leaves, hulls, husks and cobs of plants or leaves, branches and wood of trees. The cellulose-containing material can be, but is not limited to, herbaceous material, agricultural residues, forestry residues, municipal solid wastes, waste paper and pulp and paper mill residues. The cellulose- or hemicellulose-containing material can be any type of biomass including, but not limited to, wood resources, municipal solid waste, wastepaper, crops and crop residues (see, for example, Wiselogel of al., 1995, in "Handbook on Bioethanol" (Charles E. Wyman, editor), pp. 105-1 18). In some embodiments the cellulose-containing material is in the form of lignocellulose, e.g., a plant cell wall material containing lignin, cellulose and hemicellulose in a mixed matrix.

In one embodiment, the cellulose- or hemicellulose-containing material is corn stover. In another embodiment, the cellulose-containing material is corn fiber, corn cobs, switch grass or rice straw. In another embodiment, the cellulose- or hemicellulose-containing material is paper and pulp processing waste. In another embodiment, the cellulose- or hemicellulose-containing material is woody or herbaceous plants. In another embodiment, the cellulose- or hemicellulose-containing material is bagasse.

Cellulose is a polymer of the simple sugar glucose covalently bonded by beta-1,4-linkages. Cellulose is a straight chain polymer: unlike starch, no coiling or branching occurs and the molecule adopts an extended and rather stiff rod-like conformation, aided by the equatorial conformation of the glucose residues. The multiple hydroxyl groups on the glucose from one chain form hydrogen bonds with oxygen molecules on the same or on a neighbour chain, holding the chains firmly together side-by-side and forming microfibrils with high tensile strength.

Compared to starch, cellulose is also much more crystalline. Whereas starch undergoes a crystalline to amorphous transition when heated beyond 60-70° C. in water (as in cooking), cellulose requires a temperature of 320° C. and pressure of 25 MPa to become amorphous in water.

Several different crystalline structures of cellulose are known, corresponding to the location of hydrogen bonds between and within strands. Natural cellulose is cellulose I, with structures Iα and Iβ. Cellulose produced by bacteria and algae is enriched in Iα while cellulose of higher plants consists mainly of Iβ. Cellulose in regenerated cellulose fibers is cellulose II. The conversion of cellulose I to cellulose II is not reversible, suggesting that cellulose I is metastable and cellulose II is stable. With various chemical treatments it is possible to produce the structures cellulose III and cellulose IV.

Hemicellulose is derived from several sugars in addition to glucose, especially xylose but also including mannose, galactose, rhamnose and arabinose. Hemicellulose consists of shorter chains than cellulose; around 200 sugar units. Furthermore, hemicellulose is branched, whereas cellulose is unbranched.

Chitin is defined herein as any polymer containing beta-(1-4) linked N-acetylglucosamine residues that are linked in a linear fashion. Crystalline chitin in the alpha form (where the chains run anti-parallel), beta form (where the chains run parallel) or gamma form (where there is a mixture of parallel and antiparallel chains), amorphous chitin, colloidal chitin, chitin forms in which part (e.g., up to 5, 10, 15 or 20%) of the N-acetylglucosamine sugars are deacetylated are all included within the definition of this term.

Other forms of chitin that are found in nature include copolymers with proteins and these copolymers, which include protein chitin matrices that are found in insect and crustacean shells and any other naturally occurring or synthetic copolymers comprising chitin molecules as defined herein.

The term "chitin" thus includes purified crystalline alpha, beta and gamma preparations, or chitin obtained or prepared from natural sources, or chitin that is present in natural sources. Examples of such natural sources include squid pen, shrimp shells, crab shells, insect cuticles and fungal cell walls. Examples of commercially available chitins are those available from sources such as France Chitin, Hov-Bio, Sigma, Sekagaku Corp, amongst others.

Starch or amylum is a carbohydrate consisting of a large number of glucose units joined by glycosidic bonds.

Lignin is a class of complex organic polymers. Lignin is one of the main classes of structural materials in the support tissues of vascular plants and some algae. Lignin is particularly important in the formation of cell walls, especially in wood and bark, because it of its rigidity. The exact composition of lignin varies from species to species. In plants, lignin fills the spaces in the cell wall between cellulose, hemicellulose, and pectin components, especially in xylem tracheids, vessel elements and sclereid cells. It is covalently linked to hemicellulose and crosslinks different plant polysaccharides, conferring mechanical strength to the cell wall and by extension to the plant as a whole.

The organic substrate may comprise or consist of a polysaccharide, a carbohydrate, a chitin, a protein, a lipid or a hydrocarbon having a straight or a branched chain $C_1$-$C_n$, where n is an integer, an aromatic hydrocarbon, an alkane, an alkene, a cycloalkane or an alkyne-based compound, such as methane, ethane, butane or propane.

In particular embodiments, the organic substrate comprises or consists of cellulose and/or hemicellulose and optionally lignin. The organic substrate may comprise or consist of chitin. The organic substrate may comprise or consist of a protein. The organic substrate may comprise or consist of a lipid. The organic substrate may comprise or consist of a combination of organic substrates. Accordingly, in some embodiments, the organic substrate comprises two or more organic substrates, where each of the organic substrates may comprise or consist of a polysaccharide, a carbohydrate, a chitin, a protein, or a lipid.

The organic substrate may comprise or consist of carboxymethyl cellulose, cellulose nanofibers, oxidised cellulose, oxidised cellulose nanofibers, (2,2,6,6-Tetramethylpiperidin-1-yl)oxyl-oxidised cellulose, (2,2,6,6-tetramethylpiperidin-1-yl)oxidanyl-oxidised cellulose, (TEMPO)-oxidised cellulose, (2,2,6,6-Tetramethylpiperidin-1-yl)oxyl-oxidised cellulose, (2,2,6,6-tetramethylpiperidin-1-yl)oxidanyl-oxidised cellulose or (TEMPO)-oxidised cellulose nanofibers.

Light Harvesting Molecule

It will be understood that the term 'light harvesting molecule' may also refer to a light harvesting complex comprising more than one light harvesting molecule throughout this disclosure. In some embodiments, the light harvesting molecule may be part of a complex.

The light harvesting molecule comprised within the present system is capable of absorbing energy from a photon and transmitting this energy to an electron within the light harvesting molecule, which then achieves a higher energy level. When the excited molecule has a neighbour molecule, the excitation energy may also be transferred to this neighbour molecule through electromagnetic interactions, charge transfer and quantum effects.

In some embodiments, the light harvesting molecule is derived from a photosynthetic organism such as a cyanobacterium, a plant such as a terrestrial plant, or algae such as red algae or green algae. The light harvesting molecule may be purified from said organisms, by methods known in the art. Light harvesting molecules are commercially available.

Chlorophylls a and b are abundant in green plants. The chlorophylls have a complex ring structure that is chemically related to the porphyrin-like groups found in hemoglobin and cytochromes. Carotenoids are linear molecules with multiple conjugated double bonds that absorb light in the 400 to 500 nm region, giving carotenoids their characteristic orange color. The majority of pigments absorb certain wavelengths of light and reflect non-absorbed wavelengths and function as parts of antenna complexes, collecting light and transferring the absorbed energy to the chlorophylls in the reaction center complex, where the chemical oxidation and reduction reactions leading to long-term energy storage take place.

In photosynthetic plants, antenna systems function to deliver energy efficiently to the reaction centers with which they are associated. The molecular structures of antenna pigments are quite diverse, although all of them are associated in some way with the photosynthetic membrane. The physical mechanism by which excitation energy is conveyed from the chlorophyll that absorbs the light to the reaction center is thought to be resonance transfer (Resonance Energy Transfer-RET). By this mechanism the excitation energy is transferred from one molecule to another by a non-radiative process. Light absorbed by carotenoids or chlorophyll b in the light harvest complex proteins is rapidly transferred to chlorophyll a and then to other antenna pigments that are intimately associated with the reaction center.

Light harvesting efficiency can be increased by combining light harvesting molecules which have optimal efficiencies at different parts of the light spectrum.

Chlorophyll a has two peaks of optimal efficiency, one in the blue part of the spectrum (around 430 nm) and one in the red part of the spectrum (680 nm), there are "associated pigments" which take advantage of nearly every part of the visible spectrum, and most of the energy absorbed is passed along a chain of receptors (losing bits along the way) until the energy is equivalent to that absorbed at 700 nm. Carotenoids are linear conformation molecules with multiple conjugated double bonds. Absorption bands in the 400 to 500 nm region give carotenoids their characteristic orange color. The majority of the pigments serve as an antenna complex, collecting light and transferring the energy to the reaction center complex, where the chemical oxidation and reduction reactions leading to long-term energy storage take place. Light absorbed by carotenoids or chlorophyll b in the light harvest complex proteins is rapidly transferred to chlorophyll a and then to other antenna pigments that are intimately associated with the reaction center.

Three forms of chlorophyll c are known: chlorophyll c1, c2 and c3. Chlorophyll c can be found in certain marine algae, including the photosynthetic Chromista (e.g. diatoms, brown algae) and dinoflagellates. Chlorophyll d is typically found in marine red algae and cyanobacteria. Chlorophyll d absorbs far-red light, at 710 nm wavelength. Chlorophyll f is found in stromatolites.

In some embodiments, the light harvesting molecule is derived from a compound capable of absorbing light such as lignin or a carotenoid. The lignin can be lignin naturally occurring in the plant cell wall or it can be an isolated or technical lignin, which is added to the system. The absorption spectra of lignin typically have peaks around 180-200 nm, 220-240 nm and 280-300 nm.

In some embodiments, the light harvesting molecule is a chlorophyll, a bacteriochlorophyll, a phycobilisome, a phycobilin, a chlorophyllide, a chlorophyllin, a thylakoid membrane, a chloroplast, a chlorosome, a rhodopsin, a carotenoid, an anthocyanin, a bilirubin, a luciferin, a xanthophyll, a flavonoid, a porphyrin, a polyene enolate, or variants or combinations thereof. In some embodiments, the light harvesting molecule is selected from chlorophyll a, chlorophyll b, chlorophyll c1, chlorophyll c2, chlorophyll c3, chlorophyll d and chlorophyll f. In some embodiments, the light harvesting molecule is a chlorophyllin. In some embodiments, the light harvesting molecule is a mixture of chlorophyllin and chlorophyllide. Such mixtures may comprise chlorophyllin and chlorophyllide in a ratio of 10:1 to 1:1, such as in a ratio of 9:1, such as in a ratio of 8:1, such as in a ratio of 7:1, such as in a ratio of 6:1, such as in a ratio of 5:1, such as in a ratio of 4:1, such as in a ratio of 3:1, such as in a ratio of 2:1.

The light harvesting molecule may comprise a metal such as ruthenium, zinc or magnesium. The light harvesting molecule may comprise a metal such as platinum, rhenium or iridium.

Accordingly, in some embodiments the light harvesting molecule is chlorophyll such as chlorophyll a, chlorophyll b, chlorophyll c1, chlorophyll c2, chlorophyll c3, chlorophyll d and chlorophyll f, which comprises magnesium.

In particular embodiments, the light harvesting molecule is not naturally occurring. Thus, in some embodiments, the light harvesting molecule is synthetic. A synthetic light harvesting molecule may have pi-orbitals that can be excited. A synthetic light harvesting molecule preferably has a photochemical activity. Methods to synthesise light harvesting molecules are known in the art. For example, such molecules can be made from boron dipyrromethene dyes and pyrene as reported by R Ziessel et al, 2013. Another example of a synthetic light harvesting complex comprises dendrimers dased on Transition-Metal Complexes as described by Balzani et al., 1998.

The light harvesting molecule is preferably capable of entering an excited state when absorbing a photon. In some embodiments, the excited state of the light harvesting molecule has a long lifetime. A long lifetime as understood herein is a lifetime of more than 1 ns, such as 5 ns, such as 10 ns, such as 25 ns, such as 50 ns, such as 75 ns, such as 100 ns or more.

In other embodiments, the light harvesting molecule has a lifetime of less than 1 ns, such as less than 900 ps, such as less than 800 ps, such as less than 700 ps, such as less than 600 ps, such as less than 500 ps, such as less than 400 ps, such as less than 300 ps, such as less than 200 ps, such as less than 100 ps, such as less than 75 ps, such as less than 50 ps, such as less than 25 ps, such as less than 10 ps.

It will be understood that systems comprising more than one kind of light harvesting molecule are also envisaged. This may be relevant if the system is to be used for chemically modifying an organic substrate in settings where the nature of the light source is varying, so that if the light's wavelength becomes suboptimal for one kind of light harvesting molecule, another light harvesting molecule being capable of entering an excited state at the new wavelength may take over.

Catalyst

The present system comprises at least one catalyst. The catalyst can be organic or inorganic.

The at least one catalyst may be at least two catalysts, such as at least three catalysts, such as at least four catalysts, such as at least five catalysts, such as at least ten catalysts or more.

In some embodiments, the at least one catalyst is an inorganic coordination compound comprising metal ions, preferably copper, iron or zinc ions. Inorganic coordination compounds are inorganic compounds comprising metal ions bound to a ligand such as an atom, an ion, or a molecule that can donate electrons to the metal. The inorganic coordination compound can be neutral or charged. The at least one catalyst may be at least two inorganic coordination compounds, such as at least three inorganic coordination compounds, such as at least four inorganic coordination compounds, such as at least five inorganic coordination compounds, such as at least ten inorganic coordination compounds or more.

In other embodiments, the at least one catalyst is organic. In particular embodiments, the organic catalyst is an enzyme. Preferably, the enzyme is a metalloprotease such as an oxidase comprising a metal ion cofactor, such as a copper ion, an iron ion or a zinc ion.

The at least one catalyst may be at least two enzymes, such as at least three enzymes, such as at least four enzymes, such as at least five enzymes, such as at least ten enzymes or more.

The at least one enzyme comprised in the present system can be a monooxygenase such as a lytic polysaccharide monooxygenase (LPMO), a methane monooxygenase (MMO) or a particulate methane monooxygenase (PMO).

Oxidative processes are essential for the degradation of plant biomass. A class of powerful and widely distributed oxidative enzymes, the lytic polysaccharide monooxygenases (LPMOs), oxidise the most recalcitrant polysaccharides and require extracellular electron donors. LPMOs catalyse oxidative cleavage of the glycosidic chain on the crystalline surface of cellulose or chitin to create and thereby are believed to create an entry point for hydrolytic cellulases or chitinases. When LPMOs are combined with hydrolases there is a strong synergistic effect on biomass degradation. LPMOs are found in fungi, bacteria and viruses, spanning a number of terrestrial and aquatic ecosystems and are classified in the carbohydrate active enzyme database as auxiliary activity (AA) enzymes class 9, 10, 11 and 13. The enzymes play an essential role, yet not well-understood, in the turnover of organic matter. Some organisms have multiple genes for LPMO enzymes, and especially in plant cell wall-degrading fungi, the AA9 family is highly present with some species containing >30 AA9-encoding genes5

The AA9 (formerly GH61) proteins are copper-dependent lytic polysaccharide monooxygenases (LPMOs), which catalyse cleavage of cellulose chains with oxidation of various carbons (C-1, C-4 and C-6).

The AA10 (formerly CBM33) proteins are copper-dependent lytic polysaccharide monooxygenases (LPMOs). Some AA10 proteins have been shown to act on chitin, others on cellulose.

The AA11 proteins are copper-dependent lytic polysaccharide monooxygenases (LPMOs). Cleavage of chitin chains with oxidation of C-1 has been demonstrated for a AA11 LPMO from *Aspergillus oryzae* (Hemsworth et al., 2014).

AA13 proteins are copper-dependent lytic polysaccharide monooxygenases (LPMOs); cleavage of starch with oxidation of C-1 at the site of cleavage has been demonstrated for the LPMO encoded by gene NCU08746 from *Neurospora crassa*.

Accordingly, the present system may in some embodiments comprise at least one LPMO belonging to the AA9 family. In some embodiments, the system comprises at least one LPMO belonging to the AA9 family, such as at least two LPMOs belonging to the AA9 family, such as at least three LPMOs belonging to the AA9 family, such as at least four LPMOs belonging to the AA9 family, such as at least five LPMOs belonging to the AA9 family, such as at least ten LPMOs belonging to the AA9 family or more.

In other embodiments, the system may comprise at least one LPMO belonging to the AA10 family. In some embodiments, the system comprises at least one LPMO belonging to the AA10 family, such as at least two LPMOs belonging to the AA10 family, such as at least three LPMOs belonging to the AA10 family, such as at least four LPMOs belonging to the AA10 family, such as at least five LPMOs belonging to the AA10 family, such as at least ten LPMOs belonging to the AA10 family or more.

In yet other embodiments, the system may comprise at least one LPMO belonging to the AA11 family. In some embodiments, the system comprises at least one LPMO belonging to the AA11 family, such as at least two LPMOs belonging to the AA11 family, such as at least three LPMOs belonging to the AA11 family, such as at least four LPMOs belonging to the AA11 family, such as at least five LPMOs belonging to the AA11 family, such as at least ten LPMOs belonging to the AA11 family or more.

In other embodiments, the system may comprise at least one LPMO belonging to the AA13 family. In some embodiments, the system comprises at least one LPMO belonging to the AA13 family, such as at least two LPMOs belonging to the AA13 family, such as at least three LPMOs belonging to the AA13 family, such as at least four LPMOs belonging to the AA13 family, such as at least five LPMOs belonging to the AA13 family, such as at least ten LPMOs belonging to the AA13 family or more.

Also disclosed herein are systems comprising combinations of LPMOs belonging to different families. Such combinations may be useful for chemically modifying mixtures of substrates, where the different substrates may be chemically modified with different efficiencies depending on the nature of the LPMO. Accordingly, in some embodiments, the system comprises at least one LPMO belonging to the AA9 family and at least one LPMO belonging to the AA10 family, such as one LPMO belonging to the AA9 family and one LPMO belonging to the AA10 family. In other embodiments, the system comprises at least one LPMO belonging to the AA9 family and at least one LPMO belonging to the AA11 family, such as one LPMO belonging to the AA9 family and one LPMO belonging to the AA11 family. In other embodiments, the system comprises at least one LPMO belonging to the AA9 family and at least one LPMO belonging to the AA13 family, such as one as one LPMO belonging to the AA9 family and one LPMO belonging to the AA13 family. In other embodiments, the system comprises at least one LPMO belonging to the AA10 family and at least one LPMO belonging to the AA11 family, such as one LPMO belonging to the AA10 family and one LPMO belonging to the AA11 family. In other embodiments, the system comprises at least one LPMO belonging to the AA10 family and at least one LPMO belonging to the AA13 family, such as one LPMO belonging to the AA10 family and one LPMO belonging to the AA13 family. In other embodiments, the system comprises at least one LPMO belonging to the AA9 family, at least one LPMO belonging to the AA10 family and at least one LPMO belonging to the AA11 family. In other embodiments, the system comprises at least one LPMO belonging to the AA9 family, at least one LPMO belonging to the AA10 family and at least one LPMO belonging to the AA13 family. In other embodiments, the system comprises at least one LPMO belonging to the AA9 family, at least one LPMO belonging to the AA11 family and at least one LPMO belonging to the AA13 family. In other embodiments, the system comprises at least one LPMO belonging to the AA10 family, at least one LPMO belonging to the AA11 family and at least one LPMO belonging to the AA13 family. In other embodiments, the system comprises at least one LPMO belonging to the AA9 family, at least one LPMO belonging to the AA10 family, at least one LPMO belonging to the AA11 family and at least one LPMO belonging to the AA13 family.

Examples of suitable LPMOs comprise, but are not limited to: AA10 from *Thermobifida fusca* (TfLPMOa), AA9 from *Thielavia terrestris*, AA9 from *Thermoascus aurantiacus* or AA9 from *Thielavia terrestris*.

Without wishing to be bound by theory, contacting the at least one catalyst with a light-harvesting molecule as described herein appears to widen the substrate specificity of the LPMOs. It is thus possible to use cellulose-specific AA9 LPMOs to oxidise e.g. xyloglucan. Thus in some embodiments, the system for chemical modification of an organic substrate comprises a catalyst such as an LPMO, wherein the said LPMO is not necessarily highly specific for said organic substrate. In other embodiments, the LPMO is highly specific for said organic substrate. Likewise, in some embodiments, the catalyst is an MMO or a pMMO which is not necessarily highly specific for the organic substrate to be chemically modified by the system.

Reductant

The systems disclosed herein also comprise a reductant and/or an electrochemical electrode. The term 'reductant' will herein be used interchangeably with the term 'reducing agent'.

A reductant is an element or compound in a redox (reduction-oxidation) reaction that reduces another species and in so doing becomes oxidisoxidised and is therefore the electron donor in the redox reaction. Preferably the reducing agent is non-enzymatic. In embodiments where the at least one catalyst is an enzyme, the reducing agent may function as an electron donor in the enzymatic process. Without wishing to be bound by theory, the reductant may act as an electron donor to the light harvesting molecule, which in turn is an electron donor to the catalyst. The reductant may thus stabilise the light harvesting molecule, thereby preventing photobleaching.

In some embodiments, the reductant is a soluble reductant, such as, but not limited to, ascorbic acid, a lignan, a hydroquinone, 2-(20-hydroxyphenyl)benzothiazole, 3-hydroxyanthranilic acid or a technical lignin such as lignosulfonate, or at least one fraction thereof, a ferulic acid, a gallic acid, a caffeic acid, 3-hydroxyanthranilic acid, a technical lignin such as lignosulfonate, or at least one fraction thereof, or an insoluble reductant, such as native lignin, kraft lignin, organosolv lignin, or at least one fraction thereof, or a lignan, or at least one fraction thereof. In some embodiments, the redox potential of the reductant is lower than the redox potential of ascorbic acid. In other embodiments, the redox potential of the reductant is higher than the redox potential of lignin. Preferably, the reductant has a redox potential which is higher than the redox potential of lignin but lower than the redox potential of ascorbic acid.

In other embodiments, the reductant is an insoluble reductant, such as native lignin, kraft lignin, organosolv lignin, or at least one fraction thereof. Because of its electronic structure, lignin may function both as a light-harvesting molecule and as a reductant, as shown in e.g. example 3. Thus in some embodiments, the system comprises a light harvesting molecule, at least one catalyst and a reductant, where lignin is the light harvesting molecule and the reductant. Accordingly, in some embodiments, the system comprises lignin and at least one catalyst.

In some embodiments, the present systems comprise an electrochemical electrode instead of or in addition to a reductant.

The present systems may comprise a combination of reductants, such as a combination of two reductants or more. The system may also comprise a combination of soluble and insoluble reductants.

Accordingly, the system may comprise a combination of ascorbic acid and lignan. The system may comprise a combination of ascorbic acid and a hydroquinone. The system may comprise a combination of ascorbic acid and 2-(20-hydroxyphenyl)benzothiazole. The system may comprise a combination of ascorbic acid and 3-hydroxyanthranilic acid. The system may comprise a combination of ascorbic acid and a technical lignin or a fraction thereof. The system may comprise a combination of ferulic acid and lignan. The system may comprise a combination of ferulic acid and a hydroquinone. The system may comprise a combination of ferulic acid and 2-(20-hydroxyphenyl) benzothiazole. The system may comprise a combination of ferulic acid and 3-hydroxyanthranilic acid. The system may comprise a combination of ferulic acid and a technical lignin or a fraction thereof. The system may comprise a combination of gallic acid and lignan. The system may comprise a combination of gallic acid and a hydroquinone. The system may comprise a combination of gallic acid and 2-(20-hydroxyphenyl)benzothiazole. The system may comprise a combination of gallic acid and 3-hydroxyanthranilic acid. The system may comprise a combination of gallic acid and a technical lignin or a fraction thereof. The system may comprise a combination of caffeic acid and lignan. The system may comprise a combination of caffeic acid and a hydroquinone. The system may comprise a combination of caffeic acid and 2-(20-hydroxyphenyl)benzothiazole. The system may comprise a combination of caffeic acid and 3-hydroxyanthranilic acid. The system may comprise a combination of caffeic acid and a technical lignin or a fraction thereof. The system may comprise a combination of native lignin and a hydroquinone. The system may comprise a combination of native lignin and 2-(20-hydroxyphenyl)benzothiazole. The system may comprise a combination of native lignin and 3-hydroxyanthranilic acid.

Light Source

The present systems are light-driven, i.e. they can chemically modify an organic substrate using essentially only light as an external energy source. Thus the systems of the present disclosure can be activated or deactivated by adding or removing a light source, respectively.

In some embodiments, the system disclosed herein further comprises a light source. The light source may be natural or artificial. For example, the natural light source may be sunlight. In some embodiments, the system comprises both a natural and an artificial light source.

The light source preferably has a wavelength between 180 and 850 nm, such as between 350 and 850, such as between 400 and 700 nm. In some embodiments, the light source is a photosynthetically active radiation having a wavelength between 350 and 850 nm, such as between 400 and 700 nm. In some embodiments, the light source has a wavelength between 180 and 200 nm. In some embodiments, the light source has a wavelength between 220 and 240 nm. In some embodiments, the light source has a wavelength between 280 and 300 nm.

In particular embodiments, the light source is a combination of light sources of different wavelength, which are capable to excite a combination of light harvesting molecules, where the light harvesting molecules may enter an excited state at different wavelengths. In some embodiments, the light harvesting molecule is chlorophyll, such as chlorophyll a, chlorophyll b, chlorophyll c1, chlorophyll c2, chlorophyll c3, chlorophyll or chlorophyll f, and the light source is not a green light source. In some embodiments, the light harvesting molecule is chlorophyll and the light source is a source of white light, blue light or red light. In one embodiment, the light harvesting molecule is chlorophyll and the light source is a photosynthetically active radiation having a wavelength between 400 and 700 nm. In some embodiments, the light harvesting molecule is derived from an alga, and the light source has a wavelength between 350 and 850 nm. In some embodiments, the light harvesting molecule is lignin and the light source has a wavelength between 180 and 850 nm, such as between 180 and 300 nm, such as between 180 and 200 nm, between 220 and 240 nm or between 280 and 300 nm. In some embodiments, the light harvesting molecule is a chlorophyllide and/or chlorophyllin and the light source is a photosynthetically active radiation having a wavelength between 400 and 700 nm.

The system may also comprise means for activating or deactivating the light source. In the case of artificial light sources, such means may be a switch capable of interrupting the light source. It may also be a shield, which can be placed between the system and the light source, so that essentially no light reaches the system.

The nature of the reductant used in the system may influence the choice of light source. Some reductants may require a light source comprising UV light. In some embodiments, the reductant is lignin and the light source comprises UV radiations. In other embodiments, the reductant is ascorbic acid and light source comprises UV radiations.

In some embodiments, the light source is intermittent. The light source may be switched on and off at regular periods of time, so that it is turned on during a first interval and turned off during a second interval. The first and second intervals may be of equal length or they may be of different length. The switching on and off of the light source may be adapted as desired if controlling the delivery of electrons or performing reactions in a sequential manner is desirable.

Organic Solvents, Eutectic Solvents and Ionic Liquids

The present systems may further comprise additional compounds.

For example, the system disclosed herein may further comprise a solvent.

In some embodiments, the solvent is an organic solvent. Organic solvents are well known in the art and comprise ethanol, dioxane, pyridine or hexane. In some embodiments, the solvent is ethanol. In some embodiments, the solvent is dioxane. In some embodiments, the solvent is pyridine. In some embodiments, the solvent is hexane. The solvent may be a mixture of solvents.

In some embodiments, the solvent is a eutectic solvent. Deep eutectic solvents are mixtures of salts such as, but not limited to, choline chloride and uncharged hydrogen bond donors. The hydrogen bond donor may be as urea, oxalic acid, or glycerol. Thus in some embodiments, the eutectic solvent is a mixture of choline chloride and urea. In other embodiments, the eutectic solvent is a mixture of choline chloride and oxalic acid. In other embodiments, the eutectic solvent is a mixture of choline chloride and glycerol. In a particular embodiment, the eutectic solvent is a mixture of choline chloride and urea in a 1:2 molar ratio.

The present systems may comprise an ionic liquid. Examples of suitable ionic liquids include, but are not limited to, imidazolium-based ionic liquids such as 1-ethyl-3-methylimidazolium acetate or 1-allyl-3-methylimidazolium iodide; tertiary amine-based ionic liquids such as 4-((diethylamino)methyl)-2-methoxyphenol or N-ethyl-N-(4-methoxybenzyl)ethanamine.

The system may be an aqueous or a non-aqueous system.

Accordingly, also disclosed herein is a non-aqueous system comprising a light harvesting molecule, at least one catalyst and a reductant and/or an electrochemical electrode as described above, said system further comprising a eutectic solvent. Also disclosed is a non-aqueous system comprising a light harvesting molecule, at least one catalyst and a reductant and/or an electrochemical electrode as described above, said system further comprising an ionic liquid. Also disclosed is a non-aqueous system comprising a light harvesting molecule, at least one catalyst and a reductant and/or an electrochemical electrode as described above, said system further comprising a eutectic solvent and an ionic liquid.

The present disclosure also relates to an aqueous system comprising a light harvesting molecule, at least one catalyst and a reductant and/or an electrochemical electrode as described above, said system further comprising a eutectic solvent. Also disclosed is an aqueous system comprising a light harvesting molecule, at least one catalyst and a reductant and/or an electrochemical electrode as described above, said system further comprising an ionic liquid. Also disclosed is an aqueous system comprising a light harvesting molecule, at least one catalyst and a reductant and/or an electrochemical electrode as described above, said system further comprising a eutectic solvent and an ionic liquid.

Additional Catalyst

The present systems may further comprise at least one additional catalyst, which may be useful to further increase the yield of the chemical modification which the system is capable of carrying out. The additional catalyst may be a hydrolase, a lipase, a protease or a transferase or a combination thereof. The at least one additional catalyst may be a homogenous catalyst or a heterogeneous catalyst. Accordingly, in some embodiments, the at least one additional catalyst is a hydrolase, a lipase, a protease, a transferase, a cellulase or a combination thereof in a liquid phase, and at least some of the other reactants are in a solid phase. In other embodiments, the at least one additional catalyst is a hydrolase, a lipase, a protease, a transferase, a cellulase or a combination thereof in a solid phase, and at least some of the other reactants are in a liquid phase. The term 'other reactants' shall be construed as referring to any component in the system which is not the at least one additional catalyst, for example the light harvesting molecule, the at least one catalyst, the reductant, but also any of the optional components of the system, such as the organic substrate to be chemically modified, the products and intermediates resulting from the chemical modification of the substrate.

In some embodiments, the at least one additional catalyst is at least two additional catalysts, such as at least three additional catalysts, such as at least four additional catalysts, such as at least five additional catalysts or more. In embodiments where two or more additional catalysts are present, some or all of the two or more additional catalysts may be homogenous catalysts, or some or all of the two or more additional catalysts may be heterogeneous catalysts.

In some embodiments, the at least one additional catalyst is a cellulase. Cellulases are enzymes produced chiefly by fungi, bacteria, and protozoans, which are able to catalyze cellulolysis, i.e. the decomposition of cellulose and of some related polysaccharides. The term herein also refers to any naturally occurring mixture or complex of various such enzymes, that may act serially or synergistically to decompose cellulosic material. Cellulases are capable of hydrolysing the 1,4-beta-D-glycosidic linkages in cellulose, but also in hemicellulose, lichenin and cereal beta-D-glucans. The cellulase that may be used as additional catalyst in the present systems may be an endocellulase (EC 3.2.1.4), an exocellulase (EC 3.2.1.91), a beta-glucosidase (EC 3.2.1.21), an oxidative cellulase or a cellulose phosphorylase, or a combination (or "cocktail") thereof. In some embodiments, the cellulase is an exocellulase. Exocellulases are further classified into type I, which work processively from the reducing end of the cellulose chain, and type II, which work processively from the non-reducing end. In one embodiment, the cellulase is a type II exocellulase. In another embodiment, the cellulase is a type I exocellulase. In yet another embodiment, the at least one additional catalyst is two additional catalysts, wherein the first additional catalyst is a type I exocellulase and the second additional catalyst is a type II exocellulase. In one embodiment, the additional catalyst is Celluclast®. The system may comprise a type I exocellulase and/or a type II exocellulase, and additionally also a beta-glucosidase.

Combinations and Other Characteristics of the System

The skilled person will understand that the present systems can be adapted as needed. For example, if chemical modification of a combination of organic substrates is desirable, the present system may be adapted to comprise a combination of several elements, such as more than one light harvesting molecule, catalyst and/or reductant and/or additional catalysts, in order to maximise the efficiency of the system.

In some embodiments, it may be convenient to immobilise at least one component of the system. Accordingly, at least one of the light harvesting molecule, the catalyst, the reducing agent and the at least one additional catalyst of the present system may be immobilised. Immobilisation methods are known in the art.

The present systems may also comprise oxygen and/or hydrogen peroxide. In some embodiments, oxygen and/or hydrogen peroxide is continuously added to the system. In specific embodiments, the chemical modification is not limited by the amount of oxygen.

The present system is preferably stable. In some embodiments, the system is stable for at least 5 minutes, such as at least 10 minutes, such as at least 20 minutes, such as at least 30 minutes, such as at least 1 hour, such as at least 2 hours, such as at least 5 hours, such as at least 10 hours, such as at least 16 hours, such as at least 24 hours.

The present systems may function at ambient conditions. Accordingly, in some embodiments, the temperature of the system is between 0 and 99° C. In some embodiments, the temperature of the system is between 10 and 70° C. In some embodiments, the temperature of the system is the ambient temperature. The present systems may be stable in the absence of cooling or heating systems aimed at controlling the temperature and maintaining it stable. Accordingly, the systems disclosed herein may function stably with varying or unstable temperatures.

As the skilled person is aware, some light-harvesting molecules as disclosed herein have high thermal stability. Likewise, some catalysts, in particular some emzymes, are stable at temperatures up to 100° C. or more. Chlorophyll, for example, can be boiled without losing stability. Accordingly, in some embodiments, the temperature of the present systems may be higher than 99° C., such as higher than 100° C., such as 101° C. or more, such as 102° C. or more, such as 103° C. or more, such as 104° C. or more, such as 105° C., or more; preferably, the temperature of the system is such that the light-harvesting molecule and/or the catalyst retain their stability. In preferred embodiments, the temperature of the system is such that the system is thermally stable.

Preferably, the pH of the system is between 3 and 10, such as between 4 and 8, such as between 5 and 8, such as between 6 and 8. In some embodiments, the light harvesting molecule is a chlorophyll and the pH is 6 or more, such as 6.5 or more, such as 7.0 or more, such as 7.5 or more, such as 8.0 or more. In other embodiments, the light harvesting molecule is lignin and the pH is 3 or more, such as 3.5 or more, such as 4.0 or more, such as 4.5 or more, such as 5.0 or more, such as 6.0 or more, such as 6.5 or more, such as 7.0 or more, such as 7.5 or more, such as 8.0 or more. In other embodiments, the light harvesting molecule is a chlorophyllide and/or chlorophyllin and the pH is 3 or more, such as 3.5 or more, such as 4.0 or more, such as 4.5 or more, such as 5.0 or more, such as 6.0 or more, such as 6.5 or more, such as 7.0 or more, such as 7.5 or more, such as 8.0 or more. As will be recognised by the skilled person, preferably the pH is such that it is optimal for the catalyst to carry out the chemical modification. Thus in some embodiments, the pH of the system is within the optimal pH range for the particular catalyst comprised in the system. For example, if the system comprises TfLPMOa from *Thermobifida fusca*, the pH of the system is preferably between 7 and 8, such as about 7 or such as about 8. If the catalyst is TtGH61R from *Thielavia terrestris*, the pH of the system is about 6.3.

The present systems may have a pressure which is equal to atmospheric pressure. In some embodiments, the pressure of the system is above atmospheric pressure. In other embodiments, the pressure of the system is below atmospheric pressure. Accordingly, the pressure of the system may be equal to 101325 Pa. The pressure of the system may be greater than 101325 Pa. The pressure of the system may be less than 101325 Pa. Systems where the pressure is greater than atmospheric pressure may be advantageous when the organic substrate is or comprises a gas such as methane, ethane, butane or propane, in that it may help increase solubility of the substrate.

In one particular embodiment, the organic substrate comprises or consists of cellulose, the reductant is ascorbic acid, the catalyst is an LPMO such as an AA10 LPMO such as TfLPMOa from *Thermobifida fusca*, TtGH61R from *Thielavia terrestris*, or TaGH61A from *Thermoascus aurantiacus*, the light harvesting molecule is chlorophyllide a, chlorophyllin and/or a mixture thereof.

In another particular embodiment, the organic substrate comprises or consists of cellulose, the reductant is ascorbic acid, the catalyst is an LPMO such as an AA10 LPMO such as TfLPMOa from *Thermobifida fusca*, TtGH61R from *Thielavia terrestris*, or TaGH61A from *Thermoascus aurantiacus*, the light harvesting molecule is a thylakoid membrane such as a thylakoid membrane from a cyanobacterium such as *Synechococcus* sp. PCC 7002.

In yet another particular embodiment, the organic substrate comprises cellulose, the reductant is lignin such as organosolv lignin, the catalyst is an LPMO such as an AA10 LPMO such as TfLPMOa from *Thermobifida fusca*, TtGH61R from *Thielavia terrestris*, or TaGH61A from *Thermoascus aurantiacus*, the light harvesting molecule is a thylakoid membrane such as a thylakoid membrane from a cyanobacterium such as *Synechococcus* sp. PCC 7002.

Methods for Chemical Modification of a Substrate

The systems described herein are well suited for chemically modifying an organic substrate. Accordingly, herein is provided a method for chemical modification of an organic substrate, said method comprising the steps of:
  i. providing an organic substrate;
  ii. contacting said organic substrate with a system comprising a light harvesting molecule, at least one catalyst and a reductant and/or an electrochemical electrode; and
  iii. exposing said organic substrate contacted with said system to a light source,
whereby the organic substrate is chemically modified.

In some embodiments, the chemical modification is an oxidation.

The organic substrate, light harvesting molecule, at least one catalyst, light source and chemical modification may be as described herein elsewhere.

The method may comprise one or more pre-treatment step, where the organic substrate may be concentrated, precipitated and/or washed.

The method may further comprise the step of providing the system with oxygen and/or hydrogen peroxide.

The method may further comprise a step of recovery of the resulting product. Such methods are known in the art and their choice may depend on the nature of the resulting product.

The method may further comprise additional steps for further modification of the resulting product. For example, if the substrate comprises cellulose which is oxidised in the present methods, it may be desirable to ferment the resulting monomers and oligomers to obtain biofuel or biomass. Methods of fermenting monosaccharides and oligosaccharides are known in the art.

The present methods may be adapted as needed. For example, a solution of phosphoric acid swollen cellulose in an appropriate buffer, such as a citrate-phosphate buffer, may be contacted with a liquid solution comprising a light harvesting molecule, such as a chlorophyllide a or thylakoid membranes, a reductant such as ascorbate and LPMO such as TfLPMO. The volume may be adjusted as needed with water. The mixture can then be exposed to sunlight and incubated with or without shaking, with optional heating or cooling. As can be seen in the examples, the efficiency of the system is not restricted to specific kinds of light harvesting molecules or reductants. Example 1 shows oxidation of a phosphoric acid swollen cellulose solution into monomers and oligomers using chlorophyll a as light harvesting molecule and ascorbic acid as reductant. Example 2 shows that chlorophyll a can be replaced by thylakoid membranes. Example 3 shows that lignin can be used as a reductant instead of ascorbic acid, and that lignin can function both as light harvesting molecule and as reductant in the same system.

The present methods may result in rapid modification of the organic substrate. In some embodiments, step iii) is performed for a duration of at least 1 minute, such as at least 2 minutes, such as at least 3 minutes, such as at least 4 minutes, such as at least 5 minutes, such as at least 10 minutes, such as at least 20 minutes, such as at least 30 minutes, such as at least 40 minutes, such as at least 50 minutes, such as at least 1 hour, such as at least 2 hours, such as at least 3 hours, such as at least 4 hours, such as at least 5 hours, such as at least 12 hours, such as at least 16 hours, such as at least 20 hours, such as at least 24 hours.

The present methods may result in partial or total modification of the organic substrate. The duration of step iii) may be adjusted depending on how much of the organic substrate it is desirable to modify. In some embodiments, at least 10% of the organic substrate is chemically modified, such as at least 20%, such as at least 30%, such as at least 40%, such as at least 50%, such as at least 60%, such as at least 70%, such as at least 80%, such as at least 90%, such as at least 95%, such as at least 99%, such as 100%.

Without being bound by theory, it appears that the efficiency of the present systems is enhanced by the presence of a light harvesting molecule, as shown in FIG. 7 which illustrates a possible model for how the present system works. Thus in some embodiments, the chemical modification of the organic substrate has a rate at least 5 times faster than the rate of a similar method performed in the absence of a light harvesting molecule, such as at least 10 times faster, such as at least 20 times faster, such as at least 30 times faster, such as at least 40 times faster, such as at least 50 times faster, such as at least 60 times faster, such as at least 70 times faster, such as at least 80 times faster, such as at least 90 times faster, such as at least 100 times faster. Some embodiments of the present disclosure may function in the absence of light. However, the efficiency of the chemical modification by the present systems is enhanced many-fold by the presence of light.

The present methods may be performed with systems having characteristics such as pH and pressure described herein above. The methods may be performed at a pressure which is equal to atmospheric pressure. In some embodiments, the pressure is above atmospheric pressure. In other embodiments, the pressure is below atmospheric pressure. Accordingly, the pressure may be equal to 101325 Pa. The pressure may be greater than 101325 Pa. The pressure may be less than 101325 Pa. It may be advantageous to carry out the present methods at a pressure which is greater than atmospheric pressure when the organic substrate is or comprises a gas such as methane, ethane, butane or propane, in that it may help increase solubility of the substrate.

In some embodiments, the substrate is an alkane, such as methane, ethane, butane or propane, the chemical modification is an oxidation, and one of the resulting products is an alcohol, such as methanol, ethanol, butanol or propanol. In a specific embodiment, the method is used to convert methane to methanol. The methane may be biogas-plant sourced methane. In another embodiment, the method is used to convert ethane to ethanol. In yet another embodiment, the method is used to convert butane to butanol. In yet another embodiment, the method is used to convert propane to propanol.

Accordingly, in one embodiment, the organic substrate comprises or consists of cellulose, the reductant is ascorbic acid, the catalyst is an LPMO such as an AA10 LPMO such as TfLPMOa from *Thermobifida fusca*, the light harvesting molecule is chlorophyllide a, the pH of the system is 7 and step iii) is performed for 3 hours at 50° C. and the light source is sun light.

In another embodiment, the organic substrate comprises or consists of cellulose, the reductant is ascorbic acid, the catalyst is an LPMO such as an AA10 LPMO such as TtGH61R from *Thielavia terrestris*, the light harvesting molecule is chlorophyllide a and/or chlorophyllin, the pH of the system is 6.3 and step iii) is performed for 3 hours at 50° C. and the light source is sun light.

In another embodiment, the organic substrate comprises or consists of cellulose, the reductant is ascorbic acid, the catalyst is an LPMO such as an AA10 LPMO such as TfLPMOa from *Thermobifida fusca*, the light harvesting molecule is a thylakoid membrane such as a thylakoid membrane from a cyanobacterium such as *Synechococcus* sp. PCC7002, the pH of the system is 7 and step iii) is performed for 3 hours at 50° C. and the light source is sun light.

In another embodiment, the organic substrate comprises or consists of cellulose, the reductant is ascorbic acid, the catalyst is an LPMO such as an AA10 LPMO such as TtGH61R from *Thielavia terrestris*, the light harvesting molecule is thylakoid membrane such as a thylakoid membrane from a cyanobacterium such as *Synechococcus* sp. PCC7002, the pH of the system is 6.3 and step iii) is performed for 3 hours at 50° C. and the light source is sun light.

In another embodiment, the organic substrate comprises or consists of cellulose, the reductant is lignin such as organosolv lignin, the catalyst is an LPMO such as an AA10 LPMO such as TfLPMOa from *Thermobifida fusca*, the light harvesting molecule is a thylakoid membrane such as a thylakoid membrane from a cyanobacterium such as *Synechococcus* sp. PCC7002, the pH of the system is 7 and step iii) is performed for 3 hours at 50° C. and the light source is sun light.

In another embodiment, the organic substrate comprises or consists of cellulose, the reductant is lignin such as organosolv lignin, the catalyst is an LPMO such as AA10 LPMO such as TtGH61R from *Thielavia terrestris*, the light harvesting molecule is a thylakoid membrane such as a thylakoid membrane from a cyanobacterium such as *Synechococcus* sp. PCC7002, the pH of the system is 6.3 and step iii) is performed for 3 hours at 50° C. and the light source is sun light.

The methods disclosed herein may, as mentioned above, comprise a further step of recovering the chemically modified substrate, i.e. the product of the reaction. The methods may also comprise a further step of processing the recovered product to another product. For example, methanol produced via chemical modification of methane via the present methods may be recovered by methods known to the skilled person. Once recovered, the methanol may be further processed into a fuel or a chemical.

Method for Manufacturing a System for Chemical Modification of an Organic Substrate The present disclosure also relates to a method for manufacturing a light-driven system for chemical modification of an organic substrate as described herein, and comprising a light harvesting molecule, at least one catalyst and a reductant and/or an electrochemical electrode, said method comprising the steps of providing a light harvesting molecule, at least one organic catalyst and a reductant and/or an electrochemical electrode.

The light harvesting molecule, the at least one organic catalyst and the reductant and/or electrochemical electrode may be as described herein elsewhere.

The method may further comprise the step of providing an organic substrate. One or more additional catalysts may also be provided, as described herein above. The method may also comprise the step of providing a light source.

EXAMPLES

Example 1. Chlorophyllin as Electron Donor and Ascorbic Acid as Reductant

In this experiment ascorbic acid was used as reductant and chlorophyllin as electron donor to the LPMO enzymes. The chlorophyllin was obtained from Chr. Hansen A/S, Denmark product C-100.000-WS-P in the form of a powder. Prior to use a 12% w/v solution in milliQ water was prepared. 100 µL of PASO (phosphoric acid swollen cellulose, solution 1.5% w/v) was used as substrate, 95 µL of citrate-phosphate buffer pH 8 at 100 mM of strength was added. Then 2 µL of ascorbate (100 mM solution), 0.5 µL of chlorophyllin, and 30 µg of TfLPMOa (*Thermobifida fusca* AA10, LPMO from Nzytech Ltda, Portugal) in 1 µL were added. Water was used to reach the final total volume of 200 µL. The incubation was run for 3 hours at 50° C., 1000 rpm shacking in an Eppendorf thermomixer, and light exposure by sun light. The light exposure was done by removing the lid of the thermomixer and placing it in direct sunlight (scattered clouds, mid-June, latitude 55.67 degrees north). Other LPMO enzymes were tested under identical conditions but at lower enzyme dosage (10 µg) and adjusted for pH: TtGH61E, and TaGH61A (from Novozymes A/S, Denmark) were tested at 6.3 of pH in 100 mM citrate-phosphate buffer.

The control experiments included chlorophyllin+LPMO and ascorbic acid+LPMO.

Results

Figure 1:
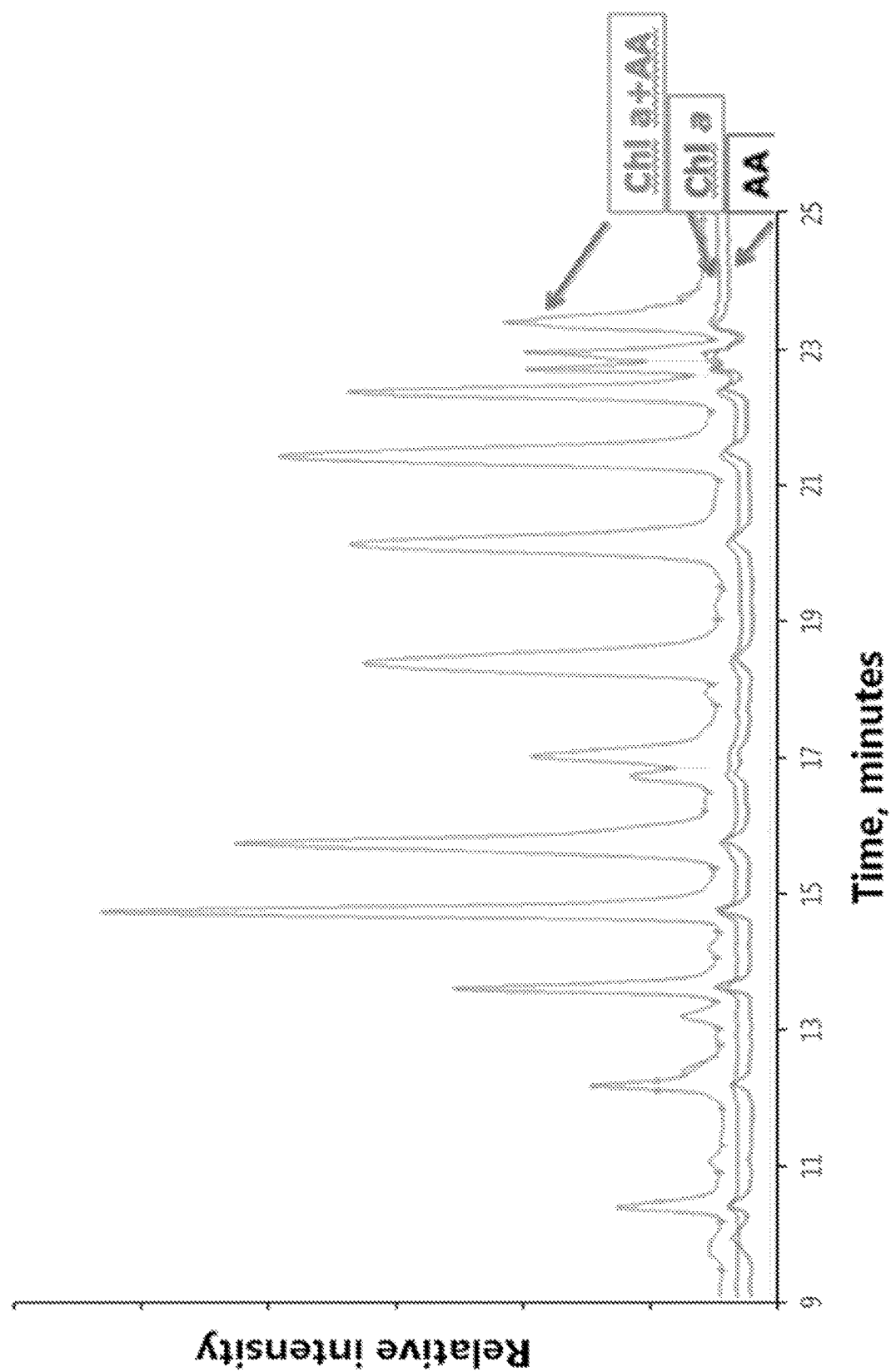
FIG. 1: HPAEC Chromatogram of LPMO treated PASC using different electron donors. All experiments were performed with 3 hours irradiation in sunlight. Chl+AA: Chlorophyllin+ascorbic acid+LPMO. Chl: Chlorophyllin+LPMO. AA: Ascorbic acid+LPMO.

The results are shown in FIG. 1. On the left side of the chromatogram are the reduced oligomers DP1 to DP6 and on the right side are the corresponding oxidisoxidised oligomers DP1 to DP6. There is a very clear effect of combining chlorophyllin and ascorbic acid as approximately a 50 times higher level of oligomers is observed compared to the ascorbic acid control. The level of oxidation with ascorbic acid is equal to what has been reported in previous work (Cannella et al., 2012).

The effect of light exposure was also tested with red and blue light from LED light sources and identical effects were observed. Exposure to green light did not have any effect, thus confirming the importance of excitation of the chlorophyllide.

Example 2: Thylakoids from Cyanobacteria as Electron Donor

The experiment was run as previously described with the exception of the replacement of chlorophyllin a with thylakoid membranes of marine cyanobacterium *Synechococcus* sp. PCC 7002 (hereafter *Synechococcus*). The thylakoids were isolated as previously described by Cardona et al. 2007 Physiol Plant. 2007 131(4):622-34, with a few exceptions being that the harvested cell pellets were resuspended in 1 ml citrate buffer (100 mM, pH 6.3) and cells were disrupted adding glass beads (500 µl) and using a cup horn sonicator (Amplitude 50, 3 min processing time, 5 sec on/off cycle, cooling 4 C). The thylakoid suspension was used directly without any ultracentrifugation steps. The buffer used was at pH 8 100 mM citrate-phosphate buffer in case of TfLPMOa, or pH 6.3 100 mM citrate-phosphate buffer for TtGH61E, and TaGH61A. 100 µL of PASO were added to 95 ul of thylakoids, and finally 2 µL of ascorbic acid and 1 µL of LPMO enzyme solution containing 10 µg enzyme (50 µg/ml final concentration). The physical parameters (temperature, shaking and light exposure) were as described in example 1.

Results

Figure 2:
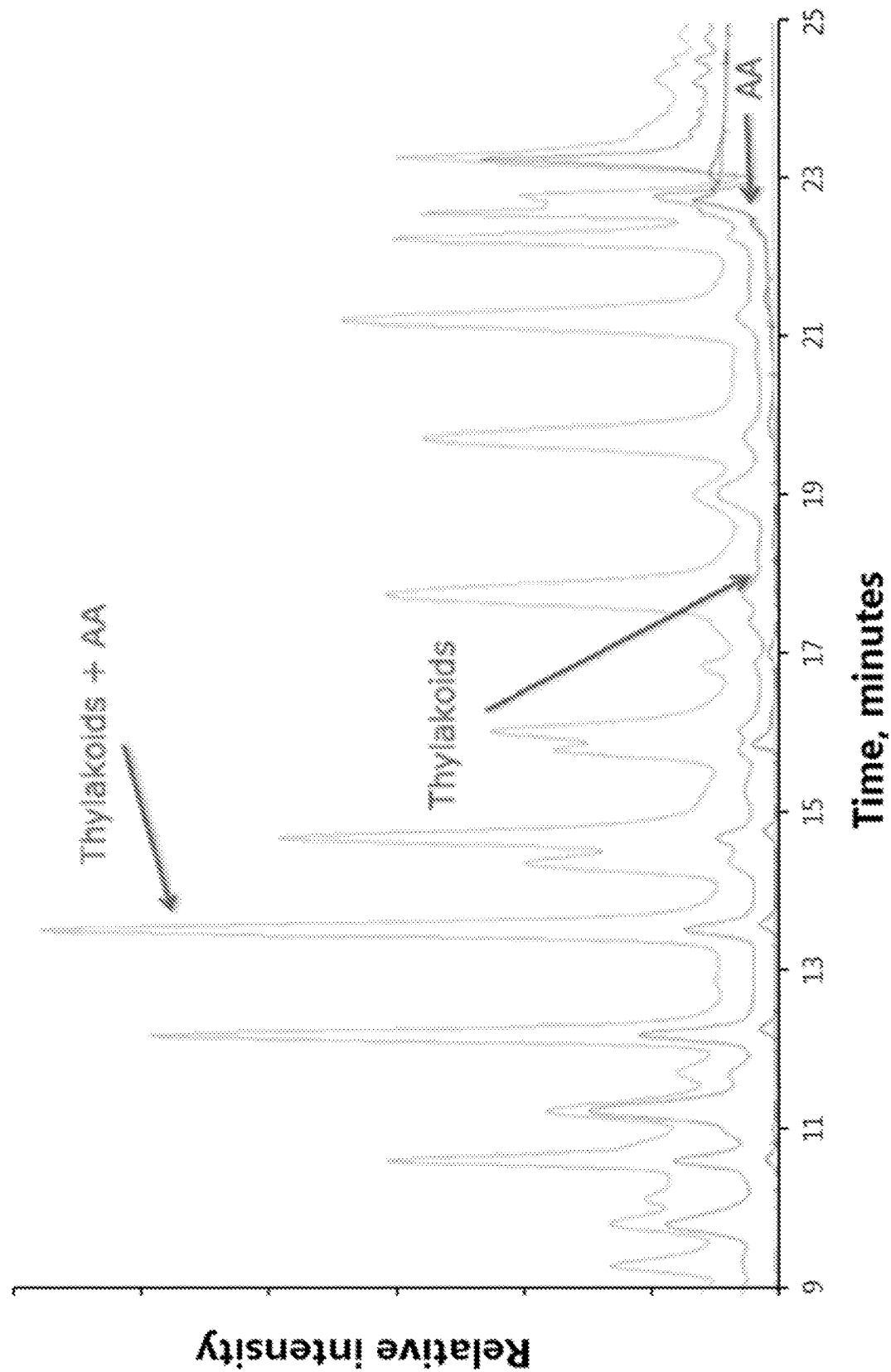
FIG. 2: HPAEC Chromatogram of LPMO treated PASC using thylakoids as electron donor and ascorbic acid as reductant compared to thylakoids or ascorbic acid only. All experiments were performed with 3 hours irradiation in sunlight. Thylakoids+AA: Thylakoids+ascorbic acid+LPMO. Thylakoids: Thylakoids+LPMO. AA: Ascorbic acid+LPMO.

The results are shown in FIG. 2. On the left side of the chromatogram are the reduced oligomers DP1 to DP6 and on the right side are the corresponding oxidisoxidised oligomers DP1 to DP6. Using thylakoids in combination with ascorbic acid and LPMO produces a similar effect as seen for the chlorophyllin. These data show that the transfer of excited electrons to the LPMO can be done with different kinds of light harvesting molecules or complexes.

Example 3: Lignin as Reductant

The ascorbic acid used as reductant in the previous experiment, was replaced with organosolv extracted lignin. The lignin fraction was prepared from wheat straw in several steps: First the wheat straw was hydrothermally treated for 19 minutes at 180° C. at 10% dry matter. From the treated material the cellulose and residual hemicellulose fractions were removed by means of hydrolytic enzymes (Celluclast, Novozyme 188) at final FPU of 75 units/gram of dry lignocellulose substrate for 144 hours at 50° C. followed by extensive washing. Finally the residual lignin was suspended in an aqueous ethanol solution (50:50 water to ethanol) at a 5:1 liquid to solid ratio and heated at 220° C. in a 1 L Parr reactor for 80 minutes. After cooking, the residue was filtered at 75° C. Solubilized lignin was precipitated by adding water at three times the original amount and recovered by filtration. The lignin-enriched fraction was dried (40° C.) and grinded with a pestle and mortar.

The organosolv lignin was suspended in citrate-phosphate buffer (either pH 8 or pH 6.3) at 50 mg/ml concentration, and 20 µL of this suspension was added to 100 µL of PASC. Then 75 µL of citrate phosphate buffer, 0.5 µL of chlorophyllin, and µL of LPMO enzyme containing 10 µg (50 µg/ml final concentration). The physical parameters (temperature, shaking and light exposure) were as described in example 1.

The control experiments were ascorbic acid+LPMO and lignin+LPMO, all other conditions identical.

Results

Figure 3:
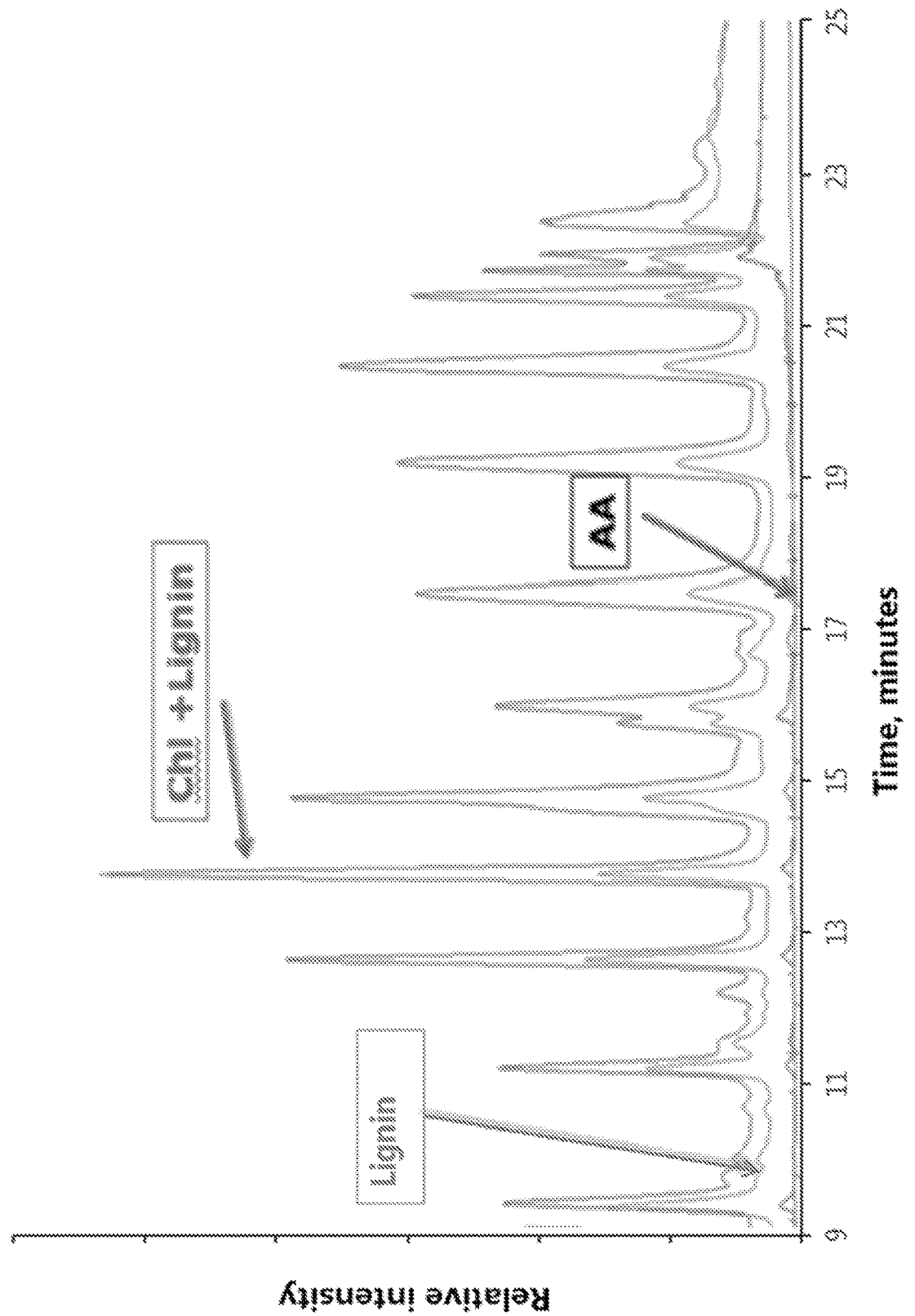
FIG. 3: HPAEC Chromatogram of LPMO treated PASC using lignin as reductant. All experiments were performed with 3 hours irradiation in sunlight. Chl+lignin: Chlorophyllin+lignin+LPMO. Lignin: Lignin+LPMO. AA: Ascorbic acid+LPMO.

The results are shown in FIG. 3. On the left side of the chromatogram are the reduced oligomers DP1 to DP6 and on the right side are the corresponding oxidisoxidised oligomers DP1 to DP6. From the chromatogram it can be seen that lignin functions as a reductant similar to what was observed for ascorbic acid in example 1. Note there is also a smaller effect from light exposure of the lignin+LPMO only. It can also be seen that the lignin itself can be excited by light exposure and transfer an excited electron to the LPMO active center. Thus a system comprising a catalyst such as an LPMO and lignin as light-harvesting molecule and as reductant can be applied.

Example 4: Kinetics and Stability

This experiment was performed with conditions identical to the conditions of example 1, except that the duration of light exposure was varied. The duration of light exposure was 10 minutes, 2 hours or 4 hours.

Results

Figure 4:
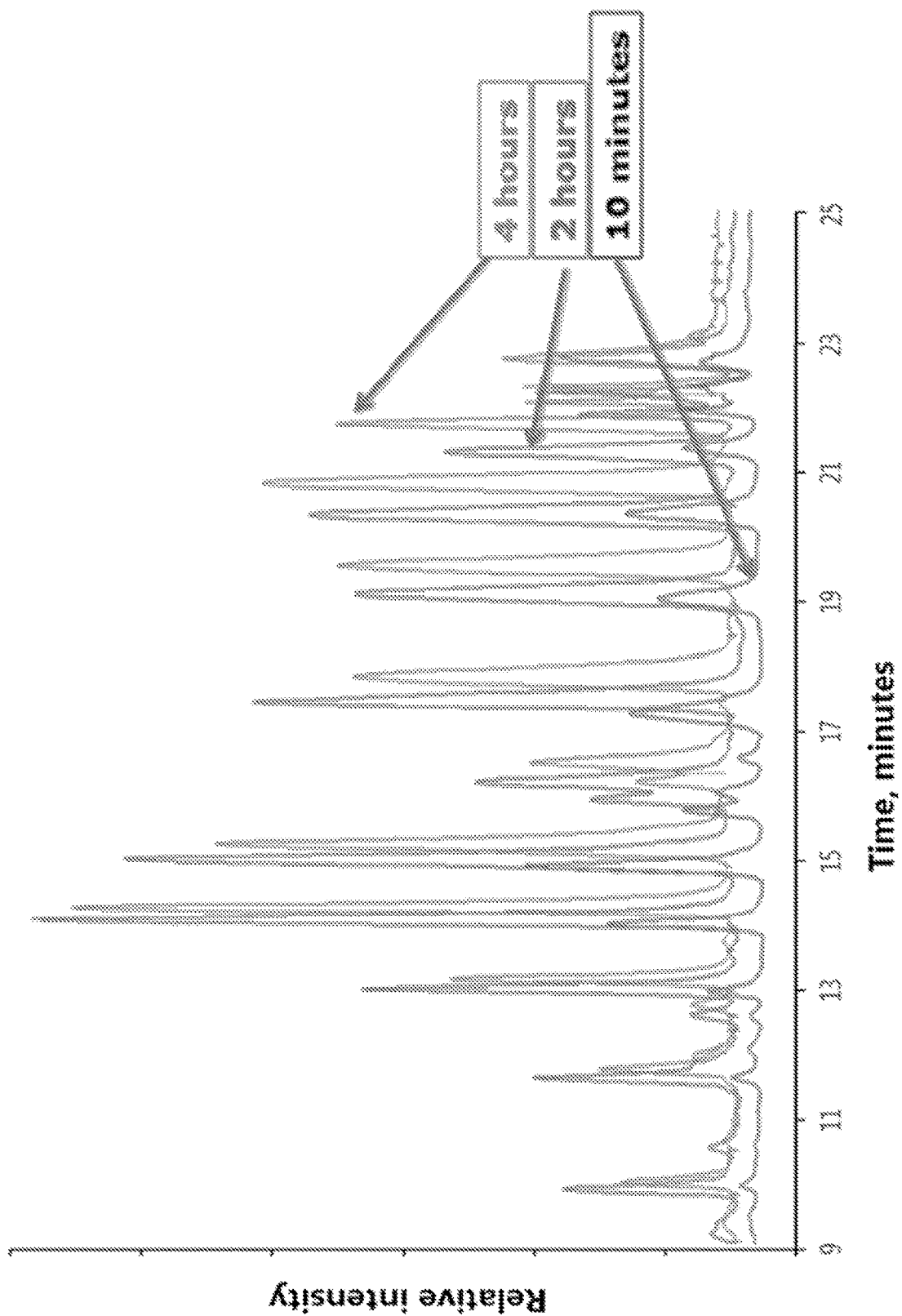
FIG. 4: HPAEC Chromatogram of LPMO treated PASC with different lengths of light exposure. Ascorbic acid was used as a reductant. Light exposure lasted 10 minutes, 2 hours or 4 hours.

The results show that a significant part of the reaction takes place already within 10 min (FIG. 4). Compared to a conventional setup using ascorbic acid and no light exposure, approximately 16 hours would be required to obtain the same level of products.

Also it can be seen that the level of products only increases marginally from 2 to 4 hours probably because the reaction is limited by the level of oxygen available to the LPMO.

Example 5: Materials and Methods

1. Chemicals, Materials and Polysaccharide Substrates

Ascorbic acid was obtained from Sigma Aldrich, Saint Louis, USA. Stock solutions of 100 mM were made in water and kept at −20° C. in the dark. Avicell microcrystalline cellulose was obtained from Sigma Aldrich, Saint Louis, USA. Xyloglucan product code P-XYGLN was obtained from Megazymes Ltd, Ireland.

PASC Microcrystalline Cellulose PASC Preparation

Avicell (microcrystalline cellulose, Sigma Aldrich PH101) was swollen with phosphoric acid to generate phosphoric acid swollen cellulose (PASC) as previously described by Wood et al., 1988 with a few modifications: 4 grams of Avicell were suspended in 100 mL of phosphoric acid (85% w/v) at 40° C. and magnetically stirred for 1 hour. The mixture was then poured into 1.9 L of water and kept at 40° C. with further stirring for 1 hour. The suspension was left stationary to allow the fibers to settle before decanting the supernatant. The suspension was washed four times with 2 L $H_2O$ (MilliQ-quality), two times with 2 L of a 1% $NaHCO_3$ solution to reduce acidity, and then three additional times with 2 L $H_2O$ (MilliQ-quality) and stored at 4° C. until further use. The final cellulose content of the PASC suspension was determined by enzymatic hydrolysis (24 hours, 50° C.), with a 75 FPU/g of Celluclast, 1.5 L cellulolytic enzymes and Novozyme 188 in a 5:1 ratio; followed by the determination of released glucose which lead to an estimated cellulose content of 1.5% w/v. The average DP of Avicell-derived PASO was determined by measuring the total number of reducing ends (Horn et al., 2004) and comparing this to the total amount of monomeric glucose, giving a degree of polymerization of 52.

Organosolv Lignin

The lignin fraction was prepared from wheat straw (*Triticum aestivum* L.). First, the wheat straw was ball milled for 20 minutes, then the cellulose and residual hemicellulose fractions were removed by hydrolytic enzymes (Celluclast, Novozyme 188 in a 5:1 v/v) at a final Celluclast FPU dosage of 75 units/gram of dry lignocellulose substrate for 144 hours at 50° C. followed by extensive washing. The amount of residual carbohydrates was less than 2% in the final material. Finally, the residual material was suspended in an aqueous ethanol solution (50:50 water to ethanol) at a 5:1 liquid to solid ratio and heated at 220° C. in a 1 L Parr reactor for 80 minutes. After heating, the lignin residue was filtered at 75° C. Solubilized lignin was precipitated by adding water at three times the original amount and recovered by filtration. The insoluble lignin fraction was dried (40° C.) and ground with a pestle and mortar.

Chlorophyllin

Chlorophyllin product code C-100.000-WS-P produced by extraction of *Festuca arundinacae* was obtained from Chr. Hansen, Hørsholm, Denmark. A stock solution of 12% w/v (166 mM) was prepared by dissolving the powder in water (MilliQ-quality). The chlorophyllin was kept in darkness while stored at 4° C. Prior to each experiment, an aliquot of the stock solution was incubated in darkness or dim green light for 2 hours at room temperature. The light absorbing capacity of chlorophyllin was stable over the whole duration of the experimental phase of this work.

The chlorophyllin product contained both Cu and Mg. The samples were analyzed for $^{24}Mg$, $^{25}Mg$, $^{26}Mg$ $^{63}Cu$ and $^{65}Cu$. Chlorophylline contained 0.41% Mg and 2.0% Cu relative to total dry matter. Thus therefore it is most likely a mixed product containing both chlorophyllin (Cu) and chlorophyllide (Mg) in the molecular ratio of 2:1.

Preparation of Cyanobacterial Thylakoid Suspensions

Thylakoid suspensions, containing light harvesting antennae (phycobilisomes) and thylakoid membranes, were prepared from the cyanobacterium *Synechococcus* sp. PCC 7002 (referred to as *Synechococcus*) grown in medium A containing 2 g $NO_3^-$ $L^{-1}$ as previously described (Holm-Hansen et al., 1978). The liquid 800 ml cultures were bubbled with a continuous flow of air supplemented with 1% (v/v) $CO_2$ provided by a gas mixer (GMS150, Photon Systems Instruments, Drasov, Czech Republic). Constant illumination was provided by fluorescent tubes (cool white light; Philips Master TL-D, 18 W/840; Philips Electronics, Amsterdam, The Netherlands) with 250 µmol photons $s^{-1}$ $m^{-2}$. *Synechococcus* cells were harvested in 50 ml volumes by centrifugation (5000 g for 5 min) and subsequently resuspended in 1 ml thylakoid washing buffer (pH 6.35) as described in Lichtenthaler et al., 2001. The resolved pellet was transferred to a microfuge tube containing 500 µl glass beads (glass beads for cell disruption, 0.1-0.25 mm diameter, Retsch Technology GMBH, Haan, Germany) followed by cell disruptive sonication (Amplitude 50, 3 min processing time, 5 sec. on/off cycle). The cell extract was then centrifuged (12 000 g, 4° C., 20 min) and the pellet, containing unbroken cells and cell walls was discarded. An additional centrifugation (40 000 g, 4° C., 30 min) separated the light harvesting antennae (phycobilisomes, supernatant) from the thylakoid membranes (pellet). Absorption spectra of the thylakoid suspensions in the supernatant were performed with a UV1800 spectrophotometer (Shimadzu, Kyoto, Japan) and the chlorophyll a content was calculated as described in Holm-Hansen et al., 1978. The thylakoid suspensions were then used to conduct the light induced electron transfer experiments with an average concentration of 0.21±0.06 mg Chl $ml^{-1}$. It is important to note that putative contaminations derived from cytoplasmatic membranes in the thylakoid suspension have no impact on light induced electron transfer to LPMOs which has been tested with disrupted *Escherichia coli* K-12 cells (data not shown).

Preparation of Plant Thylakoid Membranes

Plant thylakoid membranes were extracted from *Arabidopsis thaliana* (L.) Heynh. Ecotype Columbia. Plants were grown in compost in controlled environment *Arabidopsis* chambers (Percival AR-60 I, Boone, Iowa) at a photosynthetic flux of 130-150 µmol of photons $m^{-2}$ $s^{-1}$, 20° C., and 70% humidity. Leaves from approximately 25 plants were pooled and homogenized using a blender fitted with razor blades in ice cold buffer containing 20 mM Tricine (pH 7.5), 10 mM NaCl, 5 mM $MgCl_2$, 0.4 M sucrose, 5 mg $ml^{-1}$ bovine serum albumin (BSA) and 100 mM sodium ascorbate. The homogenate was immediately filtered through two layers of nylon mesh (31 µm pore size), after which the filtrate was centrifuged (6000 g, 4° C., 15 min). The pellet was resuspended in 5 mM Tricine (pH 7.9) in order to lyse the chloroplasts. Following lysis, the thylakoids were collected by centrifugation (17200 g, 4° C., 10 min). The pellet was resuspended in a small volume of homogenisation buffer without ascorbate and BSA but with 20% glycerol (v/v). Total chlorophyll (Chl) and Chl a/b ratio were determined in 80% acetone according to Lichtenthaler et al., 2001, and the final concentration of the thylakoid membranes applied in light induced electron transfer experiments was 3.57 mg Chl $mL^{-1}$ (Chl a/b ratio=3.0).

To ensure the thylakoid material was intact the viability of the extracted thylakoid suspensions was estimated by measurement of the variable chlorophyll fluorescence with a multicolor pulse-amplitude-modulated fluorometer (Heinz Walz GmbH, Effeltrich, Germany). Suspension samples were transferred to a 2 ml quartz cuvette and diluted with either thylakoid washing buffer (pH 6.35) or citrate phosphate buffer (pH 6.3) until a fluorescence signal of 500-800 mV was achieved. A Phyto-MS Miniature Magnetic Stirrer (Heinz Walz GmbH, Effeltrich, Germany) was used to ensure homogenous distribution of the sample in the cuvette. A pulse modulated red measuring light (625 nm) with an intensity of <1 µmol $m^{-2}$ $s^{-1}$ and a frequency of 10 Hz was used. A red light saturation pulse of 5000 µmol $m^{-2}$ $s^{-1}$ was applied for 0.6 sec. A long pass filter (RG 665, Heinz Walz GmbH, Effeltrich, Germany) was attached to the instrument fluorescence detector. Variable chlorophyll fluorescence has been measured as the effective photochemical quantum yield Y(II) as described in Genty et al., 1989.

2. Enzymes

Purified *Thielavia terrestris* LPMO (TtLPMO9E, previously TtGH61E) (Harris et al., 2010) and *Thermoascus auranticus* (TaLPMO9A) (Quinlan et al., 2011) were donated from Novozymes A/S (Denmark) The enzymes were produced by expression in a host organism and subsequently purified.

*Thermobifida fusca* AA10 (TfLPMO10A) cloned and expressed in *E. coli* was purchased from Nzytech Ltd (Portugal). All LPMOs were free of any residual cellulase or hemicellulose activities.

Commercial cellulase mixtures Celluclast 1.5 L and Novozyme 188 were obtained from Novozymes A/S, Denmark. The Celluclast 1.5 L mixture had a protein content of 127 mg/g, containing 62 FPU/g cellulase activity and 15 U/g β-glucosidase activity. Novozyme 188 had a protein content of 220 mg/g, containing 231 U/g β-glucosidase activity. Pure β-glucosidase was obtained from Megazyme Ltd, Ireland.

3. Characterization of Photoabsorbing Complexes

Visible Light/UV-Spectrophotometer

Chlorophyllin and thylakoids were analyzed from 350 to 850 nm with a Shimadzu UV-2550 spectrometer.

Elemental Analysis ICP

Chlorophyllin and thylakoids were analyzed for the presence of metals on an Aurora Elite ICP-MS system from Bruker. Samples of chlorophylline 12% (w/w) and extracted thylakoid suspensions 2% (w/w) were diluted to 500-1000 ppb dry matter in 1% nitric acid. The samples were analyzed for $^{24}Mg$, $^{25}Mg$, $^{26}Mg$ $^{63}Cu$, $^{65}Cu$, $^{66}Zn$, $^{67}Zn$ and $^{68}Zn$. Chlorophylline contained 0.41% Mg, 2.0% Cu and 0.05% Zn relative to total dry matter. Extracted thylakoid suspensions contained 1.8% Mg, 0.007% Cu and 0.0007% Zn relative to total dry matter.

4. Product Analysis by HPLC and HPAEC

Measurement of Glucose and Cellobiose by High Performance Liquid Chromatography (HPLC)

The quantification of D-glucose and D-cellobiose was done using an Ultimate 3000 HPLC (Dionex, Germering, Germany) equipped with refractive index detector (Shodex, Japan) and UV detector at 210 nm (Dionex). The separation was performed in a Phenomenex Rezex ROA column at 80° C. with 5 mM $H_2SO_4$ as eluent at a flow rate of 0.8 ml/min.

Measurement of Polysaccharide Oligomers and Gluconic Acid by High-Performance Anion-Exchange Chromatography (HPAEC)

The samples were prepared as follows: 200 µl were centrifuged at 14000 g for 2 min and 100 µl of the supernatant was inserted in the HPLC conical vial without any further light exposure (wrapped in aluminum foil).

HPAEC was run on an ICS 5000 system, equipped with a PAD detector (Dionex, Sunnyvale, Calif., USA) set up with a CarboPac PA1 column (2×50 mm guard column followed by a 2×250 mm analytical column) operated at a flow of 0.25 mL/min, at 30° C. Chromatography for aldonic acids separation was conducted as described in (Westereng et al., 2013). In short, elution involved a linear gradient from 100% A:0% B to 90% A:10% B (10 min), followed by an exponential gradient to 70% A:30% B (15 min), and lastly an exponential gradient to 100% B (5 min). After that a linear gradient was run for 15 minutes at the initial conditions 100% A:0% B (eluent A=0.1 M NaOH, B=0.1 M NaOH and 1 M NaOAc).

Quantification of Total Cellulose Oxidation for TtLPMO9E (FIG. 5C)

Light induced oxidation samples (chlorophyllin) were also used for the quantification of the total aldonic acids derived from cellulose oxidation. The remaining un-hydrolyzed PASC, together with the supernatant rich in oligosaccharides were digested with a commercial cellulase mixture, Celluclast supplemented with beta-glucosidase N188 in a 5:1 v/v ratio (both lacking of LPMO activity) dosed based on Celluclast at 75 FPU/gram cellulose for 5 hours at 50° C. in darkness. These conditions assured a complete hydrolysis of the whole PASC material. The LPMO reaction was stopped before cellulases treatment by boiling the vials for 10 minutes. The hydrolyzates were then analyzed by HPLC to quantify the D-glucose and in the HPAEC for quantification of gluconic acid (marker of C1 oxidisoxidising activity of LPMO). A minor C4 component (annotated C4-oxidisoxidised after minute 24) appeared in the oxidisoxidised products; unfortunately it was impossible to quantify the amount of the monomeric 4-keto aldose sugar (abbreviated C4 oxidisoxidised glucose).

5. Enzymatic Reactions

The standard experimental reaction mixtures for PASC cellulose oxidation via AA9 enzymes (TtLPMO9E and TaLPMO9A) were composed of: 1.5% w/v PASC, 2 mM ascorbic acid, 100 mM of citrate-phosphate buffer (pH 6.3), 0.05 mg $mL^{-1}$ LPMO in a 200 µL reaction volume. In case of the AA10 (TfLPMO10A), a phosphate buffer was set to pH 7.8 (20 mM). Chlorophyllin was added in a 1:100 dilution out of a 12% stock solution. Freshly prepared cyanobacterial thylakoid suspensions and plant thylakoid membranes were diluted into the reaction mixture 1:2 and 1:20 respectively.

In experiments using organosolv lignin as an alternative reductant (instead of 2 mM of ascorbic acid), lignin was added to a final concentration of 5 mg mL$^{-1}$, equal to a molar concentration of 25 mM based on lignin monomers. All experimental preparations were carried out in darkness or dim green light. The reaction mixtures were exposed to light at different wavelengths (custom made LED for blue light: 440 nm and red light: 625 nm, Phillips TL-D 36W color green Lumen 3600 for green light: 540 nm and sunlight) and identical irradiation intensities for blue and red light of 150-200 μmol of photons m$^{-2}$ s$^{-1}$ while green light exposures were carried out at a lower intensity of 50 μmol of photons m$^{-2}$ s$^{-1}$. The irradiance intensities were measured at the bottom of the closed Eppendorf test tubes. Irradiation was measured by inserting a light probe from a Spherical Micro Quantum Sensor US-SQS/Lund. The incubation time was 3 hours unless otherwise stated. For each experiment an LPMO activity control independent of either light absorbing components or light irradiance was incubated with ascorbic acid, PASO and the tested LPMO respectively. The experiments were carried out in 2 mL Eppendorf polypropylene microfuge tubes in an Eppendorf thermomixer (Eppendorf, Hamburg, Germany) operated at 1000 rpm and 50° C. The thermomixer was modified to host a transparent microfuge rag for light penetration through the walls of the microfuge tubes. Sunlight exposure was done by placing the thermomixer in the window in the period of June-July in Copenhagen at a latitude of 55° 41'N.

Light Induced Electron Transfer to LPMO Using the Individual Components of the System The feasibility of light induced electron transfer from the individual components of the system was investigated. Therefore chlorophyllin and cyanobacterial thylakoid suspensions were incubated with PASO, TtLPMO9E and citrate-phosphate buffer (pH 6.3) and exposed to light at different wavelengths and identical irradiance intensities (see enzymatic reactions). It is important to note that these incubations were carried out without available reductant (ascorbic acid). In addition, either the tested LPMO alone or LPMO+ascorbic acid were incubated with PASO and citrate-phosphate buffer (pH 6.3). Once the incubation was stopped, all sample vials were wrapped in aluminum foil and kept in darkness until further analysis. All incubated samples were analyzed for oligosaccharide products derived from LPMO activity with HPAEC. In this experiment all available LPMO's (see enzymes) were tested.

6. Protein Structure Modelling

The PDB structures from the RCSB PDB Protein data bank were adapted for the HARLEM-Molecular Modeling Package program (Kurnikov, I. et al, available at harlem.chem.cmu.edu. The PDB structures were (after adding hydrogens) analyzed in HARLEM for possible LRET pathways from the surface to the metal ion (Onuhic et al., 1992).

Example 6—Light-Induced Electron Transfer Requires Chlorophyll Pigments

To investigate the activity of the LPMOs we used phosphoric acid swollen cellulose (PASO) as substrate and detected the released oligomeric products by chromatography. To this mixture, different sources of photosynthetic pigments were added to test their function as electron donors. The effect of exposure to light sources at varying intervals was analyzed.

Initially the feasibility of light-induced electron transfer to an LPMO from *Thielavia terrestris* (TtLPMO9E) was tested in combination with a thylakoid suspension from cyanobacteria (*Synechococcus* sp. PCC 7002) and exposure to sunlight. This induced some activity of the LPMO enzyme (FIGS. 5A and 9). To re-reduce the oxidisoxidised pigments to the ground state in the thylakoid suspension, ascorbic acid was added as reductant. This resulted in a tremendous change in the reaction rate and amount of oxidisoxidised products (FIG. 5A). Performing the same experiment in green light resulted in no oxidation of the cellulose and using ascorbic acid only did not show any response to the light exposures. Using thylakoid membranes from *Arabidopsis thaliana* similar results were observed.

To investigate whether the excitable pigment indeed was chlorophyll, we tested the water-soluble chlorophyll derivative chlorophyllin in the LPMO-assays with cellulose. This resulted in even more pronounced accumulation of oxidisoxidised products upon light exposure (FIG. 5B), suggesting that chlorophyll-pigments indeed are the main component responsible for the light induced electron transfer. Further details of light exposure can be seen in FIGS. 9 and 10.

Identical light induced electron transfer was observed in experiments with chlorophyllin and two other LPMOs from *Thermobifida fusca* (TtLPMO10A) and *Thermoascus aurantiacus* (TaLPMO9A), respectively (FIGS. 11 and 12).

The light induced electron transfer system was also examined with crystalline cellulose as substrate, and similar conversions were observed (FIG. 13).

These data show that cellulose can be oxidxed using chlorophyllin and LPMOs with a high reaction rate.

Example 7—Light Source

To further verify the effect of light on the LPMO catalyzed reaction, the response to different light sources was investigated. Consequently the experiments were performed in blue, red and green light. In accordance with the absorption spectra of chlorophyll pigments only blue, red and white (i.e. sunlight) light incubation induced oxidation of the cellulose substrate (FIG. 5C). A sequential light response experiment with alternating green light and sunlight further proved that light activates the oxidation of cellulose as cycles of green light for 2 hours and sunlight for 5 minutes switch the reaction on and off (FIG. 5D and FIG. 14).

The amounts of oxidisoxidised products during a 3 hour light induced electron transfer reaction (FIG. 5C) shows that approximately 10% of the cellulose was oxidisoxidised in the light driven systems compared to 0.5% with ascorbic acid and sunlight only. Using ascorbic acid as the single electron donor for 24 hours oxidisoxidised only 1.8% of the cellulose. The observed levels of cellulose oxidation catalyzed by light induced electron transfer and LPMOs are to the best of our knowledge higher than any previously reported result on LPMO oxidation of polysaccharides (Cannella et al., 2012; Rodrigues-Zuniga et al., 2015).

The effect of the presence or absence of light was also investigated. When the system is placed in darkness, no oxygen is consumed by a system comprising chlorophyllin, ascorbic acid, *T. terrestris* LPMO and PASC. Activation of the light source (at 900 seconds in FIG. 6A) results in a stable oxygen consumption by a complete system. It is worth of notice that a system deprived either of LPMO or of chlorophyllin does not consume oxygen even when the system is placed in light. It is also striking that the system is very stable, as illustrated by the slope of the curve, and that it is active until depletion of oxygen.

Another experiment was performed, where a system comprising *T. terrestris* LPMO, ascorbic acid and PASO was placed under an intermittent light source, i.e. alternatively in light and darkness at intervals of 120 seconds. No oxygen is consumed before the addition of chlorophyllin at 700 seconds. Oxygen consumption then starts when the system is placed in light. As soon as the system is placed in the dark, oxygen consumption stops, only to resume the next time the light is turned on (FIG. 6A).

Example 8—Reductant

To test the stability of the chlorophyllin with or without the reductant we measured the absorption spectrum of the assay mixture after 3 hours exposure to sunlight. The absorption values indicate that the reductant protects the chlorophyllin (FIG. 7B). Continuing the light exposure after 3 hours with TtLPMO9E and chlorophyllin and adding more cellulose substrate and ascorbic acid, showed that the activity of the enzyme and chlorophyllin was maintained.

Lignin extracted from wheat straw functions equally well as reductant compared to ascorbic acid (FIG. 8A).

These data show that the present system is highly stable, and that lignin can be used as a reductant.

Example 9—Modulation of LPMO Activity

Surprisingly, the specificity of the *Thielavia terrestris* LPMO changes when subjected to light induced electron transfer. This LPMO is known to be strictly cellulose specific when used with ascorbic acid as electron donor. However, combined with light induced electron transfer the enzyme oxidisoxidises not only crystalline cellulose but also xyloglucan (FIG. 8B). The oxidation of xyloglucan and a broader substrate specificity have been reported for a LPMO from *Neuspora crassa*, (Antonova et al., 2005) and by a LPMO from Podospora anserine (Bennati-Granier et al., 2015), both enzymes oxidisoxidises glucans and xyloglucans. The degradation pattern of xyloglucan in FIG. 8B is similar to the degradation pattern of oxidisoxidised xyloglucan previously reported (Bennati-Granier et al., 2015).

The changes in enzyme specificity observed with light induced electron transfer are pronounced and suggest that the type of electron donor and the energy of the reducing electron can modulate the activity of the LPMO.

Example 10—Kinetics

Determination of the kinetics for LPMO enzyme reactions is difficult due the heterogeneous mixture of reaction products, just as the exact mechanism of the active site is still under investigation. Low turnover rates from 0.01-0.04 $s^{-1}$ have been estimated (Borisova et al., 2015), but until now no complete kinetic parameters of any LPMO have been reported. Using ascorbic acid and CDH as electron donors, a steady state level of oxidisoxidised products is reached after 24-36 hours (Cannella et al., 2012, Bennati-Granier et al., 2015). With light induced electron transfer the level of oxidisoxidised cellulose was 2.1% after 10 minutes (FIG. 5D) compared to 1.8% oxidisoxidised cellulose with ascorbic acid only after 24 hours using the same assay. It is thus possible to achieve the same level of oxidation in less than a hundredth of the time required without light-induced electron transfer. These data are also supported by the LPMO turnover frequency determined to be 0.25 $s^{-1}$ based on the oxygen consumption when incubated with the photosystem at 25° C. (FIG. 6a) and 0.55 $s^{-1}$ at 50° C. based on the accumulation of oxidised product after two cycles of 5 min light exposure (FIG. 5d). Previously published turnover values for an *N. crassa* LPMO by measuring reducing ends of oxidised PASO at 50° C. were 0.01-0.04 $s^{-1}$. The reaction rates and product levels observed for LPMOs with light induced electron transfer are one or more orders of magnitude higher, than what was previously known.

Example 11—Model

Without being bound by theory, we propose an overall redox cycle for photodegradation as shown in FIG. 7A. The light excites an electron in the light harvesting molecule. When the electron(s) are transferred from chlorophyllin to LPMO following a photon absorption event, it generates a radical charged form of chlorophyllin, $Chl^+$, which is a highly potent oxidisoxidising agent capable of abstracting electrons from the reducing agents. The described reaction would exhaust its potential, if the chlorophyllins were left in their radical form, performing only a single event of photon absorption/electron donation. Ascorbic acid has a stabilizing effect on chlorophyll and by adding a reducing agent the ground state of chlorophyllin is restored, and it can complete another cycle.

Example 12—Enhanced Cellulose Hydrolysis by Combining Light Driven Oxidation Using Chlorophyllin as Light Harvesting Molecule with a CBH II Cellulase This example shows enhanced cellulose hydrolysis by combining light driven oxidation using chlorophyllin as light harvesting molecule with a CBH II cellulase.

Figure 16A:
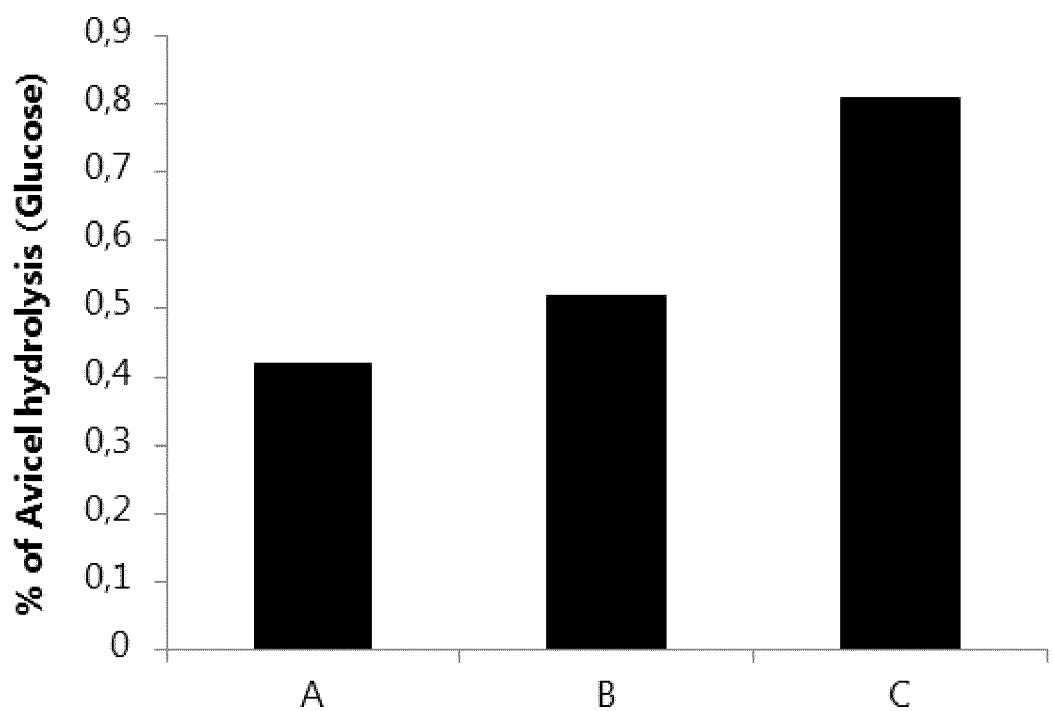
Figure 16B:
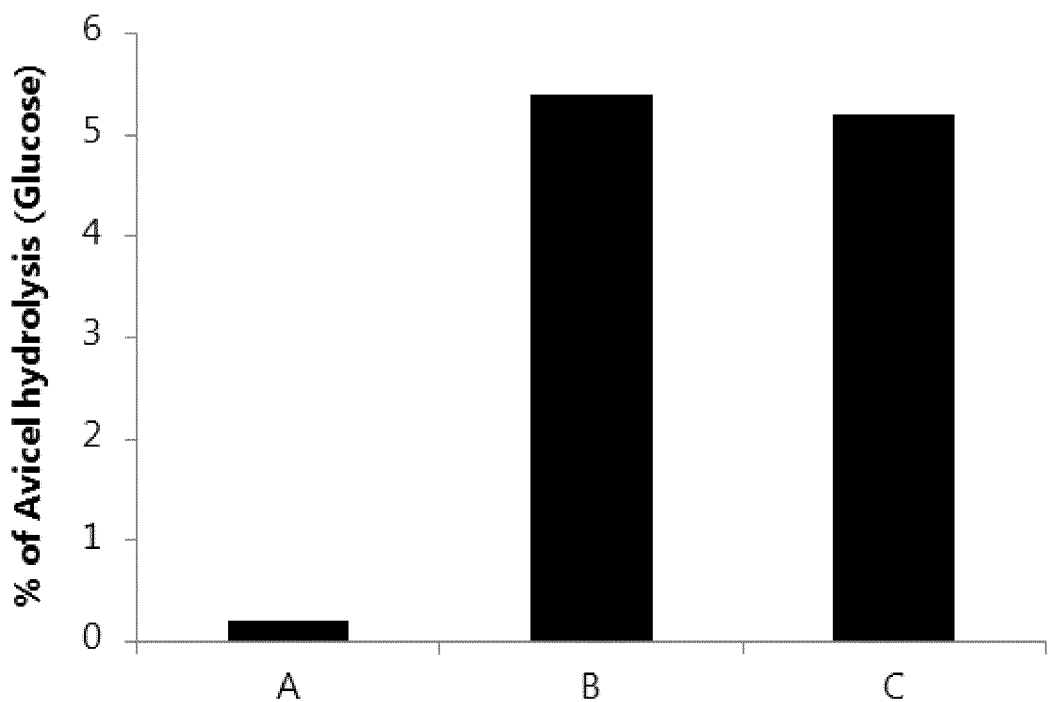

The light harvesting molecule and enzyme electron donor was chlorophyllin, the LPMO was a TtLPMO9E and the reductant for the light harvesting molecule as ascorbic acid. FIG. 16A shows the yield of enzymatic hydrolysis of Avicel after 24 hours with CBHII or light induced electron transfer based on chlorophyllin.

Example 13—Enhanced Cellulose Hydrolysis by Combining Light-Induced Electron Transfer Using Thylakoids as Light Harvesting Complex with a CBH II Cellulase The light harvesting molecules and enzyme electron donor was thylakoids, the LPMO was a TtLPMO9E and the reductant for the light harvesting molecule was ascorbic acid.

The example shows that compared to CBH II+LPMO (example 12, FIG. 16A) the level of hydrolysis was increased by a factor of 10 (FIG. 16B) when thylakoids were used as light harvesting molecule or complex. The use of catalase had no effect upon the light-induced electron transfer-cellulase synergy, probably because the thylakoids are capable of scavenging hydrogen peroxide that can be generated by the LPMO in a futile cycle.

Example 14—Enhanced Cellulose Hydrolysis by Combining Light-Induced Electron Transfer Using Thylakoids as Light Harvesting Complex with a CBH I Cellulase The light harvesting molecules and enzyme electron donor was thylakoids, the LPMO was a TtLPMO9E and the reductant for the light harvesting molecule was ascorbic acid.

The example shows that also for CBH I, using light induced electron transfer resulted in an increase of the level of hydrolysis by approximately 20% (FIG. 17, compare bar C to bar B).

Example 15—Effect of Light Intensity

Avicel cellulose was hydrolyzed with CBHII at different light-wavelengths in the light-induced electron transfer system based on thylakoids. One reaction (FIG. 18, bar A) contained substrate, CBHII, betaglucosidase, TtLPMO9E, ascorbic acid and thylakoids and was exposed to blue and red light simultaneously at total intensity of 200 µmol per second. The other reaction (FIG. 18, bar B) contained the same substrate, CBHII, betaglucosidase, TtLPMO9E, ascorbic acid and thylakoids and was exposed to red light only at 170 µmol per second. The remaining experimental conditions were as described in examples 13 and 14: 0.1M citric acid buffer pH 5. LPMO dosage 10 mg/g substrate. CBH II dosage 10 mg/g substrate. Thylakoids 0.35 mg/ml. Ascorbic acid 1 mM.

The example shows that the highest effect of light-induced electron transfer is obtained when red light is used at an intensity of 170 µmol per second as compared to light of a higher intensity and with a blue light component.

Example 16—Cellulose Hydrolysis—Multi Component Cellulase Enzyme Cocktail

In this example light-induced electron transfer was combined with the Celluclast+NZ 188 multicomponent cellulase cocktail on an Avicel substrate in order to compare a commercial cellulase cocktail (Celluclast+NZ188 βGlucosidase in a 5:1 ratio) and combinations of light-induced electron transfer based on thylakoids and TtLPMO or TaLPMO and red light at 170 µmol per second. The light harvesting molecule and enzyme electron donor was chlorophyllin, the LPMO was TtLPMO9E or TaLPMO, and the reductant for the light harvesting molecule was ascorbic acid.

The results (FIG. 19) show the yield of enzymatic hydrolysis of Avicel substrate.

Experimental conditions pH 5 0.1M citric acid buffer. LPMO dosage 10 mg/g substrate. Celluclast+NZ188 dosage 10 mg/g substrate. Thylakoids 0.35 mg/ml. Ascorbic acid 1 mM. Light intensity 170 umoles per second.

The example shows that using light-induced electron transfer increased the level of cellulose hydrolysis by approximately 40% compared to Celluclast+LPMO without light-induced electron transfer (compare bars C, D and E to bars A and B). In this example the highest level of synergy was obtained when using a TaLPMO. The choice of LPMO for optimal effect can vary with the type of substrate, the light harvesting molecule or complex and the composition of the enzyme cocktail.

Example 17—Cellulose Hydrolysis—Light-Induced Electron Transfer and Cellulases Using an Intermittent Light Source The enzymatic cocktail in this reaction contained CBHI, CBH II and Beta-Glucosidase. Intermittent light means a cycle of 10 seconds of red light at 170 µmoles s−1 intensity followed by 50 seconds of darkness. Full light is red light at 170 µmoles s−1 intensity for the duration of the experiment. The results (FIG. 20) show that using intermittent light can enhance the synergy between light induced electron transfer and cellulases. The relatively low level of hydrolysis is caused by the experiment being done at pH 6, above the pH optima of the enzymes.

Experimental conditions pH 6 0.1 M citric acid buffer. LPMO dosage 10 mg/g substrate. CBH I+CBH II dosage 10 mg/g substrate. Thylakoids 0.35 mg/ml. Light intensity 170 µmoles per second.

Example 18—Light-Induced Electron Transfer on Natural Substrate: Cotton

This example shows how light-induced electron transfer performed on a non-modified natural cellulose substrate. The effect of light-induced electron transfer (FIG. 21) was equal to what can be observed using the modified cellulose Avicel as a substrate.

Experimental conditions pH 6.3 0.1M citric acid buffer. LPMO dosage 10 mg/g substrate. Chlorophyllin 1.6 mM. Light intensity 170 µmoles per second.

Figure 22B:
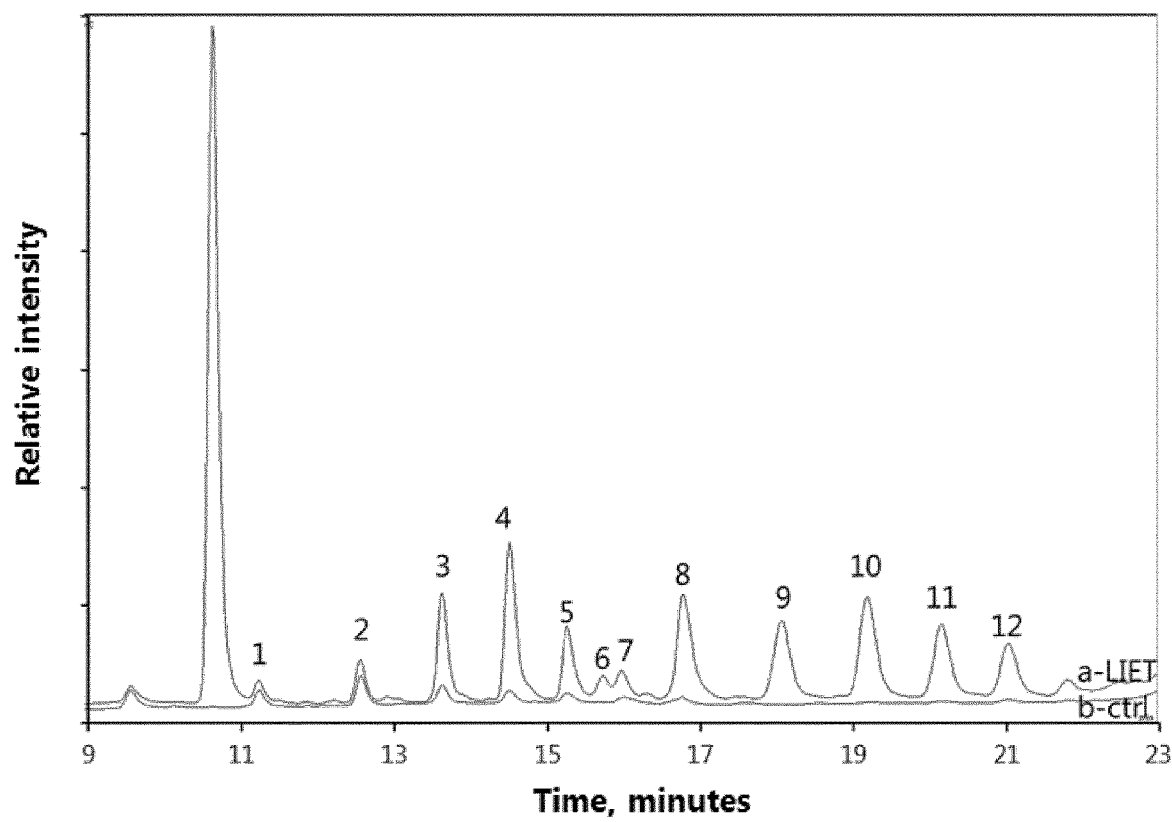

Example 19—Effect of Nature of Reducing Agent on Light-Induced Electron Transfer 1 mM ascorbic acid was replaced by 1 mM gallic acid (FIG. 22A) or 1 mM ferulic acid (FIG. 22B). Experimental conditions: pH 6.3 0.1M citric acid buffer. LPMO dosage 10 mg/g substrate. Chlorophyllin 1.6 mM. Light intensity 170 µmoles per second.

The results show that gallic acid and ferulic acid performed equally well or better than ascorbic acid.

Example 20—Combining Light Induced Electron Transfer with Other Methods for Cellulose Oxidation-Combination with TEMPO Oxidation Experimental conditions pH 6 0.1M citric acid buffer. LPMO dosage 10 mg/g substrate. Chlorophyllin 1.6 mM. Light intensity 170 µmol per second.

This example shows how light induced electron transfer can be combined with other methods for oxidation of cellulose. Whatman no. 1 filter paper was oxidisoxidised by TEMPO to a level of 2% oxidation. The TEMPO oxidisoxidised filter paper (cellulose) produces C2 or C6 oxidisoxidised cellulose and was combined with LPMO only or light induced electron transfer. The combination of TEMPO and LIET produced a multitude of oxidisoxidised oligomers, which were not present when the methods are applied separately (FIG. 23).

Example 21—Conversion of Methane to Methanol 5 ml GC vials were flushed with methane and closed. Chlorophyllin, ascorbic acid and buffer were added with (LIET) or without (negative controls) TfLPMO to a total volume of 1 mL before injecting 1 mL of $O_2$. Blue and red light was applied at an intensity of 200 µmol of photons per second. The vials were shaken at 400 RPM for 24 hours under irradiance and the methanol was detected by GC.

Negative controls, performed in the absence of enzyme, with buffer, pigments and ascorbic acid only: 0.5-0.9 ppm of methanol.

LIET, performed with TfLPMO, chlorophyllin, and ascorbic acid: 2.5 ppm methanol.

REFERENCES

Antonova, Chaplygina, Varaksina, Stasova. Ascorbic acid and xylem development in trunks of the Siberian larch trees. *Russian J. Plant Physiology* 52 83-92 (2005) Balzani et al. Acc. Chem. Res., 1998, 31 (1), pp 26-34

Bennati-Granier et al, Substrate specificity and regioselectivity of fungal AA9 lytic polysaccharide monooxygenases secreted by Podospora anserine. *Biotechnol. Biofuels.* 8, 90 (2015)

Cannella, Möllers, Frigaard, Jensen, Bjerrum, Johansen, Felby. Light-driven oxidation of polysaccharides by photosynthetic pigments and a metalloenzyme. Nat Commun. 7:11134 (2016)

Cannella et al. Production and effect of aldonic acids during enzymatic hydrolysis of lignocellulose at high dry matter content. Biotechnology for Biofuels 5° 26B (2012)

Caputo, Wang, Beranek & Reisner. Carbon nitride-$TiO_2$ hybrid modified with hydrogenase for visible light driven hydrogen production. Chem. Sci. 6, 5690-5694 (2015).

Chaudhary, Woolerton, Allen, Warner, Pierce, Ragsdale, Armstrong. Visible light-driven CO2 reduction by enzyme coupled CdS nanocrystals. *Chem Commun (Camb).* 48(1):58-60

Genty, Briantais, Baker. The relationship between the quantum yield of photosynthetic electron transport and quenching of chlorophyll fluores-cence. *Biochim Biophys Acta* 990, 87-92 (1989)

Harris et al, Stimulation of Lignocellulosic Biomass Hydrolysis by Proteins of Glycoside Hydrolase Family 61: Structure and Function of a Large, Enigmatic Family. *Biochemistry-Us* 49, 3305-3316 (2010)

Hemsworth, Henrissat, Davies, and Walton. *Discovery and characterization of a new family of lytic polysaccharide monooxygenases.* Nat Chem Biol. 2014 February; 10(2): 122-6.

Holm-Hansen, Riemann. Chlorophyll a Determination: Improvements and Methodology. *Oikos* 30 438-447 (1978)

Horn, Eijsink, A reliable reducing end assay for chitooligosaccharides. *Carbohyd Polym* 56, 35-39 (2004).

Lichtenthaler, Buschmann. Chlorophylls and Carotenoids: Measurement and Characterization by UV-VIS Spectroscopy. *Cur. Protocols in Food Analyt. Chem.*, DOI: 10.1002/0471142913.faf0403s01 (2001)

Onuchic, Beratan, Winkler, Gray. Pathway analysis of protein electron-transfer reactions. *Annu Rev Biophys Biomol Struct.* 21, 349-377 (1992)

Quinlan et al, Insights into the oxidative degradation of cellulose by a copper metalloenzyme that exploits biomass components. *Proc. Nat Acad. Sci.* 108 1579-1584 (2011)

Rodrigues-Zuniga et al, Lignocellulose pretreatment technologies affect the level of enzymatic cellulose oxidation by LPMO. *Green Chem.* 17 2896-2903 (2015)

Westereng et al. Efficient separation of oxidisoxidised cello-oligosaccharides generated by cellulose degrading lytic polysaccharide monooxygenases. *Journal of chromatography. A* 1271, 144-152 (2013)

Wiselogel of al., 1995, in "Handbook on Bioethanol" (Charles E. Wyman, editor), pp. 105-1 18

Wood, Preparation of Crystalline, Amorphous, and Dyed Cellulase Substrates. *Method Enzymol* 160, 19-25 (1988).

Ziessel et al, J. Am. Chem. Soc., 2013, DOI: 10.1021/ja4049306

The invention claimed is:

1. A method for chemical modification of an organic substrate, said method comprising the steps of:
   i. providing an organic substrate; and
   ii. contacting said organic substrate with a non-naturally occurring system comprising:
   (a) a light source,
   (b) a light harvesting molecule or organelle,
   (c) at least one enzyme and
   (d) a reductant and/or an electrochemical electrode;
   wherein the at least one enzyme is a lytic polysaccharide monooxygenase (LPMO) belonging to the AA9, the AA10, the AA11 or the AA13 family and wherein the organic substance and the (b)-(d) are provided as a single continuous volume of fluid, thereby the organic substrate is chemically modified.

2. The method according to claim 1, further comprising the step of providing oxygen and/or hydrogen peroxide to said non-naturally occurring system contacted with said organic substrate, in a quantity that the oxygen and/or hydrogen peroxide are not limiting the chemical modification.

3. The method according to claim 1, wherein the system has a positive redox potential relative to a standard hydrogen electrode, of at least 0.1 V or more.

4. The method according to claim 1, wherein the light harvesting molecule is a part of a complex.

5. The method according to claim 1, wherein the light harvesting molecule or organelle is a chlorophyll, a bacteriochlorophyll, a phycobilisome, a phycobilin, a chlorophyllin, a chlorophyllide, a thylakoid membrane, a chloroplast, a chlorosome, a rhodopsin, a carotenoid, an anthocyanin, a bilirubin, a luciferin, a xanthophyll, a flavonoid, a porphyrin, a polyene enolate, or a combination thereof.

6. The method according to claim 1, wherein the reductant is a water-soluble reductant selected from the group consisting of ascorbic acid, a lignan, a hydroquinone, 2-(20-hydroxyphenyl)benzothiazole, 3-hydroxyanthranilic acid, a technical lignin, lignosulfonate or at least one fraction thereof, a ferulic acid, a gallic acid and a caffeic acid, or wherein the reductant is an insoluble reductant selected from the group consisting of native lignin, kraft lignin, organosolv lignin, and at least one fraction thereof.

7. The method according to claim 1, wherein the reductant has a redox potential higher than a redox potential of lignin or wherein the reductant has a redox potential lower than a redox potential of ascorbic acid; wherein the redox potential of the reductant, the redox potential of lignin, and the redox potential of ascorbic acid are relative to same standard electrode.

8. The method according to claim 1, wherein the organic substrate comprises a polysaccharide, a carbohydrate, a chitin, a starch, a protein, a lipid or a hydrocarbon having a straight or a branched chain $C_1$-$C_n$, where n is an integer; an aromatic hydrocarbon, an alkane, an alkene, a cycloalkane or an alkyne-based compound; carboxymethyl cellulose, cellulose nanofibers, oxidised cellulose, oxidised cellulose nanofibers, (2,2,6,6-Tetramethylpiperidin-1-yl)oxyl-oxidised cellulose, (2,2,6,6-tetramethylpiperidin-1-yl)oxidanyl-oxidised cellulose, (TEMPO)-oxidised cellulose nanofibers, cellulose, hemicellulose, or lignin.

9. The method according to claim 1, wherein the organic substrate is an agricultural waste product; a product or waste product from forestry industry; a waste stream or a waste product; or an industrial waste stream or waste product.

10. The method according to claim 1, wherein the light source has a wavelength between 180 and 850 nm.

11. The method according to claim 1, wherein:
   The organic substrate comprises cellulose;
   The reductant is ascorbic acid;
   The light harvesting molecule is chlorophyllide a and/or chlorophyllin.

12. The method according to claim 1, wherein:
   The organic substrate comprises cellulose;
   The reductant is ascorbic acid;
   The light harvesting molecule is a thylakoid membrane.

13. The method according to claim 11, wherein the AA10 LPMO is selected from the group consisting of TfLPMOa from *Thermobifida fusca*, TtGH61R from *Thielavia terrestris*, and TaGH61A from *Thermoascus aurantiacus*.

14. The method according to claim 12, wherein the AA10 LPMO is selected from the group consisting of TfLPMOa from *Thermobifida fusca*, TtGH61R from *Thielavia terrestris*, and TaGH61A from *Thermoascus aurantiacus*.

15. The method according to claim 12, wherein the thylakoid membrane is a thylakoid membrane from a cyanobacterium.

16. The method according to claim 14, wherein the thylakoid membrane is a thylakoid membrane from a cyanobacterium.

* * * * *